US012054526B2

(12) United States Patent
Millay et al.

(10) Patent No.: US 12,054,526 B2
(45) Date of Patent: Aug. 6, 2024

(54) POLYPEPTIDES, NUCLEIC ACID MOLECULES, COMPOSITIONS, AND RELATED METHODS

(71) Applicants: CHILDREN'S HOSPITAL MEDICAL CENTER, Cincinnati, OH (US); THE UNITED STATES OF AMERICA AS REPRESENTED BY THE SECRETARY, DEPT. OF HEALTH AND HUMAN SERVICES, Bethesda, MD (US)

(72) Inventors: Douglas Millay, Park Hills, KY (US); Dilani Gamage, Cincinnati, OH (US); Leonid Chernomordik, North Potomac, MD (US); Evgenia Leikina, Derwood, MD (US)

(73) Assignees: CHILDREN'S HOSPITAL MEDICAL CENTER, Cincinnati, OH (US); USA AS REPRESENTED BY THE SECRETARY, DEPT. OF HHS, Bethesda, MD (US)

( * ) Notice: Subject to any disclaimer, the term of this patent is extended or adjusted under 35 U.S.C. 154(b) by 0 days.

(21) Appl. No.: 17/251,019

(22) PCT Filed: Jun. 14, 2019

(86) PCT No.: PCT/US2019/037169
§ 371 (c)(1),
(2) Date: Dec. 10, 2020

(87) PCT Pub. No.: WO2019/241622
PCT Pub. Date: Dec. 19, 2019

(65) Prior Publication Data

US 2021/0253655 A1 Aug. 19, 2021

Related U.S. Application Data

(60) Provisional application No. 62/685,320, filed on Jun. 15, 2018.

(51) Int. Cl.
*A61K 38/17* (2006.01)
*C07K 14/47* (2006.01)
(Continued)

(52) U.S. Cl.
CPC .......... *C07K 14/4716* (2013.01); *A61K 38/17* (2013.01); *C12N 5/16* (2013.01); *A61K 38/00* (2013.01)

(58) Field of Classification Search
CPC .... C07K 14/4716; A61K 38/00; A61K 38/16; A61K 38/17; C12N 5/16
See application file for complete search history.

(56) References Cited

U.S. PATENT DOCUMENTS

| | | | | |
|---|---|---|---|---|
| 4,554,101 A | 11/1985 | Hopp | | |
| 7,223,593 B2 * | 5/2007 | Coffin | A61K 48/00 | 435/235.1 |

(Continued)

FOREIGN PATENT DOCUMENTS

| | | |
|---|---|---|
| WO | 2004/009834 A2 | 1/2004 |
| WO | 2007/128984 A2 | 11/2007 |

(Continued)

OTHER PUBLICATIONS

Shi et al. (2017) "Requirement of the fusogenic micropeptide myomixer for muscle formation in zebrafish" Proc Natl Acad Sci U S A, vol. 114, pp. 11950-11955. (Year: 2017).*

(Continued)

*Primary Examiner* — Kevin S Orwig
*Assistant Examiner* — John Michael Cronin
(74) *Attorney, Agent, or Firm* — ALGM LLP; Harry J. Guttman

(57) ABSTRACT

Some embodiments of the invention include polypeptides comprising a myomerger polypeptide or an extracellular myomerger polypeptide. Other embodiments of the inven- (Continued)

tion include nucleic acid molecules encoding polypeptides comprising a myomerger polypeptide or an extracellular myomerger polypeptide. Other embodiments of the invention include vectors comprising the nucleic acid molecule. Yet other embodiments of the invention include methods of using a myomerger polypeptide or an extracellular myomerger polypeptide. Additional embodiments of the invention are also discussed herein.

27 Claims, 49 Drawing Sheets

Specification includes a Sequence Listing.

(51) Int. Cl.

| | |
|---|---|
| *C12N 5/16* | (2006.01) |
| *A61K 38/00* | (2006.01) |

(56) References Cited

U.S. PATENT DOCUMENTS

| | | | | |
|---|---|---|---|---|
| 7,316,898 | B2 * | 1/2008 | Sweeney | G01N 21/33 435/235.1 |
| 10,272,137 | B2 * | 4/2019 | Olson | A61K 38/1719 |
| 2004/0048249 | A1 | 3/2004 | Tang et al. | |
| 2005/0265978 | A1 | 12/2005 | Chancellor et al. | |
| 2009/0192107 | A1 | 7/2009 | Crockard et al. | |
| 2014/0210448 | A1 | 7/2014 | Brunda | |
| 2015/0238526 | A1 | 8/2015 | Huss et al. | |
| 2016/0136240 | A1 | 5/2016 | Olson et al. | |
| 2016/0168572 | A1 | 6/2016 | Lotvall et al. | |
| 2019/0358294 | A1 | 11/2019 | Olson et al. | |
| 2019/0382732 | A1 | 12/2019 | Olson et al. | |
| 2020/0048318 | A1 * | 2/2020 | Millay | C07K 14/4716 |

FOREIGN PATENT DOCUMENTS

| | | | | |
|---|---|---|---|---|
| WO | 2012/031008 | A2 | 3/2012 | |
| WO | 2014076137 | A1 | 5/2014 | |
| WO | 2014/210448 | A1 | 12/2014 | |
| WO | 2018/087720 | A1 | 5/2018 | |
| WO | WO-2018087720 | A1 * | 5/2018 | A61K 39/001102 |
| WO | 2018/152103 | A1 | 8/2018 | |
| WO | 2018/156397 | A1 | 8/2018 | |
| WO | 2019/241622 | A1 | 12/2019 | |

OTHER PUBLICATIONS

Sampath et al. (2018) "Myoblast fusion confusion: the resolution begins" Skeletal Muscle, vol. 8, Article 3 (10 pages) (Year: 2018).*
Vector Biolabs May 24, 2006, examiner generated from date limited google search engine and https://www.vectorbiolabs.com/faq-recombinant-adenovirus/, Feb. 9, 2023 (Year: 2006).*
Chen et al. (2005) "Molecular Cloning and Functional Analysis of ESGP, an Embryonic Stem Cell and Germ Cell Specific Protein" Acta Biochim Biophys Sin, vol. 37, No. 12, pp. 789-796.
Dai et al. (1992) "Gene therapy via primary myoblasts: Long-term expression of factor IX protein following transplantation in vivo" Proc Natl Acad Sci USA, vol. 89, No. 22, pp. 10892-10895.
Mitani et al. (2017) "In vivo myomaker-mediated heterologous fusion and nuclear reprogramming" FASEB J, vol. 31, No. 1, pp. 400-411.
Pei et al. (2011) "CREST—a large and diverse superfamily of putative transmembrane hydrolases" Biology Direct, vol. 6, Article 37 (17 pages).
Van Dommelen et al. (2012) "Microvesicles and exosomes: Opportunities for cell-derived membrane vesicles in drug delivery" J Control Release, vol. 161, No. 2, pp. 635-644.
Perez-Vargas et al. (2014) "Structural basis of eukaryotic cell-cell fusion" Cell, vol. 157, pp. 407-419.
Pietuch et al. (2013) "Membrane tension homeostasis of epithelial cells through surface area regulation in response to osmotic stress" Biochim Biophys Acta, vol. 1833, pp. 712-722.
Podbilewicz (2014) "Virus and cell fusion mechanisms" Annu Rev Cell Dev Biol, vol. 30, pp. 111-139.
Podbilewicz et al. (2006) "The C. elegans developmental fusogen EFF-1 mediates homotypic fusion in heterologous cells and in vivo" Dev Cell, vol. 11, pp. 471-481.
Quinn et al. (2017) "Myomerger induces fusion of non-fusogenic cells and is required for skeletal muscle development" Nat Commun, vol. 8, Article 15665 (9 pages).
Rand et al. (1985) "Dynamic morphology of calcium-induced interactions between phosphatidylserine vesicles" Biophys J, vol. 47, pp. 483-489.
Randrianarison-Huetz et al. (2017) "Srf controls satellite cell fusion through the maintenance of actin architecture" J Cell Biol, vol. 217, pp. 685-700.
Sampath et al. (2018) "Myoblast fusion confusion: the resolution begins" Skeletal Muscle, vol. 8, Article 3 (10 pages).
Schejter, E.D. (2016). Myoblast fusion: Experimental systems and cellular mechanisms. Semin Cell Dev Biol, vol. 60, pp. 112-120.
Schindelin et al. (2012) "Fiji: an open-source platform for biological-image analysis" Nat Methods, vol. 9, pp. 676-682.
Schmid et al. (2011) "Dynamin: functional design of a membrane fission catalyst" Annu Rev Cell Dev Biol, vol. 27, pp. 79-105.
Schwander et al. (2003) "Beta1 integrins regulate myoblast fusion and sarcomere assembly" Dev Cell, vol. 4, pp. 673-685.
Sens et al. (2010) "An invasive podosome-like structure promotes fusion pore formation during myoblast fusion" J Cell Biol, vol. 191, pp. 1013-1027.
Shi et al. (2017) "Requirement of the fusogenic micropeptide myomixer for muscle formation in zebrafish" Proc Natl Acad Sci U S A, vol. 114, pp. 11950-11955.
Shilagardi et al. (2013) "Actin-propelled invasive membrane protrusions promote fusogenic protein engagement during cell-cell fusion" Science, vol. 340, pp. 359-363.
Valansi et al. (2017) "*Arabidopsis* HAP2/GCS1 is a gamete fusion protein homologous to somatic and viral fusogens" J Cell Biol, vol. 216, pp. 571-581.
Vasyutina et al. (2009) "The small G-proteins Rac1 and Cdc42 are essential for myoblast fusion in the mouse" Proc Natl Acad Sci U S A, vol. 106, pp. 8935-8940.
Verma et al. (2014) "Late stages of the synchronized macrophage fusion in osteoclast formation depend on dynamin" Biochem J, vol. 464, pp. 293-300.
Weber et al. (1998) "SNAREpins: minimal machinery for membrane fusion" Cell, vol. 92, pp. 759-772.
Wen et al. (2017) "Kiss-and-Run Is a Significant Contributor to Synaptic Exocytosis and Endocytosis in Photoreceptors" Front Cell Neurosci, vol. 11, Article 286 (18 pages).
White et al. (2008) "Structures and mechanisms of viral membrane fusion proteins: multiple variations on a common theme" Crit Rev Biochem Mol Biol, vol. 43, pp. 189-219.
Wilson et al. (2015) "Hemagglutinin clusters in the plasma membrane are not enriched with cholesterol and sphingolipids" Biophys J, vol. 108, pp. 1652-1659.
Xu et al. (2005) "Hemifusion in SNARE-mediated membrane fusion" Nature structural & molecular biology, vol. 12, pp. 417-422.
Yang et al. (2010) "Cell-penetrating peptide induces leaky fusion of liposomes containing late endosome-specific anionic lipid" Biophys J, vol. 99, pp. 2525-2533.
Zhang et al. (2017) "The microprotein Minion controls cell fusion and muscle formation" Nat Commun, vol. 8, Article 15664 (15 pages).
International Search Report from PCT/US2019/037169, mailed Sep. 19, 2019, 5 pages.
Written Opinion from PCTAJS2019/037169, mailed Sep. 19, 2019, 6 pages.
Beck et al. (2001) "Control of the actin cytoskeleton by extracellular signals" Results Probl Cell Differ, vol. 32, pp. 231-262.
Bi et al. (2017) "Control of muscle formation by the fusogenic micropeptide myomixer" Science, vol. 356, pp. 323-327.

(56) References Cited

OTHER PUBLICATIONS

Bi et al. (2018) "Fusogenic micropeptide Myomixer is essential for satellite cell fusion and muscle regeneration" Proc Natl Acad Sci U S A, vol. 115, pp. 3864-3869.
Blijleven et al. (2016) "Mechanisms of influenza viral membrane fusion" Semin Cell Dev Biol, vol. 60, pp. 78-88.
Chernomordik et al. (1998) "The pathway of membrane fusion catalyzed by influenza hemagglutinin: restriction of lipids, hemifusion, and lipidic fusion pore formation" J Cell Biol, vol. 140, pp. 1369-1382.
Chernomordik et al. (2003) "Protein-lipid interplay in fusion and fission of biological membranes" Annu Rev Biochem, vol. 72, pp. 175-207.
Ciechonska et al. (2014) "Reovirus FAST proteins: virus-encoded cellular fusogens" Trends Microbiol, vol. 22, pp. 715-724.
Cohen et al. (2004) "The energetics of membrane fusion from binding, through hemifusion, pore formation, and pore enlargement" J Membr Biol, vol. 199, pp. 1-14.
Crowe et al. (2017) "A Proteoliposome Method for Assessing Nanotoxicity on Synaptic Fusion and Membrane Integrity" Small Methods, vol. 1, article 1700207 (6 pages).
Cummings et al. (2007) "Aggregation and hemi-fusion of anionic vesicles induced by the antimicrobial peptide cryptdin-4" Biochim Biophys Acta, vol. 1768, pp. 1796-1804.
Demonbreun et al. (2015) "Membrane fusion in muscle development and repair" Semin Cell Dev Biol, vol. 45, pp. 18-56.
Deng et al. (2017) "Acting on identity: Myoblast fusion and the formation of the syncytial muscle fiber" Semin Cell Dev Biol, vol. 72, pp. 45-55.
Di Gioia et al. (2017) "A defect in myoblast fusion underlies Carey-Fineman-Ziter syndrome" Nat Commun, vol. 8, Article 16077 (16 pages).
Duan et al. (2009) "Dependence of myoblast fusion on a cortical actin wall and nonmuscle myosin IIA" Dev Biol, vol. 325, pp. 374-385.
Duan et al. (2012) "Group I PAKs function downstream of Rac to promote podosome invasion during myoblast fusion in vivo" J Cell Biol, vol. 199, pp. 169-185.
Fedry et al. (2017) "The Ancient Gamete Fusogen HAP2 Is a Eukaryotic Class II Fusion Protein" Cell, vol. 168, pp. 904-915.
Finkelstein et al. (1986) "Osmotic swelling of vesicles: its role in the fusion of vesicles with planar phospholipid bilayer membranes and its possible role in exocytosis" Annu Rev Physiol, vol. 48, pp. 163-174.
Gamage et al. (2017) "Insights into the localization and function of myomaker during myoblast fusion" J Biol Chem, vol. 292, pp. 17272-17289.
Gruenbaum-Cohen et al. (2012) "The actin regulator N-WASp is required for muscle-cell fusion in mice" Proc Nati Acad Sci U S A, vol. 109, pp. 11211-11216.
Guan et al. (1992) "Identification of a single amino acid residue responsible for the binding of a class of beta-adrenergic receptor antagonists to 5-hydroxytryptamine1A receptors" Mol Pharmacol, vol. 41, pp. 695-698.
Hamoud et al. (2014) "G-protein coupled receptor BAI3 promotes myoblast fusion in vertebrates" Proc Natl Acad Sci U S A, vol. 111, pp. 3745-3750.
Hernandez et al. (2017) "The hallmarks of cell-cell fusion" Development, vol. 144, pp. 4481-4495.
Hochreiter-Hufford et al. (2013) "Phosphatidylserine receptor BAI1 and apoptotic cells as new promoters of myoblast fusion" Nature, vol. 497, pp. 263-267.
Horsley et al. (2003) "IL-4 acts as a myoblast recruitment factor during mammalian muscle growth" Cell, vol. 113, pp. 483-494.
Ivanovic et al. (2015) "Distinct functional determinants of influenza hemagglutinin-mediated membrane fusion" eLife, vol. 4, Article 11009 (24 pages).
Jahn et al. (1999) "Membrane fusion and exocytosis" Annu Rev Biochem, vol. 68, pp. 863-911.
Kattamuri et al. (2012) "Members of the DAN family are BMP antagonists that form highly stable noncovalent dimers" J Mol Biol, vol. 424, pp. 313-327.
Kielian et al. (2006) "Virus membrane-fusion proteins: more than one way to make a hairpin" Nat Rev Microbiol, vol. 4, pp. 67-76.
Kyoung et al. (2013) "Studying calcium-triggered vesicle fusion in a single vesicle-vesicle content and lipid-mixing system" Nat Protoc, vol. 8, pp. 1-16.
Leikina et al. (2000) "Reversible merger of membranes at the early stage of influenza hemagglutinin-mediated fusion" Mol Biol Cell, vol. 11, pp. 2359-2371.
Leikina et al. (2004) "Influenza hemagglutinins outside of the contact zone are necessary for fusion pore expansion" J Biol Chem, vol. 279, pp. 26526-26532.
Leikina et al. (2013) "Extracellular annexins and dynamin are important for sequential steps in myoblast fusion" J Cell Biol, vol. 200, pp. 109-123.
Leikina et al. (2018) "Myomaker and Myomerger work independently to control distinct steps of membrane remodeling during myoblast fusion" Developmental Cell, vol. 46, pp. 767-780.
Margam et al. (2018) "Myomaker and Myomerger: it takes two to make one" Developmental Cell, vol. 46, pp. 676-678.
Matsuzaki et al. (1998) "Relationship of membrane curvature to the formation of pores by magainin 2" Biochemistry, vol. 37, pp. 11856-11863.
Melikyan et al. (1995) "GPI-anchored influenza hemagglutinin induces hemifusion to both red blood cell and planar bilayer membranes" J Cell Biol, vol. 131, pp. 679-691.
Melikyan et al. (1997) "Inner but not outer membrane leaflets control the transition from glycosylphosphatidylinositol-anchored influenza hemagglutinin-induced hemifusion to full fusion" J Cell Biol, vol. 136, pp. 995-1005.
Millay et al. (2013) "Myomaker is a membrane activator of myoblast fusion and muscle formation" Nature, vol. 499, pp. 301-305.
Millay et al. (2014) "Myomaker is essential for muscle regeneration" Genes Dev, vol. 28, pp. 1641-1646.
Millay et al. (2016) "Structure-function analysis of myomaker domains required for myoblast fusion" Proc Natl Acad Sci U S A, vol. 113, pp. 2116-2121.
Moon et al. (2010) "A synergistic approach to protein crystallization: combination of a fixed-arm carrier with surface entropy reduction" Protein Sci, vol. 19, pp. 901-913.
Muller et al. (2011) "An alternate path for fusion and its exploration by field-theoretic means" Curr Top Membr, vol. 68, pp. 295-323.
Nazari et al. (2012) "Classifying surfactants with respect to their effect on lipid membrane order" Biophys J, vol. 102, pp. 498-506.
Nguyen et al. (2017) "Prokaryotic soluble expression and purification of bioactive human fibroblast growth factor 21 using maltose-binding protein" Sci Rep, vol. 7, Article 16139 (11 pages).
Nowak et al. (2009) "Nap1-mediated actin remodeling is essential for mammalian myoblast fusion" J Cell Sci, vol. 122, pp. 3282-3293.
Patel et al. (2014) "Additive and synergistic membrane permeabilization by antimicrobial (lipo)peptides and detergents" Biophys J, vol. 106, pp. 2115-2125.

* cited by examiner

D

E

F

G

H

D

F

G

H

I

J

A

B

C

D

E

F

G

H

I

J

L

M

N

O

P

D

E

F

G

H

I

J

K

C

D

E

F

G

H

I

J

K

L

POLYPEPTIDES, NUCLEIC ACID MOLECULES, COMPOSITIONS, AND RELATED METHODS

CROSS-REFERENCE TO RELATED APPLICATIONS

This application is a National Stage Entry of International Application No. PCT/US2019/037169 filed Jun. 14, 2019, entitled "POLYPEPTIDES, NUCLEIC ACID MOLECULES, COMPOSITIONS, AND RELATED METHODS" which is herein incorporated by reference in its entirety, and which claims the benefit of U.S. Provisional Application No. 62/685,320, filed Jun. 15, 2018 entitled "Myomerger as a Membrane Disrupter" which is herein incorporated by reference in its entirety. 2020_12_seq_listing_36821_04057_ST25.txt, file creation date: Dec. 8, 2020, and file size: 22 KB)

BACKGROUND

Several molecules or methods are known to increase cell permeability. In some instances, increasing cell permeability can assist in the treatment of diseases (e.g., infections). However, additional methods for such treatments are desired.

Certain embodiments of the invention address one or more of the deficiencies described above. For example, some embodiments of the invention include polypeptides comprising a myomerger polypeptide or an extracellular myomerger polypeptide. Other embodiments of the invention include nucleic acid molecules encoding polypeptides comprising a myomerger polypeptide or an extracellular myomerger polypeptide. Other embodiments of the invention include vectors comprising the nucleic acid molecule. Yet other embodiments of the invention include methods of using a myomerger polypeptide or an extracellular myomerger polypeptide. Additional embodiments of the invention are also discussed herein.

SUMMARY

Some embodiments of the invention include a polypeptide comprising an extracellular myomerger polypeptide. In other embodiments, the polypeptide is not a myomerger polypeptide. In still other embodiments, the polypeptide is an extracellular myomerger polypeptide. In yet other embodiments, the polypeptide comprises at least one amino acid modification relative to an extracellular wt-myomerger polypeptide. In certain embodiments, the polypeptide comprises at least one amino acid modification relative to an extracellular wt-myomerger polypeptide and the at least one amino acid modification is an insertion, a deletion, a substitution or a conservative substitution. In some embodiments, the polypeptide is selected from the group consisting of SEQ ID NO: 19, SEQ ID NO: 20, SEQ ID NO: 21, SEQ ID NO: 22, SEQ ID NO: 23, and SEQ ID NO: 24. In other embodiments, the polypeptide is not SEQ ID NO: 19, SEQ ID NO: 20, SEQ ID NO: 21, SEQ ID NO: 22, SEQ ID NO: 23, or SEQ ID NO: 24. In still other embodiments, the polypeptide comprises (a) amino acids 4-15 of any of SEQ ID Nos: 19-24, (b) amino acids 18-32 of any of SEQ ID Nos: 19-24, or (c) both. In yet other embodiments, the polypeptide comprises (a) LLPLLRRLARRL (SEQ ID NO:25), (b) QDMREALLSCLLFVL (SEQ ID NO:26) or QDMREALLGCLLFIL (SEQ ID NO:27), or (c) both. In certain embodiments, the polypeptide is a human extracellular myomerger polypeptide or a mouse extracellular myomerger polypeptide. In other embodiments, the polypeptide sequence has at least an 80% sequence identity to an extracellular wt-myomerger polypeptide. In still other embodiments, the polypeptide sequence has at least a 90% sequence identity to an extracellular wt-myomerger polypeptide.

Some embodiments of the invention include a nucleic acid molecule encoding a polypeptide such as but not limited to any polypeptide disclosed herein (e.g., extracellular myomerger polypeptide). In other embodiments, the nucleic acid molecule is included in a vector, a viral vector, or a plasmid.

Some embodiments of the invention include a vector comprising any nucleic acid molecule disclosed herein (e.g., extracellular myomerger nucleic acid molecule).

Some embodiments of the invention include a composition comprising any polypeptide disclosed herein (e.g., extracellular myomerger polypeptide), any nucleic acid molecule disclosed herein (e.g., extracellular myomerger nucleic acid molecule), or any vector disclosed herein. In other embodiments, the amount of the polypeptide, the nucleic acid molecule, or the vector is from about 0.0001% (by weight total composition) to about 99%.

Some embodiments of the invention include a pharmaceutical composition comprising any polypeptide disclosed herein (e.g., extracellular myomerger polypeptide), any nucleic acid molecule disclosed herein (e.g., extracellular myomerger nucleic acid molecule), or any vector disclosed herein. In certain embodiments, the amount of the polypeptide, the nucleic acid molecule, or the vector is from about 0.0001% (by weight total composition) to about 50%.

Some embodiments of the invention include a method for increasing the membrane permeability of a cell or a liposome, comprising contacting the cell or the liposome with a myomerger polypeptide, an extracellular myomerger polypeptide, any composition disclosed herein, or any pharmaceutical composition disclosed herein. In some embodiments, the cell is a bacterial cell, a fungal cell, an insect cell, an animal cell, or a mammalian cell. In other embodiments, the cell is a bacterial cell or a mammalian cell. In yet other embodiments, the cell is a gram-positive bacterial cell or a gram-negative bacterial cell. In still other embodiments, the cell is a cancer cell. In certain embodiments, the cell is a cancer cell and the cancer cell is a tumor cell. In some embodiments, the contacting occurs in vitro. In other embodiments, the contacting occurs in vivo. In still other embodiments, the contacting comprises an injection. In yet other embodiments, the method results in one or more pores in the cell membrane or the liposome membrane. In certain embodiments, the method results in lysing cells or lysing liposomes.

Some embodiments of the invention include a method for promoting or increasing fusion activity between a first cell and a second cell, comprising contacting the first cell, the second cell, or both with a myomerger polypeptide, an extracellular myomerger polypeptide, any composition disclosed herein, or any pharmaceutical composition disclosed herein. In certain embodiments, the first cell and the second cell can be the same or different and each is selected from an animal cell, a mammalian cell, a human cell, a rat cell, a mouse cell, a muscle cell, a non-muscle cell, a myoblast, a fibroblast, a C2C12 cell, a 10T ½ fibroblast, an NIH/3T3 cell, a CHO cell, a mesenchymal stem cell (MSC), a hematopoietic stem cell, a blood cell, a red blood cell, a bone marrow cell, and an adipose stem cell. In other embodiments, the first cell and the second cell can be the same or different and each is a muscle cell or a myoblast.

Other embodiments of the invention are also discussed herein.

BRIEF DESCRIPTION OF THE DRAWINGS

The following drawings form part of the present specification and are included to further demonstrate certain aspects of the present invention. The invention may be better understood by reference to one or more of these drawings in combination with the description of specific embodiments presented herein.

DETAILED DESCRIPTION

Figure 1:
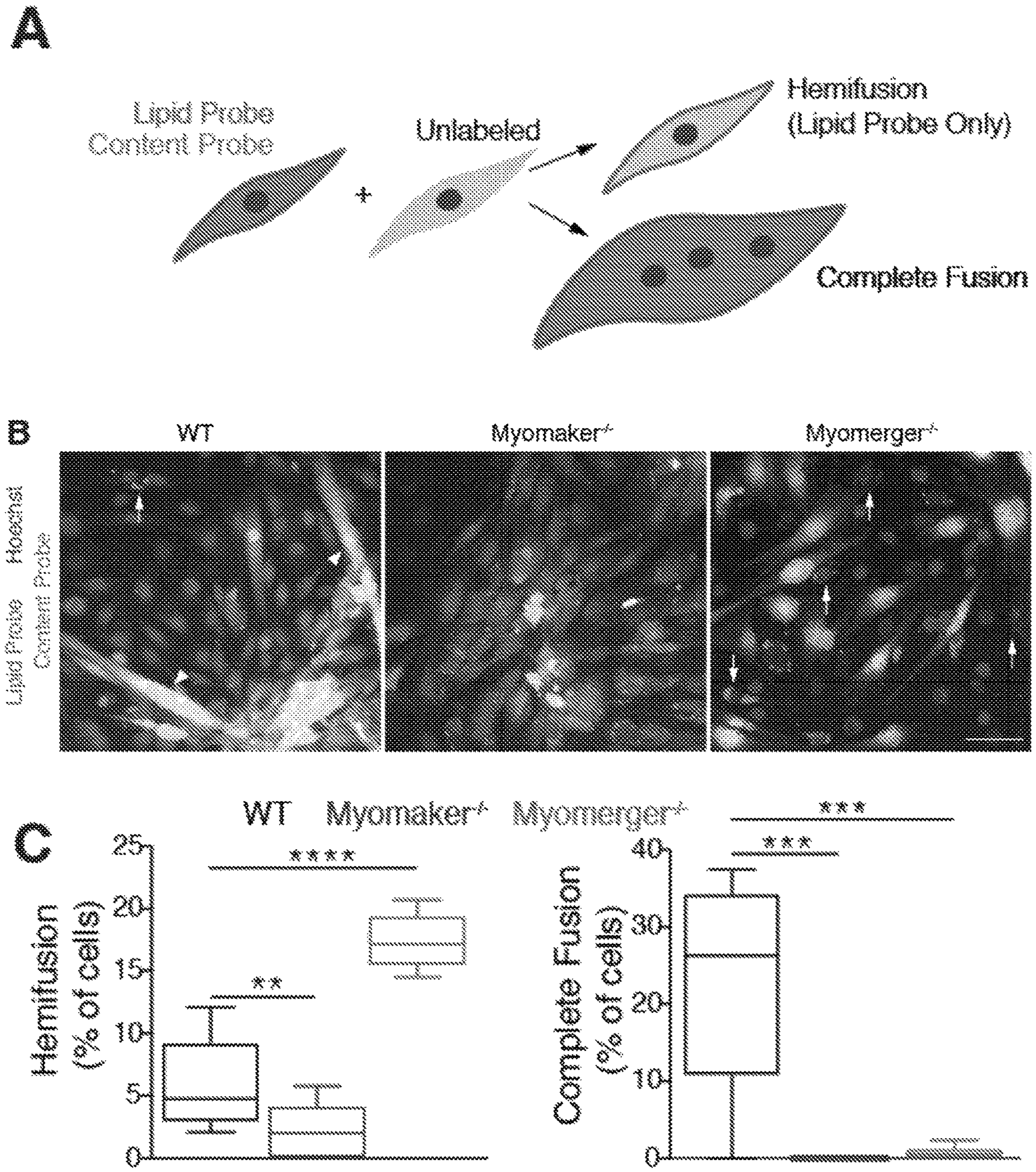
FIG. 1: Distinct roles for Myomaker and Myomerger during the fusion process. (A) Unsynchronized cell fusion assay (no LPC) to monitor lipid and content mixing. Cells are differentiated for 48 hours then one population is labeled with both lipid (red, DiI) and content (green cell tracker) probes and mixed with unlabeled cells. Hemifusion is identified as mononucleated cells with only the red lipid probe whereas complete fusion is identified as multinucleated cells with both probes, and these indices were scored 24 hours after mixing the labeled and unlabeled cells. (B) Immunofluorescence images of WT, Myomaker$^{-/-}$ and Myomerger$^{-/-}$ C2C12 myoblasts after lipid and content mixing. Arrows indicate hemifused cells, whereas arrowheads mark complete fusion. (C) Quantification of hemifusion (left, n=3 independent experiments) and complete fusion (right, n=3 independent experiments) as a percentage to total cells. (F) Schematic of content mixing to assess formation of fusion pores. (G) Fusion pore formation was identified by the appearance of double labeled cells (arrows) in WT and Myomerger$^{-/-}$ C2C12 myoblasts after 24 hours. (H) Quantification of (G) (n=3 independent experiments) as a percentage of total cells. Statistical analyses and data presentation: (C) (Hemifusion), two tailed Student's t-test; (C) (complete fusion), (H), Mann-Whitney test; box-and-whisker plots show median (center line), 25th-75th percentiles (box) and minimumand maxima values (whiskers); $^{}P<0.01$, $^{*}P<0.001$, $^{****}P<0.0001$. Scale bars, 50 μm. See also (D) and (E).
Figure 1:
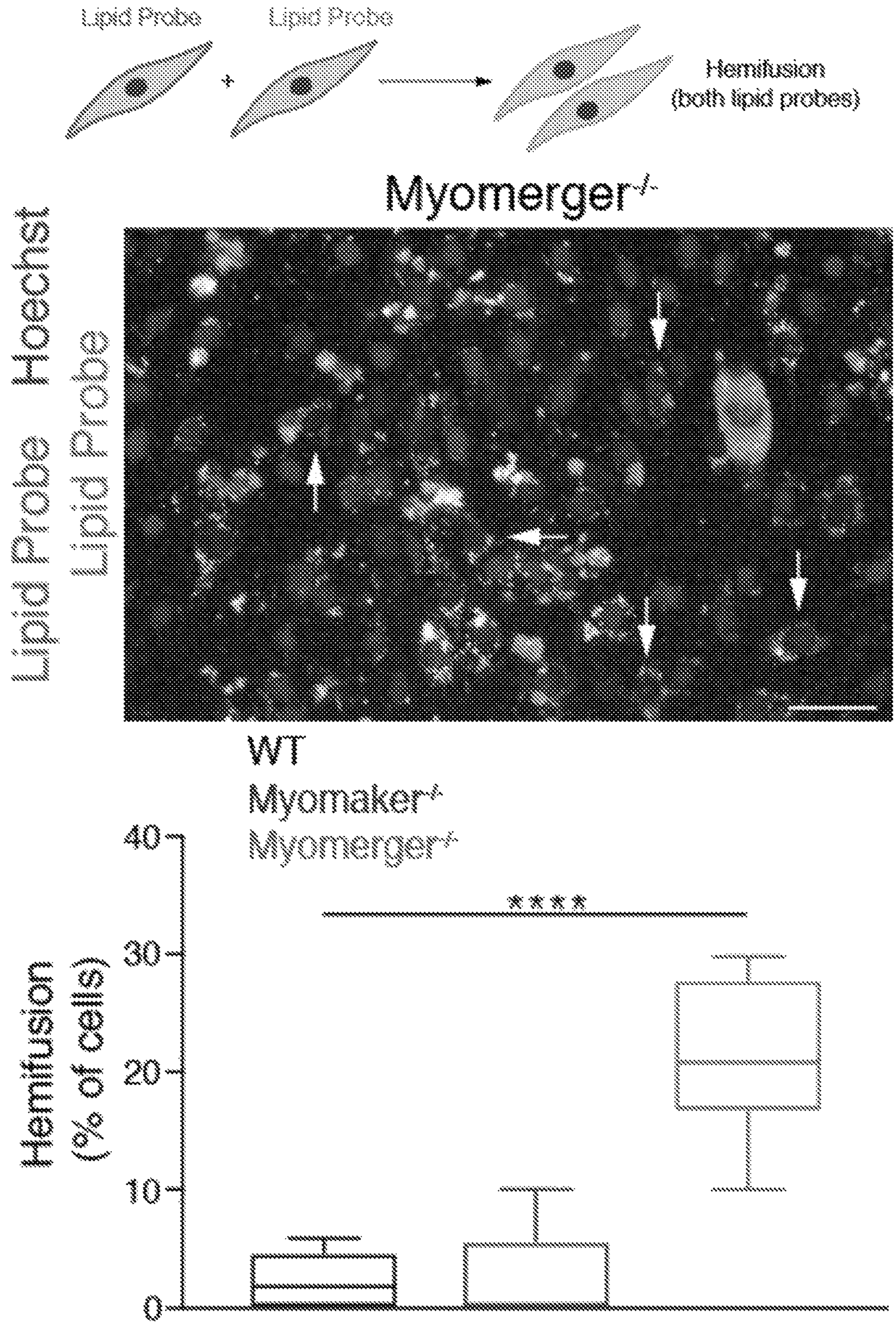
Figure 1:
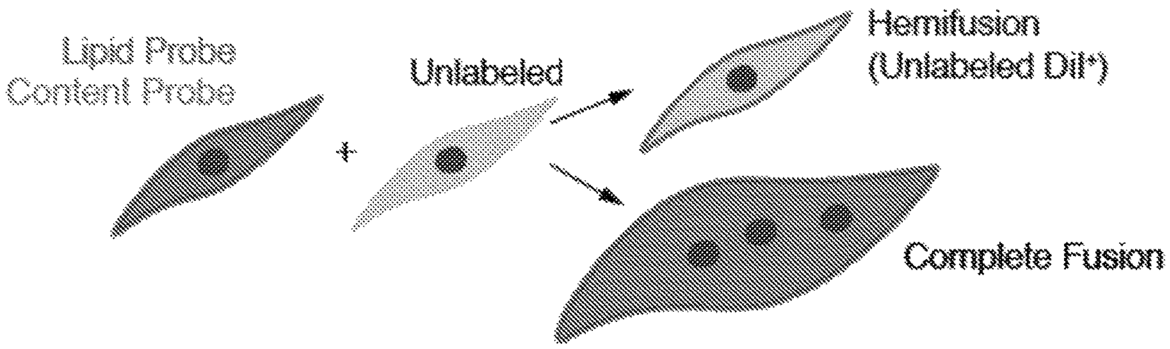
Figure 1:
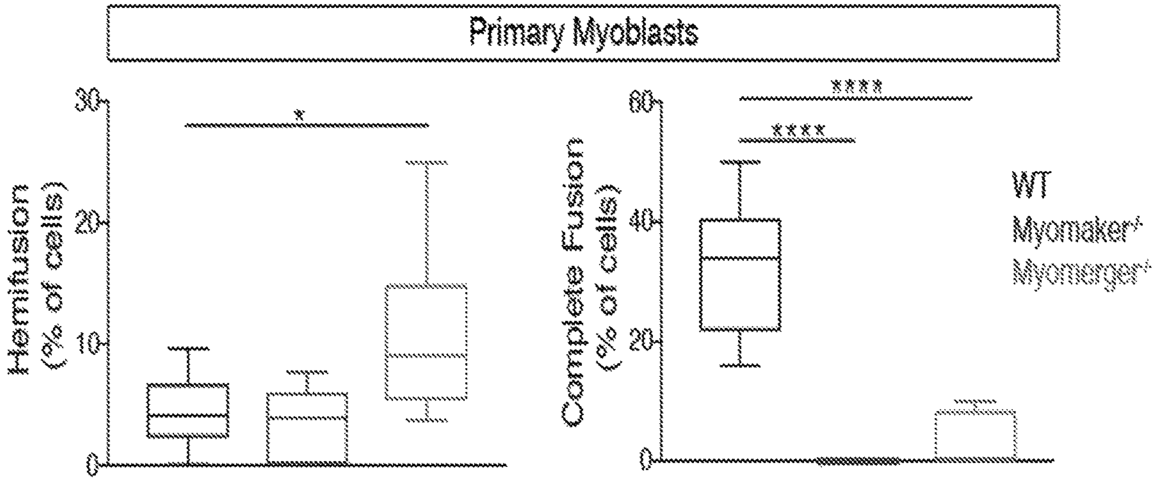
Figure 1:
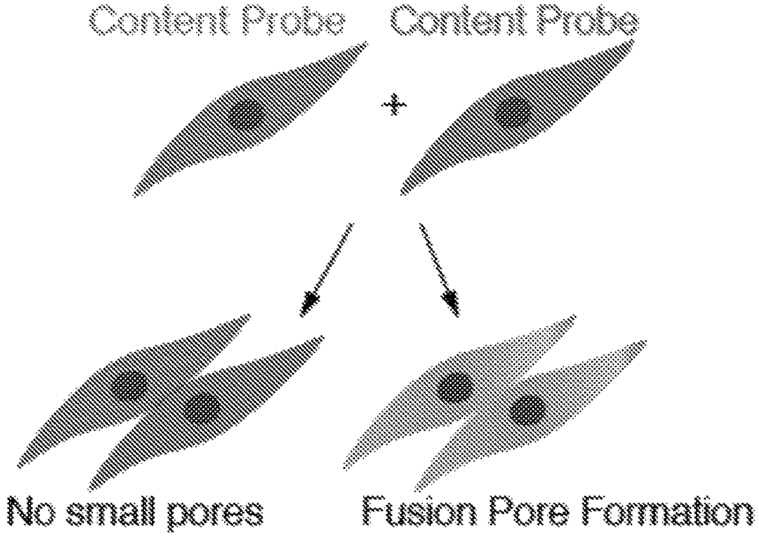
Figure 1:
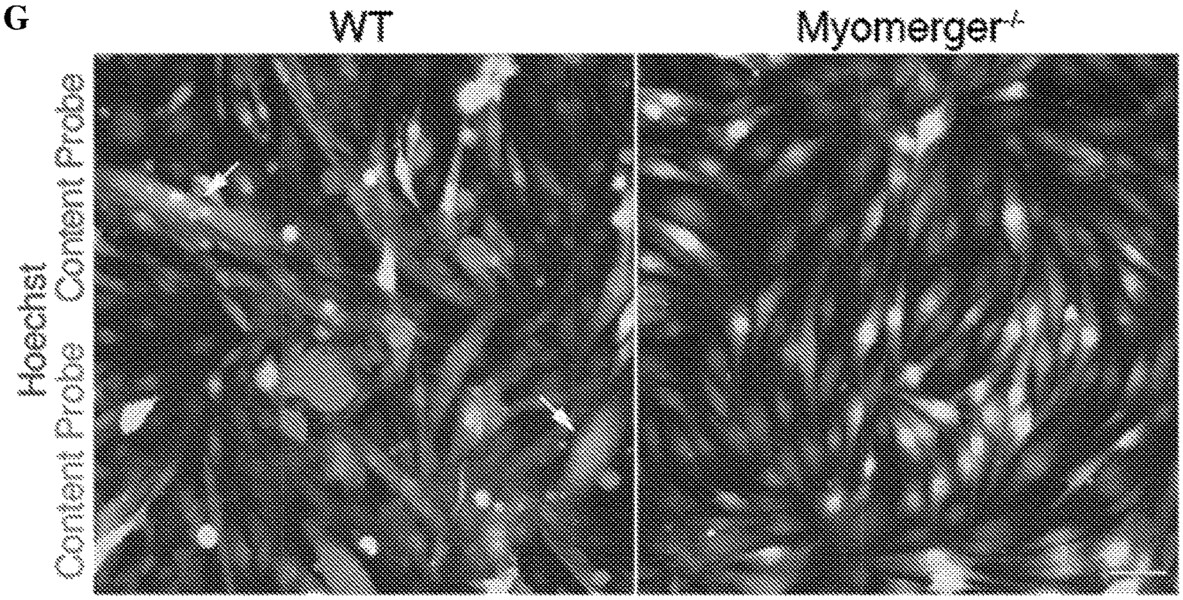
Figure 1:
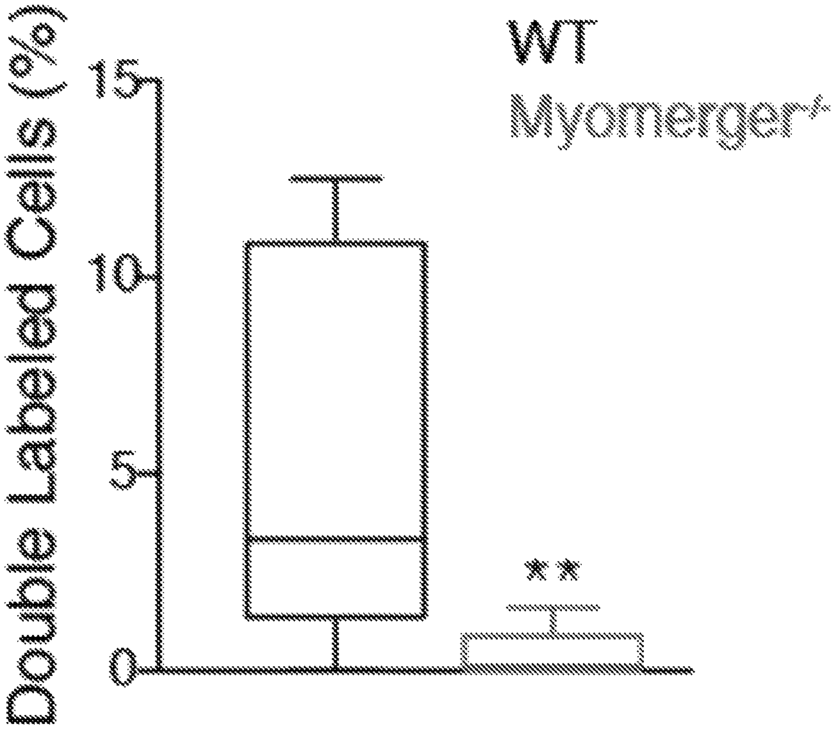

While embodiments encompassing the general inventive concepts may take diverse forms, various embodiments will be described herein, with the understanding that the present disclosure is to be considered merely exemplary, and the general inventive concepts are not intended to be limited to the disclosed embodiments.

Some embodiments of the invention include polypeptides comprising a myomerger polypeptide or an extracellular myomerger polypeptide. Other embodiments of the invention include nucleic acid molecules encoding polypeptides comprising a myomerger polypeptide or an extracellular myomerger polypeptide. Other embodiments of the invention include vectors comprising the nucleic acid molecule. Yet other embodiments of the invention include methods of using a myomerger polypeptide or an extracellular myomerger polypeptide. Additional embodiments of the invention are also discussed herein. WO 2018/152103 A1 (PCT/US2018/017991 filed Feb. 13, 2018) is herein incorporated by reference in its entirety.

Inventive Polypeptides, Nucleic Acid Molecules, and Compositions

Some embodiments of the invention include inventive polypeptides comprising a myomerger polypeptide or an extracellular myomerger polypeptide. In some embodiments, the extracellular myomerger polypeptide is the extracellular portion of a myomerger polypeptide (e.g., when it is membrane-bound, the extracellular portion is outside of the cell/liposome, and not in the membrane). In other embodiments, the extracellular myomerger polypeptide is the ectodomain of a myomerger polypeptide. In some embodiments, the myomerger polypeptide or the extracellular myomerger polypeptide can be a polypeptide that (a) induces fusogenicity (e.g., by inducing the fusion of myomaker-expressing fibroblasts), (b) can confer fusogenic activity to normally non-fusogenic cells, (c) is expressed during developmental myogenesis, (d) is expressed during regenerative myogenesis, (e) is expressed only during developmental myogenesis, (f) is expressed only during regenerative myogenesis, (g) permeabilizes the membrane of a cell or liposome (h) lyses a cell or liposome, (i) forms pores in a cell membrane or liposome membrane, (j) stresses a membrane (e.g., cell membranes or liposome membranes) or (k) combinations thereof.

The term "myomerger polypeptide" encompasses "wt-myomerger polypeptides" (i.e., myomerger polypeptides found in nature without any purposely human-made modification) and "mutant myomerger polypeptides" (e.g., with one or more modifications made to a wt-myomerger polypeptide). The term "extracellular myomerger polypeptide" encompasses "extracellular wt-myomerger polypeptides" (i.e., extracellular portions of myomerger polypeptides made from wt-myomerger polypeptides) and "mutant extracellular myomerger polypeptides" (e.g., with one or more modifications made to an extracellular wt-myomerger polypeptide).

Nonlimiting examples of wt-myomerger polypeptides are found in Table 1A. In other embodiments, the myomerger polypeptide has at least one amino acid modification relative to a wt-myomerger polypeptide. A wt-myomerger polypeptide can, in some embodiments, be a myomerger polypeptide from any animal including but not limited to a mammal, a rat, a cat, a rabbit, a human, a cow, a chicken, a turkey, a monkey, a tree shrew, a dog, a pig, a shrew, an elephant, or an opossum. Table 1A provides nonlimiting examples of wt-myomerger polypeptides and Tables 1B and 1C provide nonlimiting examples of related nucleic acid sequences (including start and stop codons).

TABLE 1A

| Myomerger | |
|---|---|
| Source | Polypeptide sequence |
| Mouse (long) | MPEESCTVKLIQLKTGEYRGAGPAMPVPLLPMVLRSLLSRLLLPVARLA RQHLLPLLRRLARRLSSQDMREALLSCLLFVLSQQQPPDSGEASRVDHS QRKERLGPQK (SEQ ID NO: 1) |
| Mouse (short) | MPVPLLPMVLRSLLSRLLLPVARLARQHLLPLLRRLARRLSSQDMREAL LSCLLFVLSQQQPPDSGEASRVDHSQRKERLGPQK (SEQ ID NO: 2) |
| Human | MPTPLLPLLLRLLLSCLLLPAARLARQYLLPLLRRLARRLGSQDMREAL LGCLLFILSQRHSPDAGEASRVDRLERRERLGPQK (SEQ ID NO: 3) |
| Cat | MPAPLLPLLLRTLMSRLLLPATRLARRHLLPLLRRLARRLGSQDVREAL LGCLLFILSQSRPPDAEEVSRVAGQERRERLAPPK (SEQ ID NO: 4) |
| Rabbit | MPAPLLPLLLRTLLSRLLLPAARLARRHLLPLLRRLAQRLGSQGTREALL GCLLFVLSQRQPPDASGEASRVDPPERKERLGRQK (SEQ ID NO: 5) |
| Dog | MPAPLLPLLLRTLVSRLLLPAARLARRHLLPLLRGLARRLGSQEVREAL LGCLLFILSQRHPPDAEEASRVAGQERKERLAPPK (SEQ ID NO: 6) |
| Elephant | MPVPLLSLLLRALLSRLLLPAARLARQHLLPLLRRLARRLGSQDMRQAL LGCLLFVLSQQHPPDAGEASREALSERRGRLAPQK (SEQ ID NO: 7) |

TABLE 1B

| Myomerger | |
|---|---|
| Source | cDNA nucleic acid sequence |
| Mouse (long) | atgcc agaagaaagc tgcactgtaa aactaatcca gttgaaaact ggggagtaca gaggtgcagg tcctgccatg cccgttccat tgctcccgat ggtgcttcga tcgctgctgt cccgcctgct gctgcctgtt gcccgcctgg cccggcagca cctcctgccc ttgctgcgcc ggctggcccg ccgactgagc tcccaagaca tgagagaggc tctgctgagc tgtctgctct ttgtcctcag ccagcaacag ccaccggatt ctggagaggc ctccagagtg gaccactccc agaggaagga gagattgggc ccccagaagt ga (SEQ ID NO: 8) |
| Mouse (short) | atgcccg ttccattgct cccgatggtg cttcgatcgc tgctgtcccg cctgctgctg cctgttgccc gcctggcccg gcagcacctc ctgcccttgc tgcgccggct ggcccgccga ctgagctccc aagacatgag agaggctctg ctgagctgtc tgctctttgt cctcagccag caacagccac cggattctgg agaggcctcc agagtggacc actcccagag gaaggagaga ttgggccccc agaagtga (SEQ ID NO: 9) |
| Human | atgcccac gccactgctc ccgctgctgc ttcgattgct gctgtcctgc ctgctgctgc ctgctgcccg cctggcccgc caatacctcc tgcccctgct gcgccgattg gcccgccgcc tgggctccca ggacatgcga gaggctttgc tgggctgtct gctgttcatt ctcagccagc gacactcgcc agacgctggg gaggcctcaa gagtggaccg cctggagagg agggagaggt taggccccca aaagtga (SEQ ID NO: 10) |
| Cat | atgcccgc tccactgctc ccactgctgc ttcgaaccct gatgtcccgc ttgctgctgc ctgccacccg cctggcccgc cggcacctcc tgcccctcct gcgccgactg gcccgccgcc tgggctcgca ggatgttcga gaagctttgc tgggctgtct gttgttcatc ctcagccaga gccgcccgcc cgacgctgag gaggtctcca gagtggctgg ccaggagagg agggagaggc tagctccccc aaaatga (SEQ ID NO: 11) |
| Rabbit | atgcc tgccccctg ctgccgctgc tgctgcgaac gctgctgtcc cgtctgctgc tgcccgctgc ccgcctggcc cgccggcacc tcctgcccct gctgcgccga ctggctcaac gcctgggctc ccagggcacg cgcgaggctt tgctgggctg tttgctgttt gtcctcagcc agagacagcc gccagatgcc tctggggagg cctccagagt ggacccaccg gagaggaagg agaggttagg ccgccaaaag tga (SEQ ID NO: 12) |
| Dog | atgc ctgctccact gctcccactg ctgctgcgaa cgctggtgtc tcgcctgctg ctgcctgctg cccgcctggc ccggcggcac ctcctgcccc tgctgcgtgg actggcccgc cgcctaggct cgcaggaggt tcgagaggct ttgctgggct gtctgttgtt catcctcagc cagagacatc cgccggacgc cgaggaggcc tccagagtgg ctggccagga gaggaaggag aggctagctc cccccaaatg a (SEQ ID NO: 13) |

TABLE 1B-continued

| Myomerger | |
|---|---|
| Source | cDNA nucleic acid sequence |
| Elephant | atgcccgtcc cgctgctctc gctgctgctg cgcgcgctgc tgtcccgcct gctgctgcct<br>gctgcccgcc tggcccgcca gcacctcctg cccctcctgc gccgacttgc tcgccgcctg<br>ggctcccagg acatgcgaca ggctctcttg ggatgtctgc tctttgtcct cagccagcaa<br>cacccgccgg acgctggtga ggcctccaga gaggccctct cagagaggag agggaggcta<br>gccccccaaa agtga (SEQ ID NO: 14) |

TABLE 1C

| (exons in lowercase) - Myomerger | |
|---|---|
| Source | Genomic nucleic acid sequence |
| Human (+strand) - start codon is bold & underlined; stop codon is bold and italicized | ctgcccggtgagagctgccgtggattggtggggGTAGGGGACTGAGAGGTCAGGGAGTGT<br>CAGGTCAGGGTGGATCAGGAGCCCCAAAAGAAAAATTGAGAATTGCCTGGAGAAGAACTC<br>CTGCTAGACTGAGGGAGAAGGGTTAGGGAACTCCAGGGGCATTGAGGCTGTGCAAGAGGA<br>GGGGGTGACTAGAGGAAGGGAGGGGCCAGGGAGCAGTAGGAATGCCTGGAGCTGGGAACG<br>GCAAGCTGTAGGTCTTGGTTTACTCTTGCCTTGGTTCAGTCTCCCCATCTGTGCTATGGT<br>GAGAACCTTCCTGCCTCAGCTGCCTTGCCAAGAGAAAGGGCTTCATGAAAGCAAAAATGA<br>CCTACAAATTGAGGTCAGGAGCAGGAAGGTGTAAACTGAAGGGAGGGGGAACTCCTGCCC<br>ACCCCATGTCCTTGCCAGGTGAGGCAGAACCAGGACATGCAAGCCTAAAGTCTGTGTTGT<br>CTTCCCAGgcactgactcactggccctgcc**atg**cccacgccactgctcccgctgctgctt<br>cgattgctgctgtcctgcctgctgctgcctgctgcccgcctggcccgccaatacctcctg<br>cccctgctgcgccgattggcccgccgcctgggctcccaggacatgcgagaggctttgctg<br>ggctgtctgctgttcattctcagccagcgacactcgccagacgctggggaggcctcaaga<br>gtggaccgcctggagaggagggagaggttaggcccccaaaag***tga***ggccacaagtcctgg<br>cagcagctgtatccacaaaatgctttcttttggagtaggataatcctggcaccagcactg<br>accgaagcctgcccagtggacagaagatatagtgagggttgtgcatgagagggatctgcc<br>acagacatgcctctccactcccaacagaaatgtctttctggaagaatgccttgcatctag<br>cacaaaactgattattgcccctctgtcctccagcagttcctcccaaagaccactcctaat<br>cacctctggcctcaggcgggaggggaactaacacccacccacccctgccctccctgcaaa<br>tgggaacatcaaggttcccagtgcttaactgagggacaagtgacaatttagcagagaggc<br>aagatttgaatccagactgtcttccagactcaggacctaccttaaaataatatctgagtt<br>gcttatggaggcagacctgcctgcaaagcccagcactcagcaagtgctcaataaatattt<br>gatttgaattctttc (SEQ ID NO: 15) |
| Human (-strand, reverse complement) | gaaagaattcaaatcaaatatttattgagcacttgctgagtgctgggctttgcaggcagg<br>tctgcctccataagcaactcagatattattttaaggtaggtcctgagtctggaagacagt<br>ctggattcaaatcttgcctctctgctaaattgtcacttgtccctcagttaagcactggga<br>accttgatgttcccatttgcagggagggcaggggtgggtgggtgttagttcccctcccgc<br>ctgaggccagaggtgattaggagtggtctttgggaggaactgctggaggacagaggggca<br>ataatcagttttgtgctagatgcaaggcattcttccagaaagacatttctgttgggagtg<br>gagaggcatgtctgtggcagatccctctcatgcacaaccctcactatatcttctgtccac<br>tgggcaggcttcggtcagtgctggtgccaggattatcctactccaaaagaaagcattttg<br>tggatacagctgctgccaggacttgtggcctcacttttgggggcctaacctctccctcct<br>ctccaggcggtccactcttgaggcctccccagcgtctggcgagtgtcgctggctgagaat<br>gaacagcagacagcccagcaaagcctctcgcatgtcctgggagcccaggcggcgggccaa<br>tcggcgcagcaggggcaggaggtattggcgggccaggcgggcagcaggcagcagcaggca<br>ggacagcagcaatcgaagcagcagcgggagcagtggcgtgggcatggcagggccagtgag<br>tcagtgcCTGGGAAGACAACACAGACTTTAGGCTTGCATGTCCTGGTTCTGCCTCACCTG<br>GCAAGGACATGGGGTGGGCAGGAGTTCCCCCTCCCTTCAGTTTACACCTTCCTGCTCCTG<br>ACCTCAATTTGTAGGTCATTTTTGCTTTCATGAAGCCCTTTCTCTTGGCAAGGCAGCTGA<br>GGCAGGAAGGTTCTCACCATAGCACAGATGGGGAGACTGAACCAAGGCAAGAGTAAACCA<br>AGACCTACAGCTTGCCGTTCCCAGCTCCAGGCATTCCTACTGCTCCCTGGCCCCTCCCTT<br>CCTCTAGTCACCCCCTCCTCTTGCACAGCCTCAATGCCCCTGGAGTTCCCTAACCCTTCT<br>CCCTCAGTCTAGCAGGAGTTCTTCTCCAGGCAATTCTCAATTTTTCTTTTGGGGCTCCTG<br>ATCCACCCTGACCTGACACTCCCTGACCTCTCAGTCCCCTACccccaccaatccacggca<br>gctctcaccgggcag (SEQ ID NO: 16) |
| Mouse (+strand) | ccaataacaacacactgtcctcgtttattgactacctgctgcgtaccaagctttgaaagt<br>actcattctttaacgggaagcaagggcttataattttaaggtagacgggacagtttggat<br>ttaaataccacctcttagctaaattgtcttgagtctaagtgaaacatcatctcttaactg<br>accttgatacccgcatttgcaggtccaccctggaggccagagataaggcagagggagctg<br>cagagaggaagggtcaatcaacacaatctgtagcctgctaggagctaggggagtgggaac<br>tgttcaggtcagagccctcttgcactcagcccggactgtcttcgcccactgggcagtctg<br>ccgtccatgcccgtgcgtgcggaccgacgcctggactaaccggctccaaaagtactttga<br>tgggcgttgctgtttccaggacccgtggcctcacttctgggggcccaatctctccttcct<br>ctgggagtggtccactctggaggcctctccagaatccggtggctgttgctggctgaggac<br>aaagagcagacagctcagcagagcctctctcatgtcttgggagctcagtcggcgggccag<br>ccggcgcagcaagggcaggaggtgctgccgggccaggcgggcaacaggcagcagcaggcg<br>ggacagcagcgatcgaagcaccatcgggagcaatggaacgggcatggcaggacctgcacC<br>TGCAAAGGGAACCCGGGTTTTAGACTGTACCTCAGGCACGCACCTCACCTGGCAAAGCAG<br>GGTGCGGGGGTGTGGAGTCCTCCCTTCAGCTTATACctctgtactccccagttttcaact |

TABLE 1C-continued

| (exons in lowercase) - Myomerger | |
|---|---|
| Source | Genomic nucleic acid sequence |
| | ggattagttttacagtgcagctttcttctggcatgaaagctggttaaggagttcactcac<br>tgttatcacagatgggaagggagcccagggctggaaggtggtggggactGAGGCTAGGGC<br>CTTTTCCAGAACCCACTTCCTTTAATCCCTCCCTCCCTTTGCATACTCTGACctgaagcc<br>tgaacttcttgccctcctgctcaccagttctaaccggccagtggcagctctcaccagtca<br>gaactgctcagaatcaatttcaggatgcttttgcctgcggtggattcagcatcact<br>(SEQ ID NO: 17) |
| Mouse (-strand, reverse complement) - start codon is bold & underlined; stop codon is bold and italicized | agtgatgctgaatccaccgcaggcaaaagcatcctgaaattgattctgagcagttctgac<br>tggtgagagctgccactggccggttagaactggtgagcaggagggcaagaagttcaggct<br>tcagGTCAGAGTATGCAAAGGGAGGGAGGGATTAAAGGAAGTGGGTTCTGGAAAAGGCCC<br>TAGCCTCagtccccaccaccttccagccctgggctcccttcccatctgtgataacagtga<br>gtgaactccttaaccagctttcatgccagaagaaagctgcactgtaaaactaatccagtt<br>gaaaactggggagtacagagGTATAAGCTGAAGGGAGGACTCCACACCCCCGCACCCTGC<br>TTTGCCAGGTGAGGTGCGTGCCTGAGGTACAGTCTAAAACCCGGGTTCCCTTTGCAGgtg<br>caggtcctgcc**<u>atg</u>**cccgttccattgctcccgatggtgcttcgatcgctgctgtcccgcc<br>tgctgctgcctgttgcccgcctggcccggcagcacctcctgcccttgctgcgccggctgg<br>cccgccgactgagctcccaagacatgagagaggctctgctgagctgtctgctctttgtcc<br>tcagccagcaacagccaccggattctggagaggcctccagagtggaccactcccagagga<br>aggagagattgggcccccagaag***tga***ggccacgggtcctggaaacagcaacgcccatcaa<br>agtacttttggagccggttagtccaggcgtcggtccgcacgcacgggcatggacggcaga<br>ctgcccagtgggcgaagacagtccgggctgagtgcaagagggctctgacctgaacagttc<br>ccactcccctagctcctagcaggctacagattgtgttgattgacccttcctctctgcagc<br>tccctctgccttatctctggcctccagggtggacctgcaaatgcgggtatcaaggtcagt<br>taagagatgatgtttcacttagactcaagacaatttagctaagaggtggtatttaaatcc<br>aaactgtcccgtctaccttaaaattataagcccttgcttcccgttaaagaatgagtactt<br>tcaaagcttggtacgcagcaggtagtcaataaacgaggacagtgtgttgttattgg<br>(SEQ ID NO: 18) |

Nonlimiting examples of extracellular wt-myomerger polypeptides are found in Table 1D. In other embodiments, the extracellular myomerger polypeptide has at least one amino acid modification relative to an extracellular wt-myomerger polypeptide. An extracellular wt-myomerger polypeptide can, in some embodiments, be an extracellular myomerger polypeptide from any animal including but not limited to a mammal, a rat, a cat, a rabbit, a human, a cow, a chicken, a turkey, a monkey, a tree shrew, a dog, a pig, a shrew, an elephant, or an opossum. Related nucleic acid molecules (e.g., cDNA or genomic DNA) can be any suitable nucleic acid molecule including but not limited to those made from appropriate changes (e.g., deletions or codon changes to make the same amino acid) to the nucleic acid molecules in Tables 1B and 1C.

TABLE 1D

| Extracellular Myomerger | |
|---|---|
| Source | Polypeptide sequences |
| Mouse | RQHLLPLLRRLARRLSSQDMREALLSCLLFVLSQQQPPDSGEASRVDHS<br>QRKERLGPQK (SEQ ID NO: 19) |
| Human | RQYLLPLLRRLARRLGSQDMREALLGCLLFILSQRHSPDAGEASRVDRL<br>ERRERLGPQK (SEQ ID NO: 20) |
| Cat | RRHLLPLLRRLARRLGSQDVREALLGCLLFILSQSRPPDAEEVSRVAGQE<br>RRERLAPPK (SEQ ID NO: 21) |
| Rabbit | RRHLLPLLRRLAQRLGSQGTREALLGCLLFVLSQRQPPDASGEASRVDP<br>PERKERLGRQK (SEQ ID NO: 22) |
| Dog | RRHLLPLLRGLARRLGSQEVREALLGCLLFILSQRHPPDAEEASRVAGQ<br>ERKERLAPPK (SEQ ID NO: 23) |
| Elephant | RQHLLPLLRRLARRLGSQDMRQALLGCLLFVLSQQHPPDAGEASREALS<br>ERRGRLAPQK (SEQ ID NO: 24) |

One or more modifications, in some instances, can include an insertion, a deletion, a substitution, or combinations thereof. In certain embodiments, one or more modifications to a wt-myomerger polypeptide or extracellular wt-myomerger polypeptide can comprise an insertion, such, but not limited to an insertion at the C-terminus or at the N-terminus of the wt-myomerger polypeptide or extracellular wt-myomerger polypeptide. In some examples of the embodiments, an insertion can include (e.g., at the C-terminus, at the N-terminus, or at another place in the polypeptide) about 1, about 2, about 3, about 4, about 5, about 6, about 7, about 8, about 9, about 10, about 11, about 12, about 13, about 14, about 15, about 16, about 17, about 18, about 19, or about 20 amino acids (e.g., natural amino acids, or modified or unusual amino acids).

In some embodiments, the inventive polypeptide does not encompass one or more naturally occurring polypeptides (e.g., does not encompass one or more of the wt-myomerger polypeptides). In other embodiments, the inventive polypeptide does not encompass any of the wt-myomerger polypeptides. In other embodiments, the inventive polypeptide does not encompass any of the extracellular wt-myomerger polypeptide. In some embodiments, the inventive polypeptide does not encompass any naturally occurring polypeptide (e.g., does not encompass any of the wt-myomerger polypeptides or any other naturally occurring polypeptide).

In some embodiments, one or more modifications to a wt-myomerger polypeptide can include one or more substitutions, one or more insertions, or one or more deletions (or combinations thereof) to one or more amino acids in a hydrophobic region of a wt-myomerger polypeptide, in a signal region of a wt-myomerger polypeptide, in a transmembrane region of a wt-myomerger polypeptide, or in a combination thereof. In some embodiments, one or more modifications to a wt-myomerger polypeptide can include one or more substitutions or one or more deletions (or combinations thereof) to one or more amino acids in a hydrophobic region of a wt-myomerger polypeptide, in a signal region of a wt-myomerger polypeptide, in a transmembrane region of a wt-myomerger polypeptide, or in a combination thereof.

In some embodiments, the myomerger polypeptide can have a polypeptide sequence with an amino acid sequence identity to a wt-myomerger polypeptide (e.g., SEQ ID NO:1, SEQ ID NO:2, SEQ ID NO:3, SEQ ID NO:4, SEQ ID NO:5, SEQ ID NO:6, or SEQ ID NO:7) of about 70%, about 75%, about 80%, about 85%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, about 99.9%, about 99.95%, about 99.99%, less than about 100%, at least about 70%, at least about 80%, at least about 90%, at least about 95%, at least about 99%, or at least about 99.5%. In some embodiments, the myomerger polypeptide sequence has an amino acid sequence identity to SEQ ID NO:1, SEQ ID NO:2, SEQ ID NO:3, SEQ ID NO:4, SEQ ID NO:5, SEQ ID NO:6, or SEQ ID NO:7 of about 70%, about 75%, about 80%, about 85%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, about 99.9%, about 99.95%, about 99.99%, less than about 100%, at least about 70%, at least about 80%, at least about 90%, at least about 95%, at least about 99%, or at least about 99.5%. The amino acid sequence identity (e.g., percent identity) can be determined by any suitable method, such as using BLAST, BLAST-2, ALIGN, ALIGN-2, Clustal Omega, or Megalign software. Unless otherwise indicated, the amino acid sequence identity (e.g., percent identity) is determined using BLAST-2.

In some embodiments, the myomerger polypeptide has (e.g., as compared to a wt-myomerger polypeptide or as compared to the absence of a myomerger polypeptide) an increased ability to permeabilize membranes, an increased ability to form pores in membranes, an increase in the ability to stress membranes, an increase in the ability to lyse cells or liposomes, an increased ability to activate fusion, a decreased ability to activate fusion, an increased ability to confer fusogenicity, a decreased ability to confer fusogenicity, an increased level of expression during embryonic development, a decreased level of expression during embryonic development, an increased level of expression during myogenesis in adult organisms (e.g., older than embryonic), a decreased level of expression during myogenesis in adult organisms (e.g., older than embryonic), an increased level of induction of myogenesis in adult organisms (e.g., older than embryonic), a decreased of induction of myogenesis in adult organisms (e.g., older than embryonic), an increased affinity for membranes, a decreased affinity for membranes, an increased level of association with membrane compartment, a decreased level association with membrane compartment, or combinations thereof. In other embodiments, the myomerger polypeptide has (e.g., as compared to a wt-myomerger polypeptide or as compared to the absence of a myomerger polypeptide) an increased ability to permeabilize membranes, an increased ability to form pores in membranes, an increase in the ability to stress membranes, an increase in the ability to lyse cells or liposomes, an increased ability to activate fusion, an increased ability to confer fusogenicity, an increased level of expression during embryonic development, an increased level of expression during myogenesis in adult organisms (e.g., older than embryonic), an increased level of induction of myogenesis in adult organisms (e.g., older than embryonic), an increased affinity for membranes, an increased level of association with membrane compartment, or combinations thereof.

Some embodiments of the invention include nucleic acid molecules that can encode for the myomerger polypeptide ("myomerger nucleic acid molecules"). In certain embodiments, the myomerger nucleic acid molecule is included in a vector (e.g., a viral vector, a retroviral vector, a lentiviral vector, an adenoviral vector, an adeno-associated viral vector, a herpesviral vector, a chimeric viral vector, a plasmid, a cosmid, an artificial chromosome, a bacteriophage, an animal virus, a plant virus, an expression vector, a conjugative vector, or a nonconjugative vector). In certain embodiments, the myomerger nucleic acid molecule is in a cell, such as an insect cell (e.g., an Sf9 cell) or a mammalian cell (e.g., a human cell, a rat cell a mouse cell, a muscle cell, a non-muscle cell, a myoblast, a fibroblast, a C2C12 cell, a 10T ½ fibroblast, an NIH/3T3 cell, a CHO cell, a mesenchymal stem cell (MSC), a hematopoietic stem cell, a blood cell, a bone marrow cell, or an adipose stem cell).

In other embodiments, the myomerger nucleic acid molecule comprises one or more nucleic acid sequences that are not used to encode for the inventive polypeptide (e.g., one or more introns). For example, the myomerger nucleic acid molecule can comprise a nucleic acid sequence as found in nature (e.g., including introns). In certain embodiments, the myomerger nucleic acid molecule differs from the one or more nucleic acid molecules in nature because the myomerger nucleic acid molecule does not include one or more introns. In some embodiments, the myomerger nucleic acid molecule is a cDNA molecule ("myomerger cDNA molecule"). In certain embodiments, the myomerger cDNA molecule is identical to a nucleic acid molecule found in nature. In other embodiments, the myomerger cDNA molecule is not identical to a nucleic acid molecule found in nature (e.g., due to the myomerger cDNA molecule not including one or more introns in the nucleic acid molecule found in nature).

In some embodiments, the myomerger nucleic acid molecule sequence has a sequence identity to a nucleic acid molecule encoding a wt-myomerger polypeptide (e.g., SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, or SEQ ID NO:18) of about 60%, about 70%, about 80%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, about 99.9%, about 99.95%, about 99.99%, less than about 100%, at least about 60%, at least about 70%, at least about 80%, at least about 90%, at least about 95%, at least about 99%, or at least about 99.5%. In some embodiments, the myomerger nucleic acid molecule sequence has a sequence identity to SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, or SEQ ID NO:18 of about 60%, about 70%, about 80%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, about 99.9%, about 99.95%, about 99.99%, less than about 100%, at least about 60%, at least about 70%, at least about 80%, at least about 90%, at least about 95%, at least about 99%, or at least about 99.5%. Nonlimiting examples of wt-myomerger polypeptides and wt-myomerger nucleic acid molecules can be found in Table 1. The nucleic acid sequence identity (e.g., percent identity) can be determined by any suitable method, such as using BLAST, BLAST-2, ALIGN, ALIGN-2, Clustal Omega, or Megalign software. Unless otherwise indicated, the nucleic acid sequence identity (e.g., percent identity) is determined using BLAST-2.

In some embodiments, the myomerger nucleic acid molecule encodes for an inventive polypeptide that has one or more modifications to wt-myomerger polypeptide in a hydrophobic region, in a signal region, in a transmembrane region, or in a combination thereof.

The myomerger nucleic acid molecule can be made using any suitable technique, such as but not limited to, chemical synthesis, enzymatic production or biological production. Chemical synthesis of a nucleic acid molecule can include, for example, a nucleic acid molecule made by in vitro chemical synthesis using phosphotriester, phosphite or phosphoramidite chemistry and solid phase techniques, or via deoxynucleoside H-phosphonate intermediates. Enzymatically produced nucleic acid molecules can be accomplished using any suitable method including but not limited to Polymerase Chain Reaction (PCR). Biologically produced nucleic acid molecules can be accomplished using any suitable method including but not limited to a recombinant nucleic acid produced (i.e., replicated) in a living cell, such as a recombinant DNA vector replicated in bacteria.

In some embodiments, one or more modifications to an extracellular wt-myomerger polypeptide can include one or more substitutions, one or more insertions, or one or more deletions (or combinations thereof) to one or more amino acids in a hydrophobic region of an extracellular wt-myomerger polypeptide, in a signal region of an extracellular wt-myomerger polypeptide, or in a combination thereof. In some embodiments, one or more modifications to an extracellular wt-myomerger polypeptide can include one or more substitutions or one or more deletions (or combinations thereof) to one or more amino acids in a hydrophobic region of an extracellular wt-myomerger polypeptide, in a signal region of an extracellular wt-myomerger polypeptide, or in a combination thereof.

In other embodiments, the extracellular myomerger polypeptide comprises (a) amino acids 4-15 of any of SEQ ID Nos: 19-24, (b) amino acids 18-32 of any of SEQ ID Nos: 19-24, or (c) both. In other embodiments, the extracellular myomerger polypeptide comprises (a) LLPLLRRLARRL (SEQ ID NO:25), (b) QDMREALLSCLLFVL (SEQ ID NO:26) or QDMREALLGCLLFIL (SEQ ID NO:27), or (c) both.

In some embodiments, the extracellular myomerger polypeptide can have a polypeptide sequence with an amino acid sequence identity to an extracellular wt-myomerger polypeptide (e.g., SEQ ID NO:19, SEQ ID NO:20, SEQ ID NO:21, SEQ ID NO:22, SEQ ID NO:23, and SEQ ID NO:24) of about 70%, about 75%, about 80%, about 85%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, about 99.9%, about 99.95%, about 99.99%, less than about 100%, at least about 70%, at least about 80%, at least about 90%, at least about 95%, at least about 99%, or at least about 99.5%. In some embodiments, the extracellular myomerger polypeptide sequence has an amino acid sequence identity to SEQ ID NO:19, SEQ ID NO:20, SEQ ID NO:21, SEQ ID NO:22, SEQ ID NO:23, and SEQ ID NO:24 of about 70%, about 75%, about 80%, about 85%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, about 99.9%, about 99.95%, about 99.99%, less than about 100%, at least about 70%, at least about 80%, at least about 90%, at least about 95%, at least about 99%, or at least about 99.5%. The amino acid sequence identity (e.g., percent identity) can be determined by any suitable method, such as using BLAST, BLAST-2, ALIGN, ALIGN-2, Clustal Omega, or Megalign software. Unless otherwise indicated, the amino acid sequence identity (e.g., percent identity) is determined using BLAST-2.

In some embodiments, the extracellular myomerger polypeptide has (e.g., as compared to a wt-myomerger polypeptide or an extracellular wt-myomerger polypeptide, or as compared to the absence of a myomerger polypeptide or an extracellular wt-myomerger polypeptide) an increased ability to permeabilize membranes, an increased ability to form pores in membranes, an increase in the ability to stress membranes, an increase in the ability to lyse cells or liposomes, an increased ability to activate fusion, a decreased ability to activate fusion, an increased ability to confer fusogenicity, a decreased ability to confer fusogenicity, an increased level of expression during embryonic development, a decreased level of expression during embryonic development, an increased level of expression during myogenesis in adult organisms (e.g., older than embryonic), a decreased level of expression during myogenesis in adult organisms (e.g., older than embryonic), an increased level of induction of myogenesis in adult organisms (e.g., older than embryonic), a decreased of induction of myogenesis in adult organisms (e.g., older than embryonic), an increased affinity for membranes, a decreased affinity for membranes, an increased level of association with membrane compartment, a decreased level association with membrane compartment, or combinations thereof. In other embodiments, the extracellular myomerger polypeptide has (e.g., as compared to a wt-myomerger polypeptide or an extracellular wt-myomerger polypeptide, or as compared to the absence of a myomerger polypeptide or an extracellular myomerger polypeptide) an increased ability to permeabilize membranes, an increased ability to form pores in membranes, an increase in the ability to stress membranes, an increase in the ability to lyse cells or liposomes, an increased ability to activate fusion, an increased ability to confer fusogenicity, an increased level of expression during embryonic development, an increased level of expression during myogenesis in adult organisms (e.g., older than embryonic), an increased level of induction of myogenesis in adult organisms (e.g., older than embryonic), an increased affinity for membranes, an increased level of association with membrane compartment, or combinations thereof.

Some embodiments of the invention include nucleic acid molecules that can encode for an extracellular myomerger polypeptide ("extracellular myomerger nucleic acid molecules"). In certain embodiments, the extracellular myomerger nucleic acid molecule is included in a vector (e.g., a viral vector, a retroviral vector, a lentiviral vector, an adenoviral vector, an adeno-associated viral vector, a herpesviral vector, a chimeric viral vector, a plasmid, a cosmid, an artificial chromosome, a bacteriophage, an animal virus, a plant virus, an expression vector, a conjugative vector, or a nonconjugative vector). In certain embodiments, the extracellular myomerger nucleic acid molecule is in a cell, such as an insect cell (e.g., an Sf9 cell) or a mammalian cell (e.g., a human cell, a rat cell a mouse cell, a muscle cell, a non-muscle cell, a myoblast, a fibroblast, a C2C12 cell, a 10T ½ fibroblast, an NIH/3T3 cell, a CHO cell, a mesenchymal stem cell (MSC), a hematopoietic stem cell, a blood cell, a bone marrow cell, or an adipose stem cell).

In other embodiments, the extracellular myomerger nucleic acid molecule comprises one or more nucleic acid sequences that are not used to encode for the inventive polypeptide (e.g., one or more introns). For example, the extracellular myomerger nucleic acid molecule can comprise a nucleic acid sequence as found in nature (e.g., including introns). In certain embodiments, the extracellular myomerger nucleic acid molecule differs from the one or more nucleic acid molecules in nature because the extracellular myomerger nucleic acid molecule does not include one or more introns. In some embodiments, the extracellular myomerger nucleic acid molecule is a cDNA molecule ("myomerger cDNA molecule"). In certain embodiments, the extracellular myomerger cDNA molecule is identical to a nucleic acid molecule found in nature. In other embodiments, the extracellular myomerger cDNA molecule is not identical to a nucleic acid molecule found in nature (e.g., due to the myomerger cDNA molecule not including one or more introns in the nucleic acid molecule found in nature).

In some embodiments, the extracellular myomerger nucleic acid molecule sequence has a sequence identity to a nucleic acid molecule encoding an extracellular wt-myomerger polypeptide (e.g., see Table 1B and 1C, which can include changes to provide appropriate cDNA sequences or equivalent genomic-like sequences) of about 60%, about 70%, about 80%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, about 99.9%, about 99.95%, about 99.99%, less than about 100%, at least about 60%, at least about 70%, at least about 80%, at least about 90%, at least about 95%, at least about 99%, or at least about 99.5%. Nonlimiting examples of extracellular wt-myomerger polypeptides and wt-myomerger nucleic acid molecules can be found in Table 1. The nucleic acid sequence identity (e.g., percent identity) can be determined by any suitable method, such as using BLAST, BLAST-2, ALIGN, ALIGN-2, Clustal Omega, or Megalign software. Unless otherwise indicated, the nucleic acid sequence identity (e.g., percent identity) is determined using BLAST-2.

In some embodiments, the extracellular myomerger nucleic acid molecule encodes for an inventive polypeptide that has one or more modifications to extracellular wt-myomerger polypeptide in a hydrophobic region, in a signal region, or in a combination thereof.

The extracellular myomerger nucleic acid molecule can be made using any suitable technique, such as but not limited to, chemical synthesis, enzymatic production or biological production. Chemical synthesis of a nucleic acid molecule can include, for example, a nucleic acid molecule made by in vitro chemical synthesis using phosphotriester, phosphite or phosphoramidite chemistry and solid phase techniques, or via deoxynucleoside H-phosphonate intermediates. Enzymatically produced nucleic acid molecules can be accomplished using any suitable method including but not limited to Polymerase Chain Reaction (PCR). Biologically produced nucleic acid molecules can be accomplished using any suitable method including but not limited to a recombinant nucleic acid produced (i.e., replicated) in a living cell, such as a recombinant DNA vector replicated in bacteria.

Modifications or changes made in the structure of the nucleic acid molecules and/or polypeptides of the present invention are encompassed within some embodiments of the present invention. In certain embodiments, a polypeptide can be modified (e.g., by one or more insertions, one or more deletions, or one or more substitutions (e.g., conservative substitutions)). In some embodiments, the polypeptide which was modified does not have an appreciable loss (e.g., a decrease in a function of less than about 1%, less than about 5%, less than about 10%, less than about 25%, less than about 50%, less than about 75%, less than about 90%, less than about 95%, less than about 99%, or less than about 100%) of one or more chosen functions of the unmodified polypeptide such as, for example, the ability to permeabilize membranes, the ability to form pores in membranes, the ability to stress membranes, the ability to lyse cells or liposomes, the ability to make changes to the cytoskeleton of the cell (e.g., reorganizing the cytoskeleton, rearranging the cytoskeleton, making changes to the cytoskeleton to allow the cell to fuse), the ability to activate fusion of two cells, the ability to make a cell fusion capable (e.g., a protein confers fusion capable properties to a cell if upon adding the protein, the cell is capable of fusing to another cell if that other cell comprises myomaker and myomerger), the ability to confer fusogenicity to a cell (e.g., a protein confers fusogenic properties to a cell if upon adding the protein, the cell will fuse with another cell if that other cell comprises myomaker), the level of expression during embryonic development, the level of expression during myogenesis in adult organisms (e.g., older than embryonic), the level of induction of myogenesis in adult organisms (e.g., older than embryonic), the affinity for membranes, or the level of association with membrane compartment. In some embodiments, the polypeptide which was modified retains desired levels (e.g., at least about 20%, at least about 40%, at least about 50%, at least about 75%, at least about 80%, at least about 90%, at least about 95%, or at least about 99%) of one or more functions of the unmodified polypeptide, such as, for example, the ability to permeabilize membranes, the ability to form pores in membranes, the ability to stress membranes, the ability to lyse cells or liposomes, the ability to make changes to the cytoskeleton of the cell (e.g., reorganizing the cytoskeleton, rearranging the cytoskeleton, making changes to the cytoskeleton to allow the cell to fuse), the ability to activate fusion of two cells, the ability to make a cell fusion capable (e.g., a protein confers fusion capable properties to a cell if upon adding the protein, the cell is capable of fusing to another cell if that other cell comprises myomaker and myomerger), the ability to confer fusogenicity to a cell (e.g., a protein confers fusogenic properties to a cell if upon adding the protein, the cell will fuse with another cell if that other cell comprises myomaker), the level of expression during embryonic development, the level of expression during myogenesis in adult organisms (e.g., older than embryonic), the level of induction of myogenesis in adult organisms (e.g., older than embryonic), the affinity for membranes, or the level of association with membrane compartment. In some embodiments, the polypeptide after modification has an increased level of one or more functions as compared to the unmodified polypeptide. Nucleic acid molecules can be designed to encode for such a modified polypeptide, and such nucleic acid molecules are encompassed by the present invention.

A "functional polypeptide" is defined as a polypeptide (e.g., a myomerger polypeptide, an extracellular myomerger polypeptide, or a modified extracellular myomerger polypeptide) that has desired levels (e.g., at least about 20%, at least about 40%, at least about 50%, at least about 75%, at least about 80%, at least about 90%, at least about 95%, or at least about 99%, as compared to another polypeptide, such as a naturally occurring polypeptide) of one or more functions such as, for example, the ability to increase permeability of membranes, the ability to form pores in membranes, the ability to stress membranes, the ability to lyse cells or liposomes, the ability to make changes to the cytoskeleton of the cell (e.g., reorganizing the cytoskeleton, rearranging the cytoskeleton, making changes to the cytoskeleton to allow the cell to fuse), the ability to activate fusion of two cells, the ability to make a cell fusion capable (e.g., a protein confers fusion capable properties to a cell if upon adding the protein, the cell is capable of fusing to another cell if that other cell comprises myomaker and myomerger), the ability to confer fusogenicity to a cell (e.g., a protein confers fusogenic properties to a cell if upon adding the protein, the cell will fuse with another cell if that other cell comprises myomaker), the level of expression during embryonic development, the level of expression during myogenesis in adult organisms (e.g., older than embryonic), the level of induction of myogenesis in adult organisms (e.g., older than embryonic), the affinity for membranes, or the level of association with membrane compartment. In some embodiments, the function polypeptide has an increased level of one or more functions as compared to another polypeptide (e.g., a naturally occurring polypeptide). Nucleic acid molecules can be designed to encode for functional polypeptides, and such nucleic acid molecules are encompassed by the present invention.

A "functionally equivalent" polypeptide (e.g., a modified myomerger polypeptide or a modified extracellular myomerger polypeptide) is defined as a polypeptide that has been modified (e.g., by one or more insertions, one or more deletions, or one or more substitutions (e.g., conservative substitutions)) from an original polypeptide (e.g., a wt-myomerger polypeptide) and that modified polypeptide retains desired levels (e.g., at least about 20%, at least about 40%, at least about 50%, at least about 75%, at least about 80%, at least about 90%, at least about 95%, or at least about 99%) of one or more functions of the original polypeptide, such as, for example, the ability to increase permeability of membranes, the ability to form pores in membranes, the ability to stress membranes, the ability to lyse cells or liposomes, the ability to make changes to the cytoskeleton of the cell (e.g., reorganizing the cytoskeleton, rearranging the cytoskeleton, making changes to the cytoskeleton to allow the cell to fuse), the ability to activate fusion of two cells, the ability to make a cell fusion capable (e.g., a protein confers fusion capable properties to a cell if upon adding the protein, the cell is capable of fusing to another cell if that other cell comprises myomaker and myomerger), the ability to confer fusogenicity to a cell (e.g., a protein confers fusogenic properties to a cell if upon adding the protein, the cell will fuse with another cell if that other cell comprises myomaker), the level of expression during embryonic development, the level of expression during myogenesis in adult organisms (e.g., older than embryonic), the level of induction of myogenesis in adult organisms (e.g., older than embryonic), the affinity for membranes, or the level of association with membrane compartment. In some embodiments, the functionally equivalent polypeptide has an increased level of one or more functions compared to the original polypeptide. Nucleic acid molecules can be designed to encode for functionally equivalent polypeptides, and such nucleic acid molecules are encompassed by the present invention.

In certain embodiments, the shorter the length of a polypeptide, the fewer the modifications (e.g., substitutions) that can be made within the polypeptide while retaining, for example, a desired level of a chosen function. In some instances, longer domains can have a greater number of such changes while retaining, for example, a desired level of a chosen function. In other embodiments, a full-length polypeptide can have more tolerance for a fixed number of changes while retaining, for example, a desired level of a chosen function, as compared to a shorter length of that polypeptide.

The design of substitutions can take many forms, including but not limited to those described herein. In some embodiments, the hydropathic index of amino acids may be considered in designing substitutions. In the hydropathic index, each amino acid is assigned a hydropathic index on the basis of their hydrophobicity or charge characteristics, as follows: isoleucine (+4.5); valine (+4.2); Leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); or arginine (−4.5). In some instances, certain amino acids may be substituted for other amino acids having a similar hydropathic index. In making changes based upon the hydropathic index, the substitution of amino acids with hydropathic indices can be made with amino acids that have an index difference of no more than ±2, no more than ±1, or no more than ±0.5.

In some embodiments, substitutions can also be made based on hydrophilicity values. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids with hydrophilicity values can be made with amino acids that have a value of no more than ±2, no more than ±1, or no more than ±0.5.

A "conservative substitution" in an amino acid sequence or polypeptide indicates that a given amino acid residue is replaced by a residue having similar physiochemical characteristics (e.g., no more than ±1 when based on hydropathic index or no more than ±1 when base on hydrophilicity values). Examples of conservative substitutions include (a) substitution of one aliphatic residue for another with an aliphatic residue, (b) substitution of one of Ile, Val, Leu, or Ala for one another of Ile, Val, Leu, or Ala, (c) substitution of one of Gly, Ile, Val, Leu, or Ala for one another of Gly, Ile, Val, Leu, or Ala, (d) substitution of one polar residue for another polar residue, (e) substitution of one of Lys and Arg with another of Lys and Arg, (f) substitution of one of Glu and Asp with another of Glu and Asp, (g) substitution of one of Gln and Asn with another of Gln and Asn, (h) substitution of one hydroxyl or sulfur containing residue with another hydroxyl or sulfur containing residue, (i) substitution of one of Ser, Cys, Thr, or Met with another of Ser, Cys, Thr, or Met, (j) substitution of one aromatic residue for another with an aromatic residue, (k) substitution of one of Phe, Tyr, or Trp with another of Phe, Tyr, or Trp, (l) substitution of one basic residue for another basic residue, (m) substitution of one of His, Lys, or Arg with another of His, Lys, or Arg, (n) substitution of an acidic/amide residue with another acidic/amide residue, (o) substitution of one of Asp, Glu, Asn, or Gln with another of Asp, Glu, Asn, or Gln, (p) substitution of a residue with another residue of a similar size, and (q) substitution of one of Ala, Gly, or Ser with another of Ala, Gly, or Ser. In some embodiments, each amino acid in a hydrophobic region of a polypeptide can be substituted with conservative substitutions (e.g., any combination of conservative substitutions relating to hydrophobic residues).

While discussion has focused on amino acid changes, it will be appreciated that these changes may occur by alteration of the encoding DNA; taking into consideration also that the genetic code is degenerate and that two or more codons may code for the same amino acid. A table of amino acids and their codons is presented below for use in such embodiments, as well as for other uses, such as in the design of probes and primers and the like.

TABLES A and B

| Amino acid designations and codon table | | | |
|---|---|---|---|
| Table A-Amino Acid Designations | | | Table B-Codons for Amino Acids |
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

The term "functionally equivalent codon" is used herein to refer to codons that encode the same amino acid, such as the six codons for arginine or serine.

In certain instances, the nucleic acid molecule can be engineered to contain distinct sequences while at the same time retaining the capacity to encode a desired inventive polypeptide. In some embodiments, this can be accomplished owing to the degeneracy of the genetic code (i.e., the presence of multiple codons) which encode for the same amino acids. In other instances, it can be accomplished by including, adding, or excluding introns in the nucleic acid molecule.

In certain embodiments, a restriction enzyme recognition sequence can be introduced into a nucleic acid sequence while maintaining the ability of that nucleic acid molecule to encode a desired polypeptide. In other embodiments, a CRISPR system (e.g., a CRISPR system comprising one or more of guide RNA, crRNA, tracrRNA, sgRNA, DNA repair template, and Cas protein, such as but not limited to CRISPR/Cas9) can be used to introduce a nucleic acid molecule while maintaining the ability of that nucleic acid molecule to encode a desired polypeptide.

It will also be understood that amino acid sequences (e.g., polypeptides) and nucleic acid sequences may include additional residues, such as additional N- or C-terminal amino acids or 5' or 3' sequences, and yet still be essentially as set forth in one of the sequences disclosed herein, so long as the sequence meets the criteria set forth above, such as including the maintenance of biological activity where polypeptide expression is concerned. The addition of terminal sequences particularly applies to nucleic acid sequences that may, for example, include various non-coding sequences flanking either of the 5' or 3' portions of the coding region or may include various internal sequences, (i.e., introns) which can occur within genes.

Some embodiments of the present invention rely on or use synthesis of polypeptides in cyto, via transcription and translation of appropriate nucleic acid molecules (e.g., nucleic acid sequences as discussed herein). These polypeptides will include the twenty "natural" amino acids, and post-translational modifications thereof. In vitro peptide synthesis permits the use of modified or unusual amino acids. In some embodiments, the inventive polypeptide encompasses modifications (e.g., one or more substitutions or one or more insertions) that include one or more modified or unusual amino acids. A table of exemplary, but not limiting, modified or unusual amino acids is provided in Table C.

TABLE C

| Modified or Unusual Amino Acids | |
|---|---|
| Abbr. | Amino Acid |
| Aad | 2-Aminoadipic acid |
| BAad | 3-Aminoadipic acid |
| BAla | beta-alanine, beta-Amino-propionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| BAib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| AHyl | allo-Hydroxylysine |
| 3Hyp | 3-Hydroxyproline |
| 4Hyp | 4-Hydroxyproline |
| Ide | Isodesmosine |

TABLE C-continued

| Modified or Unusual Amino Acids | |
|---|---|
| Abbr. | Amino Acid |
| Aile | allo-Isoleucine |
| MeGly | N-Methylglycine, sarcosine |
| Melle | N-Methylisoleucine |
| MeLys | 6-N-Methyllysine |
| MeVal | N-Methylvaline |
| Nva | Norvaline |
| Nle | Norleucine |
| Orn | Ornithine |

The presently disclosed subject matter further includes a method of producing an inventive polypeptide (e.g., a myomerger polypeptide or an extracellular myomerger polypeptide). Any suitable method can used to make the inventive polypeptides including but not limited to expression through any suitable molecular biological technique (e.g., using a prokaryotic or eukaryotic expression system), isolation from a source in nature, or chemical synthesis. Eukaryotic expression systems include plant-based systems; insect cell systems via recombinant baculoviruses; whole insect systems via recombinant baculoviruses; genetically engineered yeast systems, including but not limited to *Saccharomyces* sp. and Picchia spp.; and mammalian cell systems, including but not limited to C2C12 cells, 10T ½ fibroblasts, NIH/3T3 fibroblasts, mesenchymal stem cells (MSCs), hematopoietic stem cells, Chinese hamster ovary cells or other cell lines commonly used for industrial scale expression of recombinant proteins. In some embodiments, useful plant-based expression systems can include transgenic plant systems. In some embodiments, useful plant-based expression systems can include transplastomic plant systems.

In some embodiments, a method of producing the inventive polypeptide includes providing a host cell comprising a nucleic acid molecule, as disclosed herein, operatively linked to a promoter operable under conditions whereby the encoded polypeptide is expressed; and recovering the polypeptide from the host cell.

Compositions including Pharmaceutical Compositions

One or more inventive polypeptides (e.g., a myomerger polypeptide or an extracellular myomerger polypeptide) or one or more myomerger nucleic acid molecules or extracellular myomerger nucleic acid molecules (e.g., in the form of a bare nucleic acid molecule, a vector, a virus, a plasmid or any suitable form) can be part of a composition and can be in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, or no more than about 99.99%, from about 0.0001% to about 99%, from about 0.0001% to about 50%, from about 0.01% to about 95%, from about 1% to about 95%, from about 10% to about 90%, or from about 25% to about 75%.

One or more inventive polypeptides (e.g., a myomerger polypeptide or an extracellular myomerger polypeptide) or one or more myomerger nucleic acid molecules or extracellular myomerger nucleic acid molecules (e.g., in the form of a bare nucleic acid molecule, a vector, a virus, a plasmid or any suitable form) can be purified or isolated in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 0.0001% to about 99%, from about 0.0001% to about 50%, from about 0.01% to about 95%, from about 1% to about 95%, from about 10% to about 90%, or from about 25% to about 75%. In some embodiments, isolated or purified means that impurities (e.g., cell components or unwanted solution components if chemically synthesized) were removed by one or more of any suitable technique (e.g., column chromatography, HPLC, centrifugation, fractionation, gel, precipitation, or salting out).

Some embodiments of the present invention include compositions comprising one or more inventive polypeptides (e.g., a myomerger polypeptide or an extracellular myomerger polypeptide) or one or more myomerger nucleic acid molecules or extracellular myomerger nucleic acid molecules (e.g., in the form of a bare nucleic acid molecule, a vector, a virus, a plasmid or any suitable form). In certain embodiments, the composition is a pharmaceutical composition, such as compositions that are suitable for administration to animals (e.g., mammals, primates, monkeys, humans, canine, porcine, mice, rabbits, or rats). In some embodiments, there may be inherent side effects (e.g., it may harm the patient or may be toxic or harmful to some degree in some patients).

In some embodiments, one or more inventive polypeptides (e.g., a myomerger polypeptide or an extracellular myomerger polypeptide) or one or more myomerger nucleic acid molecules or extracellular myomerger nucleic acid molecules (e.g., in the form of a bare nucleic acid molecule, a vector, a virus, a plasmid or any suitable form) can be part of a pharmaceutical composition and can be in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 0.001% to about 99%, from about 0.001% to about 50%, from about 0.1% to about 99%, from about 1% to about 95%, from about 10% to about 90%, or from about 25% to about 75%.

In some embodiments, the pharmaceutical composition can be presented in a dosage form which is suitable for the topical, subcutaneous, intrathecal, intraperitoneal, oral, parenteral, rectal, cutaneous, nasal, vaginal, or ocular administration route. In other embodiments, the pharmaceutical composition can be presented in a dosage form which is suitable for parenteral administration, a mucosal administration, intravenous administration, subcutaneous administration, topical administration, intradermal administration, oral administration, sublingual administration, intranasal administration, or intramuscular administration. The pharmaceutical composition can be in the form of, for example, tablets, capsules, pills, powders granulates, suspensions, emulsions, solutions, gels (including hydrogels), pastes, ointments, creams, plasters, drenches, delivery devices, suppositories, enemas, injectables, implants, sprays, aerosols or other suitable forms.

In some embodiments, the pharmaceutical composition can include one or more formulary ingredients. A "formulary ingredient" can be any suitable ingredient (e.g., suitable for the drug(s), for the dosage of the drug(s), for the timing of release of the drugs(s), for the disease, for the disease state, for the organ, or for the delivery route) including, but not limited to, water (e.g., boiled water, distilled water, filtered water, pyrogen-free water, or water with chloroform), sugar (e.g., sucrose, glucose, mannitol, sorbitol, xylitol, or syrups made therefrom), ethanol, glycerol, glycols (e.g., propylene glycol), acetone, ethers, DMSO, surfactants (e.g., anionic surfactants, cationic surfactants, zwitterionic surfactants, or nonionic surfactants (e.g., polysorbates)), oils (e.g., animal oils, plant oils (e.g., coconut oil or *arachis* oil), or mineral oils), oil derivatives (e.g., ethyl oleate, glyceryl monostearate, or hydrogenated glycerides), excipients, preservatives (e.g., cysteine, methionine, antioxidants (e.g., vitamins (e.g., A, E, or C), selenium, retinyl palmitate, sodium citrate, citric acid, chloroform, or parabens, (e.g., methyl paraben or propyl paraben)), or combinations thereof. In some embodiments, the concentration of any individual formulary ingredient in a composition (e.g., pharmaceutical composition) can be in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 0.001% to about 99%, from about 0.001% to about 50%, from about 0.1% to about 99%, from about 1% to about 95%, from about 10% to about 90%, or from about 25% to about 75%. In some embodiments, the concentration of at least one formulary ingredient is not that same as that found in the natural system in which inventive polypeptide (e.g., wt-myomerger polypeptide or extracellular wt-myomerger polypeptide) is found. In some embodiments, the concentration of at least one formulary ingredient is not that same as that found in one or more natural systems (e.g., any natural system found in nature) in which the nucleic acid molecule which encodes an inventive polypeptide (e.g., wt-myomerger polypeptide or extracellular wt-myomerger polypeptide) is found.

In certain embodiments, pharmaceutical compositions can be formulated to release the active ingredient (e.g., a myomerger polypeptide or an extracellular myomerger polypeptide) substantially immediately upon the administration or any substantially predetermined time or time after administration. Such formulations can include, for example, controlled release formulations such as various controlled release compositions and coatings.

Other formulations (e.g., formulations of a pharmaceutical composition) can, in certain embodiments, include those incorporating the drug (or control release formulation) into food, food stuffs, feed, or drink.

Methods

Some embodiments of the invention include methods of using a myomerger polypeptide or an extracellular myomerger polypeptide. In other embodiments, the method comprises contacting a myomerger polypeptide or an extracellular myomerger polypeptide with a cell or a liposome.

In certain embodiments, the method comprising contacting can be used to promote or increase fusion activity (e.g., by driving the transition of hemifusion intermediates to fusion completion) between two cells. For example, a myomerger polypeptide or an extracellular myomerger polypeptide can be contacted with one or two cells to promote or increase fusion activity of the one or two cells. If there are two cells, the two cells can be the same or different. The one or two cells be any of the cells disclosed herein including but not limited to an animal cell, a mammalian cell, a human cell, a rat cell a mouse cell, a muscle cell, a non-muscle cell, a myoblast, a fibroblast, a C2C12 cell, a 10T ½ fibroblast, an NIH/3T3 cell, a CHO cell, a mesenchymal stem cell (MSC), a hematopoietic stem cell, a blood cell, a red blood cell, a bone marrow cell, an adipose stem cell, or a combination thereof.

In some embodiments, a myomerger polypeptide or an extracellular myomerger polypeptide can be contacted with a cell or liposome to result in increased permeabilization of a cell membrane or a liposome membrane. In certain embodiments, permeabilization of a membrane (or related terms such permeabilizing or permeabilize) means the ability of a substance (e.g., phalloidin, ions, labeled molecules such as deuterated water, C13 labeled sucrose, etc.) to pass through a membrane. In other embodiments, permeabilization of a membrane can be measured using any suitable method including but not limited to a phalloidin assay, such as that described herein. In some embodiments, permeabilization results in cell lysis or liposome lysis, formation of one or more pores in the cell membrane or liposome membrane, or the stressing (e.g., via convex (positive) curvature of the membrane, for example, at a negatively curved rim of a hemifusion structure) of a membrane. In other embodiments, a myomerger polypeptide or an extracellular myomerger polypeptide can be contacted with a cell or liposome to result in cell lysis or liposome lysis. In certain embodiments, a myomerger polypeptide or an extracellular myomerger polypeptide can be contacted with a cell or liposome to form one or more pores in a membrane of the cell or in a membrane of the liposome. In other embodiments, the cell can be a bacterial cell (e.g., gram-positive bacterial cell or gram-negative bacterial cell), a fungal cell, an insect cell (e.g., Sf9), or an animal cell (e.g., a mammalian cell, a muscle cell, a myoblast, or a cancer cell).

In some embodiments, the cell can be an animal cell. In other embodiments, the cell can be a mammalian cell. In other embodiments, the cell can be a human cell, a rat cell, a mouse cell, a muscle cell, a non-muscle cell, a myoblast, a fibroblast, a C2C12 cell, a 10T ½ fibroblast, an NIH/3T3 cell, a CHO cell, a mesenchymal stem cell (MSC), a hematopoietic stem cell, a blood cell, a red blood cell, a bone marrow cell, or an adipose stem cell. In certain embodiments, the cell is not a fibroblast. In other embodiments, the cell can be a human cell, a rat cell, a mouse cell, a muscle cell, a non-muscle cell, a myoblast, a C2C12 cell, a CHO cell, a mesenchymal stem cell (MSC), a hematopoietic stem cell, a blood cell, a red blood cell, a bone marrow cell, or an adipose stem cell. In still other embodiments, the cell can be a muscle cell, a non-muscle cell, a myoblast, a C2C12 cell, a CHO cell, a mesenchymal stem cell (MSC), a hematopoietic stem cell, a blood cell, a red blood cell, a bone marrow cell, or an adipose stem cell.

In some embodiments, the cell can be a bacterial cell (e.g., a gram negative bacterial cell or a gram positive bacterial cell) such as but not limited to *Escherichia coli* (*E. coli*), *Salmonella, Shigella*, other Enterobacteriaceae, *Pseudomonas, Moraxella, Helicobacter, Stenotrophomonas*, Bdellovibrio, acetic acid bacteria, *Legionella, Neisseria gonorrhoeae, Neisseria meningitidis, Moraxella catarrhalis, Haemophilus influenzae, Klebsiella pneumoniae, Legionella pneumophila, Pseudomonas aeruginosa, Proteus mirabilis, Enterobacter cloacae, Serratia marcescens, Helicobacter pylori, Salmonella enteritidis, Salmonella typhi, Acinetobacter baumannii, Chlamydia trachomatis, Yersinia pestis, Listeria monocytogenes, Streptococcus, Staphylococcus*, cocci, bacilli, *Corynebacterium, Listeria, Bacillus, Clostridium, Rathybacter, Leifsonia*, and *Clavibacter*. In certain embodiments, the cell can be a fungal cell such as but not limited to aspergillosis, candidiasis, coccidioidomycosis, cryptococcosis, histoplasmosis, mycetomas, paracoccidioidomycosis, trichophyton, epidermophyton, micro sporum, dermatophytic fungi, or keratinophilic fungi. In other embodiments, the cell can be a cancer cell, such as but not limited to cells from glioblastoma multiforme, endometrial cancer, melanoma, prostate cancer, lung cancer, breast cancer, kidney cancer, bladder cancer, basal cell carcinoma, thyroid cancer, squamous cell carcinoma, neuroblastoma, ovarian cancer, renal cell carcinoma, hepatocellular carcinoma, colon cancer, pancreatic cancer, chronic lymphocytic leukemia (CLL), acute lymphoblastic leukemia, rhabdomyosarcoma, meningioma, gastric cancer, Glioma, oral cancer, nasopharyngeal carcinoma, rectal cancer, stomach cancer, uterine cancer, leukemias and tumors thereof. In other embodiments, the cancer cell is a tumor cancer cell.

In some embodiments, the cell is a bacterial cell (e.g., gram negative bacterial cell or gram positive bacterial cell) or a red blood cell. In other embodiments, the cell is an *E. coli* cell, a *Listeria monocytogenes* cell, or a red blood cell.

The contacting of the cell or liposome in the method can occur by any suitable manner such as but not limited to those disclosed herein. For example, the contacting can occur in vitro or the contacting can occur in vivo.

Animals include but are not limited to mammals, primates, monkeys (e.g., macaque, rhesus macaque, or pig tail macaque), humans, canine, feline, bovine, porcine, avian (e.g., chicken), mice, rabbits, and rats. As used herein, the term "subject" refers to both human and other animal subjects.

In certain embodiments, the method to contact a cell or liposome can be part of a treatment of a disease. In some embodiments, the disease can be any disease, such as but not limited to, a bacterial infection (e.g., infections with a gram positive bacteria, such as but not limited to those disclosed herein, or infections with a gram negative bacteria, such as but not limited to those disclosed herein), fungal infections (e.g., infections with fungi such as but not limited to those disclosed herein), or cancer (such as but not limited to glioblastoma multiforme, endometrial cancer, melanoma, prostate cancer, lung cancer, breast cancer, kidney cancer, bladder cancer, basal cell carcinoma, thyroid cancer, squamous cell carcinoma, neuroblastoma, ovarian cancer, renal cell carcinoma, hepatocellular carcinoma, colon cancer, pancreatic cancer, chronic lymphocytic leukemia (CLL), acute lymphoblastic leukemia, rhabdomyosarcoma, meningioma, gastric cancer, Glioma, oral cancer, nasopharyngeal carcinoma, rectal cancer, stomach cancer, uterine cancer, and leukemias and tumors thereof) or a combination thereof. As used herein, the term "treating" (and its variations, such as "treatment") is to be considered in its broadest context. In particular, the term "treating" does not necessarily imply that an animal is treated until total recovery. Accordingly, "treating" includes amelioration of the symptoms, relief from the symptoms or effects associated with a condition, decrease in severity of a condition, or preventing, preventively ameliorating symptoms, or otherwise reducing the risk of developing a particular condition. As used herein, reference to "treating" an animal includes but is not limited to prophylactic treatment and therapeutic treatment. In some embodiments, treating does not include prophylactic treatment. Any of the methods or compositions (e.g., pharmaceutical compositions) described herein can be used to treat an animal.

In yet other embodiments, the contacting can occur by any suitable administration route. Administration routes can be, but are not limited to the oral route, the parenteral route, the cutaneous route, the nasal route, the rectal route, the vaginal route, and the ocular route. In other embodiments, administration routes can be parenteral administration, a mucosal administration, intravenous administration, depot injection, subcutaneous administration, topical administration, intradermal administration, oral administration, sublingual administration, intranasal administration, or intramuscular administration (e.g., intramuscular injection). In certain embodiments, the contacting comprises an injection or an injection into a cancer tumor. In certain embodiments, the contacting comprises an injection comprising an extracellular myomerger polypeptide, a myomerger polypeptide, or both (e.g., in a composition or in a pharmaceutical composition).

In still other embodiments, the method can optional further comprise one or more of the contacting steps.

The presently disclosed subject matter is further illustrated by the following specific but non-limiting examples. The following examples may include compilations of data that are representative of data gathered at various times during the course of development and experimentation related to the present invention.

EXAMPLES

Example Set A

Some methods. figures, and discussion of the experiments in this Example Set can be found in LEIKINA et al. (2018) "Myomaker and Myomerger Work Independently to Control Distinct Steps of Membrane Remodeling during Myoblast Fusion" Developmental Cell, Vol. 46, No. 6, pp. 767-780, which is herein incorporated by reference in its entirety.

Materials and Methods

Cells

C2C12 cells and 10T½ fibroblasts were purchased from American Type Culture Collection. Both cell types were propagated in DMEM (Gibco) containing 10% heat-inactivated bovine growth serum (BGS) and supplemented with penicillin-streptomycin (1%) at 37° C. and 5% $CO_2$. Myomaker$^{-/-}$ and Myomerger$^{-/-}$ C2C12 cell lines were generated previously by using CRISPR/Cas9 mutageneisis (MILLAY et al. (2016) "Structure-function analysis of myomaker domains required for myoblast fusion" Proc Natl Acad Sci USA, Vol. 113, pp. 2116-2121, which is herein incorporated by reference in its entirety; QUINN et al. (2017) "Myomerger induces fusion of non-fusogenic cells and is required for skeletal muscle development" Nat Commun, Vol. 8, Article 15665, which is herein incorporated by reference in its entirety). Primary myoblasts were also generated previously (MILLAY et al. (2016) "Structure-function analysis of myomaker domains required for myoblast fusion" Proc Natl Acad Sci USA, Vol. 113, pp. 2116-2121, which is herein incorporated by reference in its entirety; QUINN et al. (2017) "Myomerger induces fusion of non-fusogenic cells and is required for skeletal muscle development" Nat Commun, Vol. 8, Article 15665, which is herein incorporated by reference in its entirety), and grown on collagen coated substrates but plated on fibronectin for differentiation. All myoblasts were differentiated by switching to DMEM containing 2% heat-inactivated horse serum (HS) and antibiotics. NIH 3T3 mouse fibroblasts of clone 15 cell line that stably express HA of Japan strain of influenza were a kind gift of Dr. Joshua Zimmerberg, NICHD, NIH (WILSON et al. (2015) "Hemagglutinin clusters in the plasma membrane are not enriched with cholesterol and sphingolipids" Biophys J, Vol. 108, pp. 1652-1659, which is herein incorporated by reference in its entirety). These HA-expressing cells were cultured in DMEM with 10% FBS, $10^4$ units/mL penicillin G, and 10 mg/mL streptomycin at 37° C. and 5% $CO_2$. Human red blood cells (RBCs) were isolated from the blood of healthy donors (who had consented to participate in the NIH IRB-approved Research Donor Program in Bethesda, MD; all samples were anonymized).

Lipid and Content Mixing Assays and Synchronized Fusion Assays

We uncoupled the myoblast fusion stage of myogenic differentiation from the stages that prepare the cells for fusion using a fusion-synchronization approach described previously (GAMAGE et al. (2017) "Insights into the localization and function of myomaker during myoblast fusion" J Biol Chem, Vol. 292, pp. 17272-17289, which is herein incorporated by reference in its entirety; LEIKINA et al. (2013) "Extracellular annexins and dynamin are important for sequential steps in myoblast fusion" J Cell Biol, Vol. 200, pp. 109-123, which is herein incorporated by reference in its entirety). In brief, fusion-committed myoblasts were placed into complete medium supplemented with 150 μM lauroyl LPC (#855475P, Avanti Polar Lipids). 16 h later we washed the cells three times with LPC-free complete medium. C2C12 cells and primary myoblasts grown to 75% confluence in a 100 mm dish were labeled with either fluorescent lipid the Vybrant DiI or membrane-permeant Green CMFDA cell tracker or orange CMRA Cell Tracker (#V22885; #C7025 and #C34551, respectively, ThermoFisher Scientific), as recommended by the manufacturer and described previously (LEIKINA et al. (2013) "Extracellular annexins and dynamin are important for sequential steps in myoblast fusion" J Cell Biol, Vol. 200, pp. 109-123, which is herein incorporated by reference in its entirety). These probes were also used to distinguish hemifusion and pore formation (described below) even when LPC was not used to synchronize cells.

We labeled C2C12 cells 48 hours after placement in the differentiation medium, and co-plated differently labeled cells in a 1-to-1 ratio. For synchronized fusion, LPC was applied 2-3 hours after co-plating cells. The cells were incubated in the LPC-containing complete medium for 16 hours. Fusion was scored 30 min after LPC removal and thus ~68 hours after placing the cells into differentiation medium. In the experiments on murine primary myoblasts, we labeled proliferating cells in the growth medium. We co-plated differently labeled cells at 1-to-1 ratio and grew the cells in the growth medium for 16 more hours. Then we placed the cells into differentiation medium and 7 hours later applied LPC. We kept the cells in LPC-supplemented differentiation medium for 16 hours, washed out LPC with LPC-free medium and 30 minutes later (~24 hours after placing the cells into differentiation medium) scored fusion. Antibodies to Myomerger (sheep ESGP Ab #PAS-47639, ThermoFisher Sci.) or, in control experiments, sheep IgG-isotope control (#Ab37385, Abcam) were added to the LPC-free medium in which the cells were kept after LPC withdrawal.

Myoblast Fusion Assays and Quantification

To specifically characterize different steps in fusion, we used 3 distinct assays: (i) hemifusion between cells labeled with membrane probe and content probe with unlabeled cells where hemifusion was detected as the appearance of lipid-labeled mononucleated cells without the content probe (FIG. 1A, FIG. 2A, FIG. 1E)); (ii) opening of a fusion pore in fusion between cells labeled with green cell tracker and cells labeled with orange cell tracker was detected as appearance of double-labeled cells (FIG. 1F); and (iii) fusion completion was detected as formation of multinucleated cells. As a control, we found no mononucleated cells labeled with only membrane probe when cells labeled with both lipid and content probe as in (i) were incubated in the absence of unlabeled cells, showing that labeled cells do not lose their content probe (data not shown). This indicates that when double labelled cells are mixed with unlabeled cells, the mononucleated cells labeled only with the lipid probe are indeed formed by hemifusion. Formation of multinucleated myotubes was quantified as the percentage of cell nuclei present in myotubes normalized to the total number of cell nuclei. Hemifusion and fusion pore opening were quantified as a number of double-labeled mononucleated cells normalized to the total number of cell nuclei in the field. For each condition, ≥8 randomly chosen fields of view were imaged. We also analyzed fusion by assessing the number of nuclei in myosin$^+$ cells. Here, cells were fixed with 4% paraformaldehyde (PFA)/PBS, permeabilized with 0.02% Triton X-100/PBS, and blocked with 3% BSA/PBS followed by immunostaining with myosin antibodies (MF 20, Developmental Studies Hybridoma Bank, 1:40) for one hour at room temperature. Alexa-Fluor secondary antibody (Invitrogen, 1:250) was incubated for 30 minutes at room temperature. Nuclei were stained with Hoechst (Invitrogen). Samples were imaged with a Nikon Eclipse inverted microscope with AIR confocal running NIS Elements and images were analyzed with Fiji (SCHINDELIN et al. (2012) "Fiji: an open-source platform for biological-image analysis" Nat Methods, Vol. 9, pp. 676-682, which is herein incorporated by reference in its entirety)

Generation of Recombinant Myomerger Proteins

We generated recombinant proteins using either pMALX (MOON et al. (2010) "A synergistic approach to protein crystallization: combination of a fixed-arm carrier with surface entropy reduction" Protein Sci, Vol. 19, pp. 901-913, which is herein incorporated by reference in its entirety) or a modified pET28a backbone (generous gifts from Dr. Thomas Thompson, University of Cincinnati and Dr. Lars Pedersen, NIEHS, NIH). Each of these plasmids contains maltose binding protein (MBP) as an N-terminal fusion protein, however the modified pET28a contains an N-terminal 6× histidine tag, thrombin cleavage site, and a PreScission Protease (PP) cleavage site after MBP. We cloned full-length Myomerger into pET28a-His-thrombin-MBP-PP and the ectodomain of Myomerger (amino acids 26-84) into both plasmids. The cDNA encoding full-length Myomerger or its ectodomain was obtained by amplifying the region from full-length Myomerger as a template. The above plasmids were transformed into *E. coli* BL21 (DE3) (KATTAMURI et al. (2012) "Members of the DAN family are BMP antagonists that form highly stable noncovalent dimers" J Mol Biol, Vol. 424, pp. 313-327, which is herein incorporated by reference in its entirety) and grown in LB medium at 30° C. supplemented with 50 μg $ml^{-1}$ ampicillin for pMALX or 50 μg $ml^{-1}$ kanamycin for pET28a-Histhrombin-MBP-PP, and once $OD_{600}$ reached 0.6, protein expression was induced for 4 hours with 0.25 mM IPTG. Cells were lysed in protein purification buffer (20 mM Tris-HCl (pH 7.5), 300 mM NaCl, 1 mM EDTA) with sonication. The proteins were affinity purified with amylose resin (BioRad) and eluted with 20 mM maltose (Sigma-Aldrich) in protein purification buffer. The proteins without the PP site (in pMALX: MBP & MBPMyomerger$^{26-84}$) were further purified using a Superdex G200 Gel-Filtration column (GE Healthcare Life Sciences) in liposomal buffer (20 mM HEPES, pH 7.4 and 90 mM NaCl). Purity of the proteins was analyzed through SDS-PAGE followed by Coomassie Brilliant Blue G-250 staining (BioRad). Protein fractions containing proteins of interest were combined and concentrated with a 10K Molecular Weight Cutoff (MWCO) membrane (Pall Corporation). After eluting from the amylose resin, the proteins with the PP site (in pET28a-His-thrombin-MBP-PP: His-MBP-Myomerger$^{26-84}$) were incubated with PreScission protease (Sigma-Aldrich) overnight at 4° C. The cleaved protein was then dialyzed at 4° C. overnight against cation exchange buffer (50 mM Sodium acetate pH 6.2) and was loaded onto a Mono S 5/5 cation exchange column (GE Healthcare Life Sciences). The protein was eluted with a linear NaCl gradient up to 1M to remove MBP and PP. Purity of the protein was analyzed through SDS-PAGE and the fractions containing Myomerger$^{26-84}$ were dialyzed with liposomal buffer and concentrated with a 3K Molecular Weight Cutoff (MWCO) membrane (Pall Corporation). Protein concentrations were measured using the Bradford method (BioRad) with BSA as a standard and aliquots were frozen in liquid nitrogen until further use.

Application of Hypotonic Osmotic Shock, Chlorpromazine, Detergents, and Recombinant Protein To assess an ability for osmotic stress to improve fusion, we treated the cells with PBS diluted by $H_2O$ (1:3) as described (CHERNOMORDIK et al. (1998) "The pathway of membrane fusion catalyzed by influenza hemagglutinin: restriction of lipids, hemifusion, and lipidic fusion pore formation" J Cell Biol, Vol. 140, pp. 1369-1382, which is herein incorporated by reference in its entirety). To explore permeabilization of the plasma membrane of myoblasts we applied a strong hypotonic osmotic shock. We washed the cells with PBS and placed them in distilled water for 30 seconds at room temperature in the presence of Alexa Fluoro 488 phalloidin (#A12379, Invitrogen, final concentration of ~20 nM). Then we washed the cells in PBS and placed them into the complete medium for 10 minutes at 37° C. in the presence of Hoechst 33342 (#H3570, ThermoFisher Sci., dilution 1:1000). After washing with PBS, we scored the percentage of permeabilized (phalloidin-labeled) cells using fluorescence microscopy.

Chlorpromazine CPZ (Sigma) was prepared as a 0.5 mM solution in PBS. At the time of LPC removal, synchronized WT, Myomaker$^{-/-}$ or Myomerger$^{-/-}$ C2C12 cells were placed into PBS supplemented with 50 μM CPZ for 60 seconds. Then the medium was replaced with differentiation medium for 30 minutes at 37° C. Fusion (syncytium formation) extents were compared with those in the control experiments, where the cells were treated with neither LPC nor CPZ.

For detergent and recombinant protein application, 2.5×$10^4$ myoblasts per well of an 8-well μ-slide (Ibidi) were differentiated for 72 hours. 0.06% Octyl-β-Glucoside (OG) (Anatrace) in differentiation media was incubated for 30 minutes at 37° C. Cells were washed with PBS and switched back to normal differentiation media for 5 hours. For primary myoblasts, 3×$10^4$ cells were plated per well of an 8-well μ-slide (Ibidi) coated with fibronectin (Sigma-Aldrich, 5 μg/$cm^2$) and differentiated for 36 hours. Cells were treated with 0.06% OG in PBS for 30 minutes at 37° C., washed with PBS and switched back to normal differentiation media for 2 hours. For recombinant proteins, cells were treated with various concentrations of rMBP or rMBP-Myomerger$^{26-84}$ (0.5 μM, 1.25 μM, 3 μM, 6.25 μM and 12.5 μM), or 6.25 μM of Magainin 2 (AnaSpec), in differentiation media for 20 hours at 37° C.

Membrane Extraction

C2C12 cells were harvested on day 2 of differentiation in ice cold hypotonic buffer (TE buffer: 10 mM Tris-HCl pH 8, 2 mM EDTA) supplemented with complete protease inhibitor (Roche) and lysed using a dounce homogenizer. Lysates were then centrifuged at 800×g for 5 minutes at 4° C. to separate nuclei and cell debris. The supernatant was then centrifuged at 100,000×g for one hour to isolate total membranes. The membrane pellets were resuspended in TE buffer, 1 M NaCl, 1% SDS/TE, or in 0.1 M sodium carbonate (pH 11.5), and incubated on ice for 30 minutes with occasional vortexing. The membrane fractions were isolated at 100,000×g for 1 hour and resuspended with RIPA buffer (50 mM Tris-HCl pH 7.4, 1% Triton X-100, 1% sodium deoxycholate, 1 mM EDTA, 0.1% SDS) at volumes equal to the supernatant. 10 μl of each fraction was separated by SDS-PAGE and analyzed for presence of Myomerger, Caveolin-3 (integral membrane protein), and Golgin 97 (peripheral membrane protein). The gel was transferred to a pre-equilibrated PVDF membrane (BioRad). The membrane was blocked with 5% milk in TBS-T (10 mM Tris-HCl pH 8.0, 150 mM NaCl)/0.05% Tween-20) for one hour at room temperature. After three washes with TBS-T, the membrane was incubated with primary antibodies/1% BSA overnight at 4° C. Myomerger antibody (R&D Systems #AF4580) was used at 1:200, Caveolin-3 antibody (BD Transduction Laboratories #610421) at 1:6700 and Golgin 97 (Cell Signaling Technologies #13192) at 1:1000. Membrane was then washed with TBS-T and incubated with Alexa Fluor 680 donkey anti-sheep secondary antibody (Invitrogen), Alexa Fluor 680 goat anti-mouse secondary antibody (Invitrogen) and IRDye 800CW goat anti-rabbit (LI-COR), respectively at 1:5000. Bands were visualized using the Odyssey® infrared detection system (LI-COR Biosciences).

Surface Biotinylation

C2C12 cells (2×100 mm plates) were differentiated for two days and washed three times with cold PBS (137 mM NaCl, 2.7 mM KCl, 10 mM $Na_2HPO_4$, $KH_2PO_4$ pH 8.0). Cells were treated with 0.5 mg/mL EZ-link Sulfo-NHS—SS-Biotin (Pierce) at room temperature for 30 minutes. A control plate not exposed to EZ-link Sulfo-NHS—SS-Biotin was also processed. The cells were washed with PBS and non-reacted biotin was blocked with 50 mM Tris-HCl, pH 7.5. The cells were harvested with 1 mL of lysis buffer (10 mM Tris-HCl pH 7.5, 150 mM NaCl, 0.1% Triton X-100, 100 μM oxidized glutathione (Sigma-Aldrich), Protease Cocktail (Roche)) and were lysed with sonication five times on ice. Samples were centrifuged at a speed of 15,000 rpm for 20 minutes and supernatants were incubated with magnetic streptavidin beads (Pierce) at room temperature for one hour to isolate biotinylated proteins. Beads were washed at least six times with the lysis buffer. For immunoblot analysis, 20 μL of RIPA buffer (50 mM Tris-HCl pH 7.4, 1% Triton X-100, 1% sodium deoxycholate, 1 mM EDTA, 0.1% SDS) was added along with 5 μL of 5× Laemmli loading buffer (300 mM Tris-HCl pH 6.8, 10% SDS, 50% glycerol, 0.25% bromophenol blue) to the beads and heated at 95° C.

for 5 minutes. Western blotting was performed as described above for Myomerger and Tubulin. Tubulin (Santa Cruz #sc-8035) was used at 1:50.

Liposome Preparation and Assays

The Lipids Used in this Study were Dioleoylphosphatidylcholine (DOPC) and dioleoylphosphatidylserine (DOPS), 1,2-distearoly-sn-glycero-3-phosphoethanolamine-N-[amino(polyethylene glycol)-2000] (ammonium salt) (DSPE-PEG (2000)) from Avanti Polar Lipids. DiI and DiD (Invitrogen) were used as lipid dyes for lipid mixing experiments. For leakage experiments in FIGS. 5B, 5C, the liposomes were processed as previously described (KYOUNG et al. (2013) "Studying calcium-triggered vesicle fusion in a single vesicle-vesicle content and lipid-mixing system" Nat Protoc, Vol. 8, pp. 1-16, which is herein incorporated by reference in its entirety). Briefly, the lipids were mixed to a final concentration of 10 mM with a molar ratio of 70:30 (DOPC:DOPS) and were dried under vacuum to form a lipid film on the wall of a glass tube. The dried lipid film was resuspended in liposomal buffer (20 mM HEPES, 90 mM NaCl, pH 7.4) with 50 mM sulforhodamine B (Sigma-Aldrich). After three freeze-thaw cycles, the labeled liposomes were isolated using a NAP-25 column (GE healthcare) which also removed free sulforhodamine B. For leakage experiments described in FIGS. 5E, 5G the liposomes were prepared through freeze-thaw followed by extrusion. In brief, the mixtures DOPC:DOPS (molar ratio 70:30) or DOPC:DOPS:PEG-PE (molar ratio 68:30:2) were dried under vacuum in a glass tube and the dried lipid film was hydrated in liposomal buffer with 50 mM sulforhodamine B. For the lipid mixing experiments described in FIG. 5G, lipids were mixed to obtain DOPC:DOPS ((unlabeled) molar ratio 70:30), DOPC:DOPS:DiI:DiD ((labeled) molar ratio 66:30:2:2), DOPC:DOPS:PEG-PE ((unlabeled) molar ratio 68:30:2) DOPC:DOPS:PEG-PE:DiI:DiD ((labeled) molar ratio 64:30:2:2:2) and the dried lipid film was suspended in liposomal buffer. The resulting lipid suspensions were submitted to five freeze-thaw cycles followed by 25 extrusions through polycarbonate filters (100 nm pore size, Avanti Polar Lipids) using a mini-extruder (Avanti Polar Lipids) to produce large unilamellar vesicles (LUVs). Details of the leakage assay have previously been described (CROWE et al. (2017) "A Proteoliposome Method for Assessing Nanotoxicity on Synaptic Fusion and Membrane Integrity" Small Methods, Article 1, which is herein incorporated by reference in its entirety). Experiments were performed using a Gemini XPS plane reader (Molecular Devices) with a 96-well microplate (Corning Inc). Fluorescence from the sulforhodamine B labeled liposomes was measured every 7 seconds for 15 minutes after the addition of proteins. All measurements were performed at room temperature. The excitation and emission wavelengths were 544 and 590 nm, respectively. The emission fluorescence for each time point was measured as $F_n$ The emission fluorescence of the untreated liposomes was measured as $F_0$, and that of the liposomes solubilized with 0.1% SDS was defined as $F_{100}$. The percentage of liposome leakage at each time point is defined as: liposome leakage (% of SDS)=$(F_n-F_0)\times 100/(F_{100}-F_0)$. For lipid mixing experiments, labeled and unlabeled liposomes were mixed at a ratio of 1:9 to obtain a final lipid concentration of 100 μM (outer leaflet concentration was 50 μM). Fluorescence intensities were monitored every 20 seconds for 15 minutes after adding the protein in two channels with the excitation wavelength of 530 nm and emission wavelengths of 570 and 670 nm for donor DiI and acceptor DiD respectively. Fluorescence changes for donor (DiI) emission were plotted as a percentage of SDS quenching. All measurements were performed at room temperature.

Dox-Inducible Cell Fusion Reconstitution

Viruses were generated using a procedure adapted from the Broad Institute protocol; briefly, 293T cells (passages ≤15) were seeded in culture medium (DMEM, 10% FCS, 1% Pen-Strep) at $3.8\times10^6$ cells/100 mm plates. After 18 hours, culture medium was replaced with 9.5 mL of antibiotic-free medium (DMEM, 10% FCS, without Pen-Strep). The transfection reaction mixture was prepared by mixing and incubating plasmid DNA (7.5 vg transfer, 4.8 vg packaging, 2.7 vg envelope) with Fugene6 (Promega: 3 μL:1 μg DNA) in 500 μL of serum-free antibiotic-free DMEM for 20 minutes at room temperature. This reaction mixture was then dispersed over the 293T cells 24 hours after seeding and transfection carried out for 16-18 hours at 37° C. The transfection medium was replaced with virus-harvesting medium (DMEM, 20% FCS, 1% Pen-Strep) and virus generation allowed to proceed for 48 hours. Supernatants were harvested, filtered through 0.45 μm syringe filters, and overlaid on cells for transduction. Identical protocols were followed for generation of both Myomaker-encoding retroviruses (using pBX-myomaker transfer vector (MILLAY et al. (2013) "Myomaker is a membrane activator of myoblast fusion and muscle formation" Nature, Vol. 499, pp. 301-305, which is herein incorporated by reference in its entirety) and Gag/Pol packaging constructs (Addgene)) and Myomerger-encoding lentiviruses (using the psPAX2 packaging construct (Addgene)). For both we also included the envelope plasmid, pCMV-VSV-G (Addgene). cDNA for Myomerger (QUINN et al. (2017) "Myomerger induces fusion of non-fusogenic cells and is required for skeletal muscle development" Nat Commun, Vol. 8, Article 15665, which is herein incorporated by reference in its entirety) and Myomerger-FLAG was cloned into the pLVX-TetONE-Puro transfer vector (Clonetech) to achieve Doxycycline (dox)-inducible expression of Myomerger in transduced cells that would also be constitutively puromycin-resistant. To generate Myomerger$^{\Delta1\text{-}25}$, amino acids 1-25 were replaced with a synthetic cleavable signal sequence from influenza virus hemagglutinin using standard PCR-based mutagenesis and this construct was cloned into the pBabe-X plasmid. All recombinant plasmids were confirmed by sequencing prior to use and primers can be found on the Key Resources page of LEIKINA et al. (2018) "Myomaker and Myomerger Work Independently to Control Distinct Steps of Membrane Remodeling during Myoblast Fusion" Developmental Cell, Vol. 46, No. 6, pp. 767-780, which is herein incorporated by reference in its entirety.

Transduction of 10T½ fibroblasts was achieved by seeding at $10^5$ cells/well in a 6-well format in 2 mL of complete medium (DMEM, 10% BGS, 1% Pen-Strep) and incubated overnight at 37° C. On the next day, cells were serially transduced with retro-Myomaker and lenti-Myomerger viruses using a spinfection protocol; briefly, cells were initially overlaid with 2.5 mL of undiluted retrovirus-containing medium supplemented with 6 μg/mL polybrene and subjected to centrifugation (652×g in a swinging bucket rotor) at 23° C. for 60 minutes. Infection was continued at 37° C. for an additional 12 hours, after which the spinfection protocol was repeated with the inducible Myomerger-encoding lentivirus. After a cumulative ~24-hour transduction period, cells were returned to complete medium. Exposure to selection medium (complete medium, 4 μg/mL puromycin) was started 48 hours after lentiviral transduction was initiated and proceeded for 2 days. Surviving cells were trypsinized (0.05% trypsin), propagated in complete medium on a 3-day/passage cycle, and subjected to the 2 day puromycin-selection protocol every 2-3 passages. Fusogenic capability, protein expression, and co-immunoprecipitations were assessed in passages 3-5 or later. Assessment of protein expression was achieved by seeding cells in a 12-well format ($5\times10^4$ cells/well) in complete medium on day 0, and treated with ±dox containing medium beginning on day 1 for 48 hours. Cells were then rapidly washed twice in ice-cold 1×PBS, directly lysed in 50 μL of 1× Laemmli buffer containing 100 mM DTT; lysates were heated at 95° C. for 10 minutes before being subjected to immunoblot analyses as described above. To assess fusion reconstitution, transduced 10T½ fibroblasts were seeded in 8-chamber Ibidi slides at $5\times10^3$ cells/chamber (300 μL complete medium) on day 0 and incubated overnight. On day 1 (~16-18 hours post-seeding), Myomerger expression was induced by treating cells in experimental chambers with dox containing complete medium (1 μg/mL), while control chambers received normal (-dox) medium. Media (±dox) was replaced once at 36-hour time point and assay allowed to proceed for a total of 72 hours of dox treatment at which time fusion was evaluated.

Co-Immunoprecipitations and Super-Resolution Microscopy

Retrovirus used for acute infection (FIG. 6A) was generated from Platinum E cells (Cell Biolabs), which were transfected with combinations of pBX-Empty, pBX-Myomerger (QUINN et al. (2017) "Myomerger induces fusion of non-fusogenic cells and is required for skeletal muscle development" Nat Commun, Vol. 8, Article 15665, which is herein incorporated by reference in its entirety), or pBX-FLAG-Myomaker (MILLAY et al. (2016) "Structure-function analysis of myomaker domains required for myoblast fusion" Proc Natl Acad Sci USA, Vol. 113, pp. 2116-2121, which is herein incorporated by reference in its entirety) (10 μg total DNA), and virus was collected 48 hours after transfection. Viral supernatants were filtered through a 0.45 μm syringe filter and incubated with fibroblasts or myoblasts (C2C12) for 18 hours. Viral media was replaced with normal growth media and cells were harvested 72 hours after infection. FLAG-Myomaker contains a cleavable, synthetic signal sequence followed by the FLAG epitope then full-length Myomaker (MILLAY et al. (2016) "Structure-function analysis of myomaker domains required for myoblast fusion" Proc Natl Acad Sci USA, Vol. 113, pp. 2116-2121, which is herein incorporated by reference in its entirety). For all immunoprecipitations, cells were washed with ice cold PBS, scraped into a conical tube, pelleted and resuspended in 1 ml of Buffer 1 (50 mM Tris-HCl pH 7.4, 150 mM NaCl, 1 mM EDTA, 0.1% Triton X-100) supplemented with complete protease inhibitor (Roche). Cells were incubated for 15 minutes, passed through a 27G ½ needle 10 times, and mixed for 1 hour at 4° C. To immunoprecipitate FLAG tagged proteins, the supernatants were collected by centrifugation at 21,000×g for 15 minutes and incubated with 50 μL of pre-washed Anti-FLAG M2 affinity resin (Sigma) for ~16 hours at 4° C. To immunoprecipitate untagged Myomerger, the supernatants were collected by centrifugation at 1000×g for 15 min and pre-cleared by incubation with Protein A Dynabeads (Life Technologies) for 2 hours at 4° C. To generate the antibody-bead mix, 6 μg of Myomerger antibodies were incubated with 50 μL of pre-washed Protein A Dynabeads for 2 hours at 4° C. The antibody-beads were washed thrice in Buffer 1 and incubated with the pre-cleared supernatant for ~16 hours at 4° C. The beads were then washed with high salt (50 mM Tris, 700 mM NaCl, 1 mM EDTA) buffer, followed by three washes with Buffer 1. Immunoprecipitated proteins were eluted using 30 μL of RIPA buffer (50 mM Tris-HCl pH 7.4, 1% Triton X-100, 1% sodium deoxycholate, 1 mM EDTA, 0.1% SDS) along with 6 μL of 5× Laemmli loading buffer. The beads were heated at 95° C. for 5 minutes and separated by SDS-PAGE and analyzed for presence of Myomaker, Myomerger, and GAPDH (as a loading control (Milipore; 1:10,000)). 10% of the total cells were lysed in SDS buffer (50 mM Tris-HCl pH 6.8, 1 mM EDTA, 2% SDS) and used as inputs.

Super-resolution microscopy was performed with a Nikon A1 LUN-A inverted confocal microscopy. C2C12 myoblasts were differentiated for two days and immunostained with custom Myomaker antibodies ((GAMAGE et al. (2017) "Insights into the localization and function of myomaker during myoblast fusion" J Biol Chem, Vol. 292, pp. 17272-17289, which is herein incorporated by reference in its entirety) and Myomerger antibodies described above. Images were acquired with a 100× objective NA1.45 at 4 times the Nyquist limit (0.03 μm pixel size). Z-stacks were acquired using a 0.4 AU pinhole yielding a 0.35 μm optical section at 0.1 μm intervals and 2× integration to avoid pixel saturation. Images were deconvolved with NIS elements using 15 iterations of the Landweber method. Images shown are a single focal plane.

HA-Mediated Cell Fusion Experiments

To examine effects of Myomaker and Myomerger expression on fusion mediated by influenza hemagglutinin (HA) we used NIH 3T3 mouse fibroblasts of clone 15 cell line that stably express HA of Japan strain of influenza (WILSON et al. (2015) "Hemagglutinin clusters in the plasma membrane are not enriched with cholesterol and sphingolipids" Biophys J, Vol. 108, pp. 1652-1659, which is herein incorporated by reference in its entirety). $HA^+$ cells were cultured in DMEM supplemented with 10% heat-inactivated FBS and antibiotics at 37° C. and 5% $CO_2$. The cells ($HA^+$ cells) express an uncleaved precursor form of HA, HA0, which is fusion-incompetent but mediates binding of $HA^+$ cells to red blood cells (RBCs) via HA0 interactions with sialic acid receptors at the surface of RBCs. We labeled RBCs with the fluorescent lipid PKH26 (Sigma) and loaded with carboxyfluorescein, CF (5-(and-6)-Carboxyfluorescein, mixed isomers, #C368, Invitrogen), as described in (CHERNOMORDIK et al. (1998) "The pathway of membrane fusion catalyzed by influenza hemagglutinin: restriction of lipids, hemifusion, and lipidic fusion pore formation" J Cell Biol, Vol. 140, pp. 1369-1382, which is herein incorporated by reference in its entirety) and prepared $HA^+$ for the experiments by treating them with trypsin to cleave HA0 into the fusion-competent HA1-S-S-HA2 form. In contrast to the optimized trypsin pre-treatment (5 μg/ml, 10 minutes, room temperature) that cleaves most of the cell-surface HAs (CHERNOMORDIK et al. (1998) "The pathway of membrane fusion catalyzed by influenza hemagglutinin: restriction of lipids, hemifusion, and lipidic fusion pore formation" J Cell Biol, Vol. 140, pp. 1369-1382, which is herein incorporated by reference in its entirety), we applied a lower concentration of trypsin for a shorter time (1 μg/ml trypsin, 2 minutes, room temperature) to cleave only a fraction of all HA0 molecules at the surface of HA-cells. After two washings with PBS, cells were incubated for 10 min with a 1 ml suspension of RBCs (0.05% hematocrit). HA-expressing cells with zero to two bound RBC per cell were washed three times with PBS to remove unbound RBC and then used. HA-cells with 0-2 bound RBCs per cell were treated with the low pH medium (PBS titrated with citrate to the pH 5.15 for 5 min at 37° C.). Low pH application was ended by replacement of the acidic solution with PBS. We assayed complete fusion and hemifusion in $HA^+$ fibroblast/RBC fusion by fluorescence microscopy as (i) the ratio of content probe-redistributed bound RBCs to the total number of bound RBCs and (ii) the ratio of lipid-redistributed but not content-mixing bound RBCs to the total number of bound RBCs, respectively. For each condition, we imaged and analyzed ≥30 randomly chosen fields of view (15-30 RBC-fibroblast pairs per field).

24 hours before fusion experiments, HA-cells at ~50% confluency were transfected with 2 µg/ml of pcDNA3-Myomaker, pcDNA3-Myomerger, or pcDNA3-empty per 35×10 $mm^2$ plate using Lipofectamine 3000. In parallel experiments, we transfected the cells with GFP vector and, based on GFP expression, estimated the transfection efficiency to be >60%. Using immunofluorescence microscopy, we verified expression of Myomaker or Myomerger in $HA^+$ cells by fixing the cells with 4% formaldehyde (10 minutes, room temperature). The cells were then washed with PBS and then treated with 0.1% Triton X-100 in PBS for 3 minutes at room temperature. After 3 washes with PBS, we blocked non-specific binding by treating the cells with 10% FBS in PBS for 10 minutes and then applied primary antibodies to either Myomaker (Abcam, Anti-TMEM8C antibody (#ab188300) at 1:50 dilution) or Myomerger antibodies (sheep Anti-ESGP antibody, ESGP Ab #PAS-47639, ThermoFisher Sci. at 1:100 dilution). The cells were incubated with primary antibodies for 1 hour at room temperature, washed 4 times, blocked with 10% FBS in PBS for 10 minutes and then incubated with secondary Alexa 647 goat anti-rabbit or donkey anti-sheep for Myomaker and Myomerger antibodies, respectively. In control experiments, neither lipid- nor content mixing was observed for either $HA^+$ $Myomerger^+$ fibroblasts or $HA^+$ $Myomaker^+$ fibroblasts that were not treated with trypsin or not treated with low pH (data not shown). Thus, on their own, neither Myomerger nor Myomaker initiates fusion of pre-docked membranes.

Quantification and Statistical Analysis

To quantify each experiment, at least 3 independent experiments were performed in duplicate and ≥5 randomly chosen fields of view were imaged (unless stated otherwise in the figure legend). At least 150 cells were counted manually for each image. We initially assessed the distribution of the data with a Shapiro-Wilk normality test. If the data were normally distributed, we used a parametric two-tailed t-test to determine significance. Data that were non-normally distributed were analyzed with a non-parametric Mann-Whitney test to determine significance. Data are presented in box-and-whisker plots where the center lines show the median, box the $25^{th}$-$75^{th}$ percentiles, and whiskers the maximum and minimum values, or in dot plots with mean and standard deviation. These statistical analyses were performed using the GraphPad Prism 6 software. The criterion for statistical significance was $P<0.05$ (*$P<0.05$, $P<0.01$, *$P<0.001$, ****$P<0.0001$).

Results

Myomaker and Myomerger Appear to Govern Distinct Aspects of the Fusion Pathway

To decipher mechanisms of myoblast fusion, we probed the precise stage of fusion that is arrested in myoblasts lacking either Myomaker or Myomerger. We utilized an assay that distinguishes hemifusion, detected as lipid mixing in the absence of content mixing, from fusion pore formation and expansion at the later stages of fusion, detected as content mixing and syncytium formation, respectively. We differentiated C2C12 myoblasts and labelled one population with both a lipid probe (DiI) and a content probe (green cell tracker), then this population was mixed with unlabeled cells and incubated for 24 hours (FIG. 1A). Due to continuous membrane trafficking in living cells, by the time fusion is evaluated many hours after cell labeling, fluorescent lipids are already distributed between the plasma membrane and intracellular membrane compartments. Multinucleated cells with both lipid and content probes indicate complete fusion. The cells that formed hemifusion connections but did not advance to complete fusion were identified as mononucleated cells containing the lipid probe but not the content probe. Note that lipid probe redistribution between the cells in the absence of content mixing is strong evidence for hemifusion, since fusion pores that would allow cell-to-cell passage of labeled intracellular vesicles would even more so allow passage of much smaller content probes. In WT cultures we observed mainly multinucleated cells (complete fusion) and a small number of hemifusion events (FIG. 1B), which was expected because WT cells are primed to drive early fusion intermediates to full fusion (LEIKINA et al. (2013) "Extracellular annexins and dynamin are important for sequential steps in myoblast fusion" J Cell Biol, Vol. 200, pp. 109-123, which is herein incorporated by reference in its entirety). While we observed minimal hemifusion events in $Myomaker^{-/-}$ C2C12 cultures, hemifusion was readily detected in $Myomerger^{-/-}$ C2C12 cells (FIG. 1B). Quantification of hemifusion and complete fusion revealed a reduction of hemifusion in $Myomaker^{-/-}$ myoblasts, but an accumulation of hemifused $Myomerger^{-/-}$ cells (FIG. 1C). Complete fusion was reduced in both cell types (FIG. 1C). Thus, Myomerger-deficient C2C12 myoblasts stall at an early intermediate stage as the fusion reaction cannot progress beyond the hemifusion step. The conclusion that fusion between $Myomerger^{-/-}$ cells is blocked downstream of hemifusion was confirmed with a different cell labeling strategy. Incubation of $Myomerger^{-/-}$ differentiated C2C12 myoblasts labeled with either membrane probe DiI or membrane probe DiO yielded mononucleated cells labeled with both probes for $Myomerger^{-/-}$ myoblasts but almost no such cells for WT and $Myomaker^{-/-}$ myoblasts (FIG. 1D). Similar experiments on primary myoblasts from $Myomaker^{-/-}$ and $Myomerger^{-/-}$ mice confirmed that Myomaker deficiency blocks lipid mixing and Myomerger deficiency arrests fusion downstream of lipid mixing (FIG. 1E).

The cell labeling strategies above do not detect fusion pores that do not expand to allow syncytial formation. To test if $Myomerger^{-/-}$ myoblasts can form small pores, we co-plated differentiated $Myomerger^{-/-}$ C2C12 myoblasts labeled with either green cell tracker or orange cell tracker (FIG. 1F). We observed double-labeled cells in WT, but not in $Myomerger^{-/-}$ cultures, indicating that Myomerger-deficient cells do not form fusion pores large enough to allow redistribution of the cell trackers (FIG. 1G and FIG. 1H). Taken together, these data indicate that Myomaker and Myomerger govern distinct steps of the membrane fusion reaction in myoblasts, where Myomaker functions at or upstream of hemifusion and Myomerger drives pore formation.

Myomaker Activity does not Appear to Involve Myomerger

Figure 2:
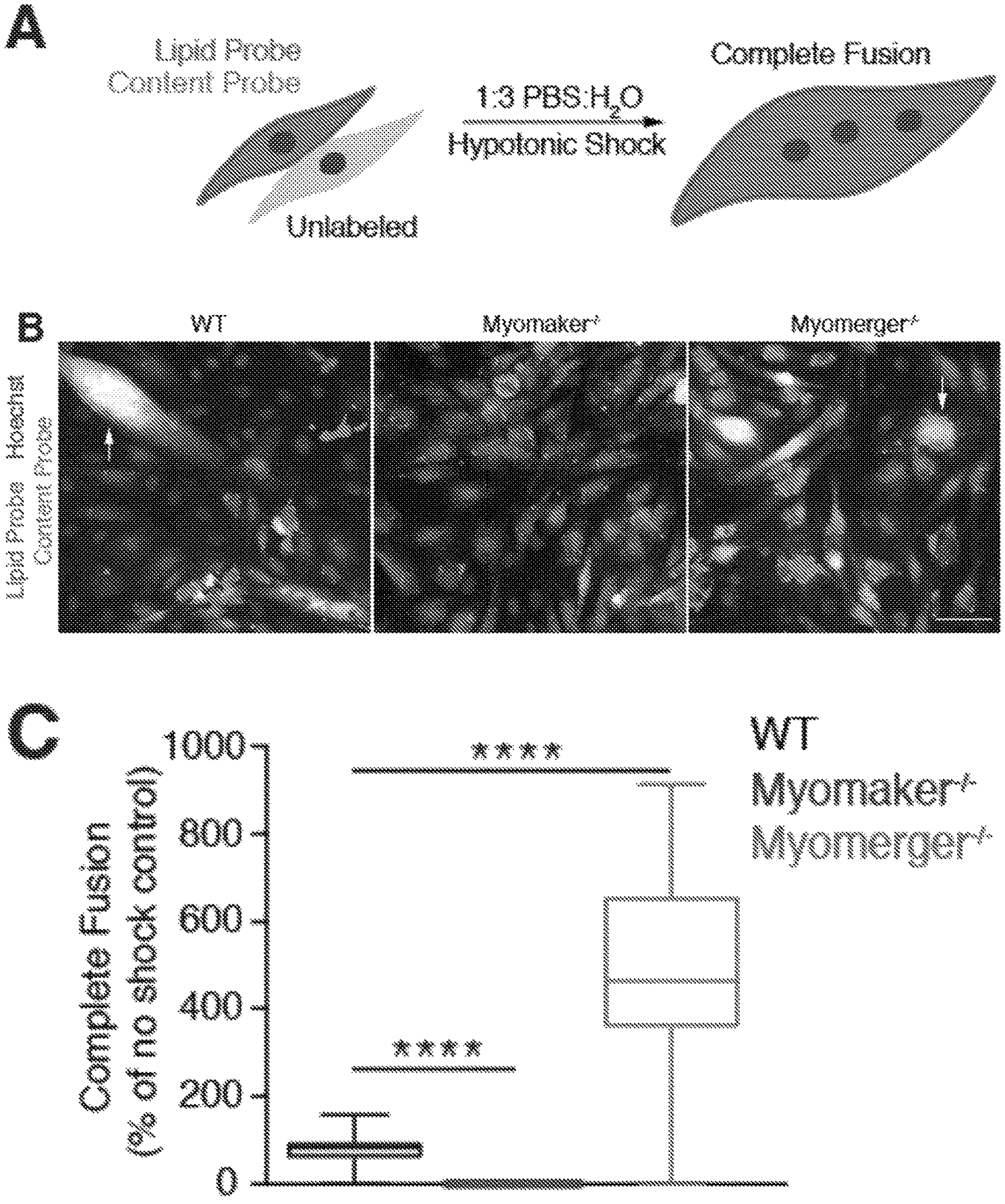
FIG. 2: Compensation of Myomerger deficiency by heterologous membrane-stressing treatments. (A) Schematic illustrating hypotonic shock fusion rescue experiment. Complete fusion is indicated by the presence of multinucleated cells labeled with both lipid and content probes. (B) Representative images of WT, Myomaker$^{-/-}$ and Myomerger$^{-/-}$ C2C12 cells differentiated for 48 hours, labeled with appropriate probes and plated in differentiation medium for 24 hours, then treated with PBS:$H_2O$ (1:3) (hypotonic shock) for 60 seconds. (C) Quantification of complete fusion (n=3 independent experiments) as a percentage of cells of the same genotype that did not receive hypotonic shock. Myomerger$^{-/-}$ C2C12 myoblasts showed an increase in fusion when treated with hypotonic shock. (E) Treatment with Octyl-β-Glucoside (OG) on day 3 of differentiation (Diff.) induced fusion in Myomerger$^{-/-}$ myoblasts (arrows) but not in Myomaker$^{-/-}$ C2C12 myoblasts. (G) Treatment with Magainin 2 (Mag2) for 20 hours on day 3 of differentiation induced myotube formation in Myomerger$^{-/-}$ C2C12 myoblasts (arrows) but had no effect on Myomaker$^{-/-}$ cells. For (E) and (G) the cells were immunostained with myosin antibodies to identify differentiated muscle cells and Hoechst dye was used as a nuclear stain. (H) The percentage of myosin+ cells that contain 3 or nuclei after treatment with OG (n=3 independent experiments) or Mag2 (n=4 independent experiments) as an indicator of fusogenicity. Statistical analyses and data presentation: (C), (H), two tailed Student's t-test; box-and-whisker plots show median (center line), 25th-75th percentiles (box) and minimum and maximum values (whiskers); $^{*}P<0.001$,$^{**}P<0.0001$. Scale bars, 50 μm. See also (D), (F), (I), and (J).
Figure 2:
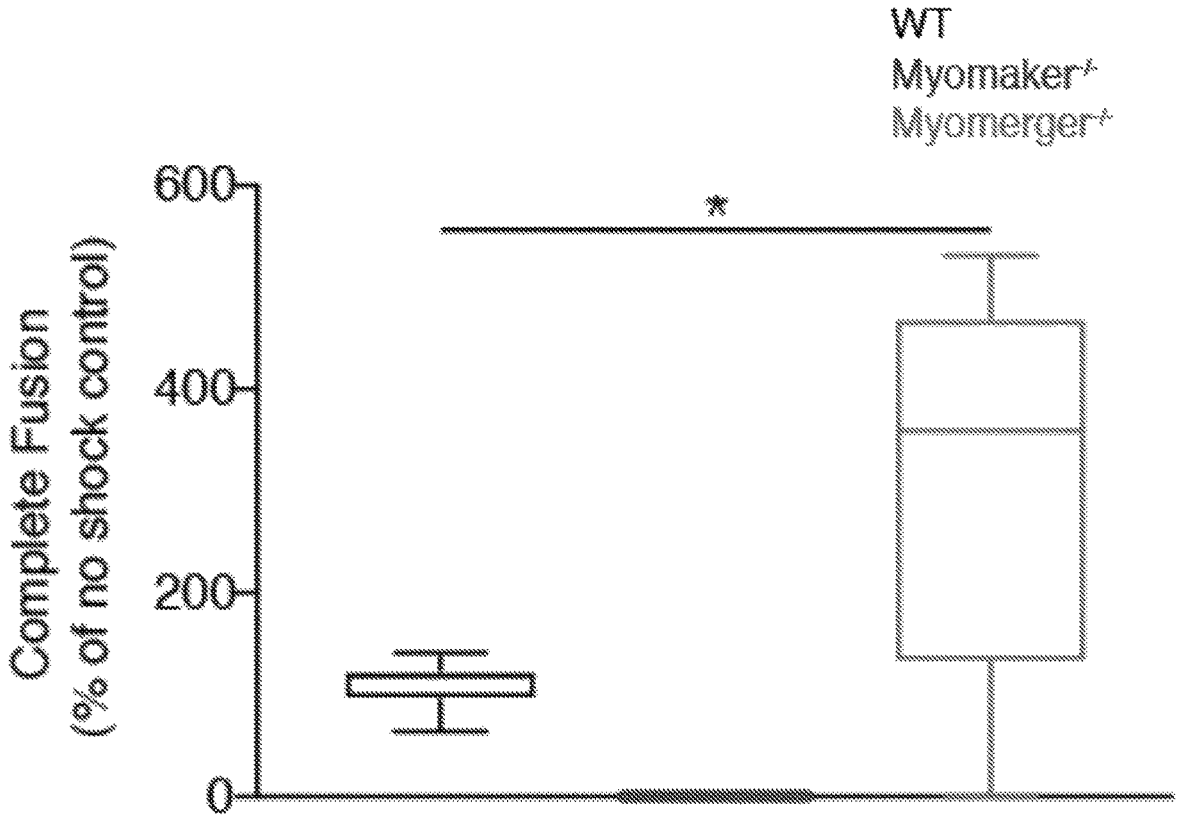
Figure 2:
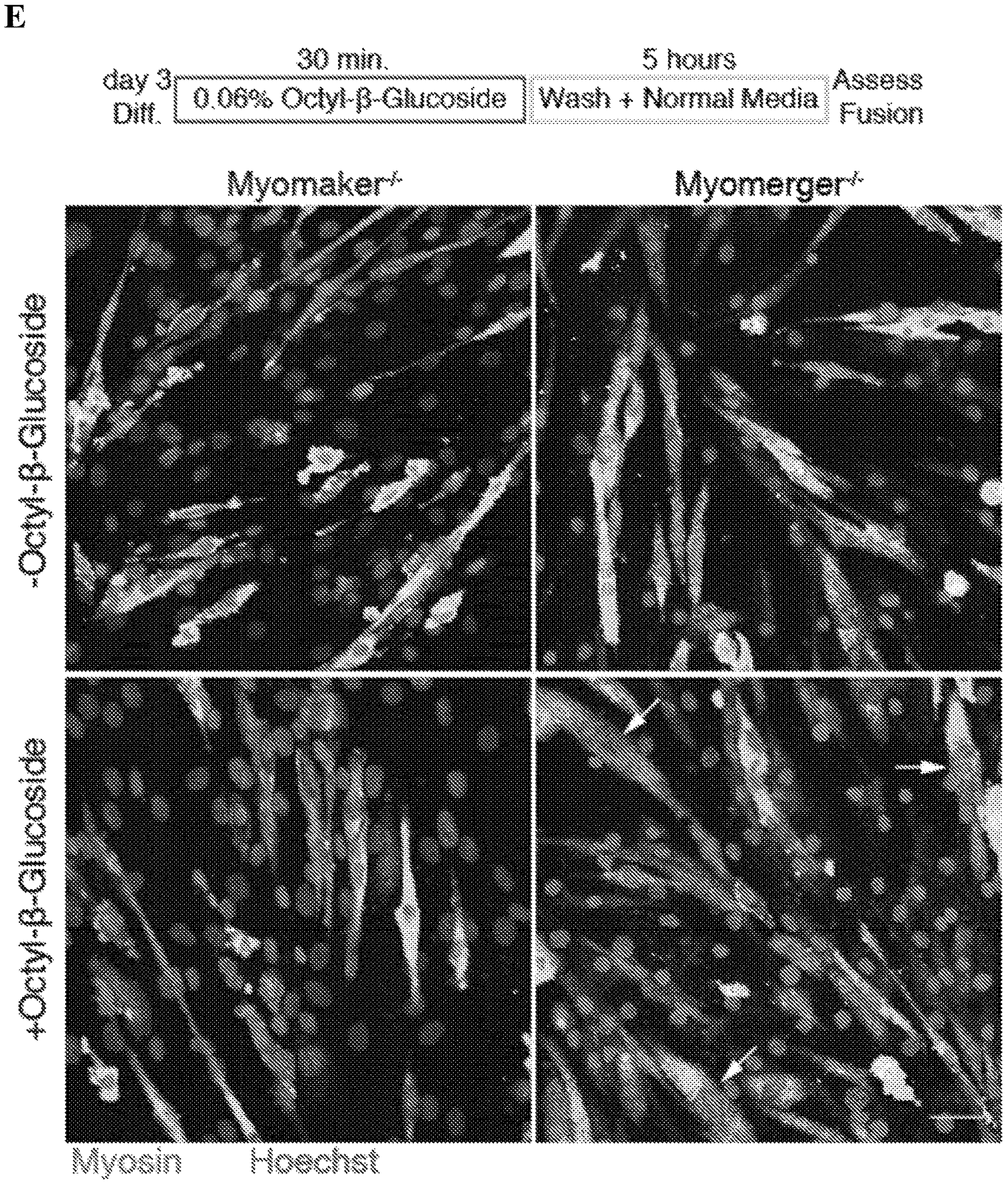
Figure 2:
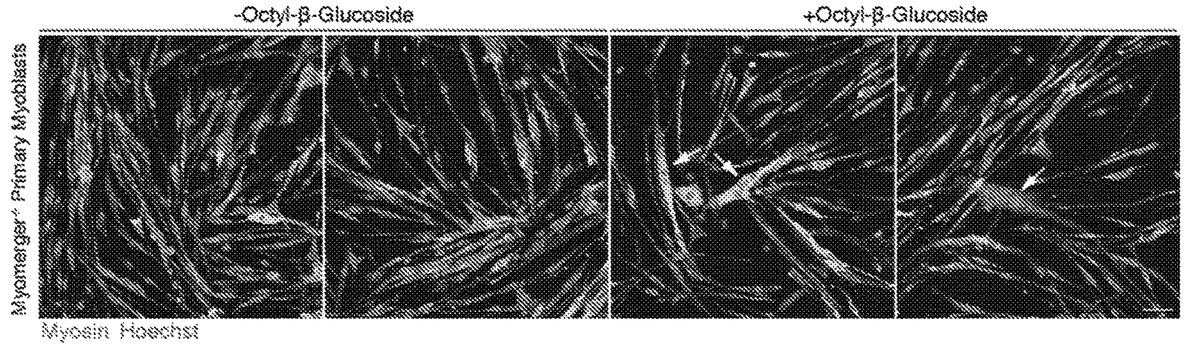
Figure 2:
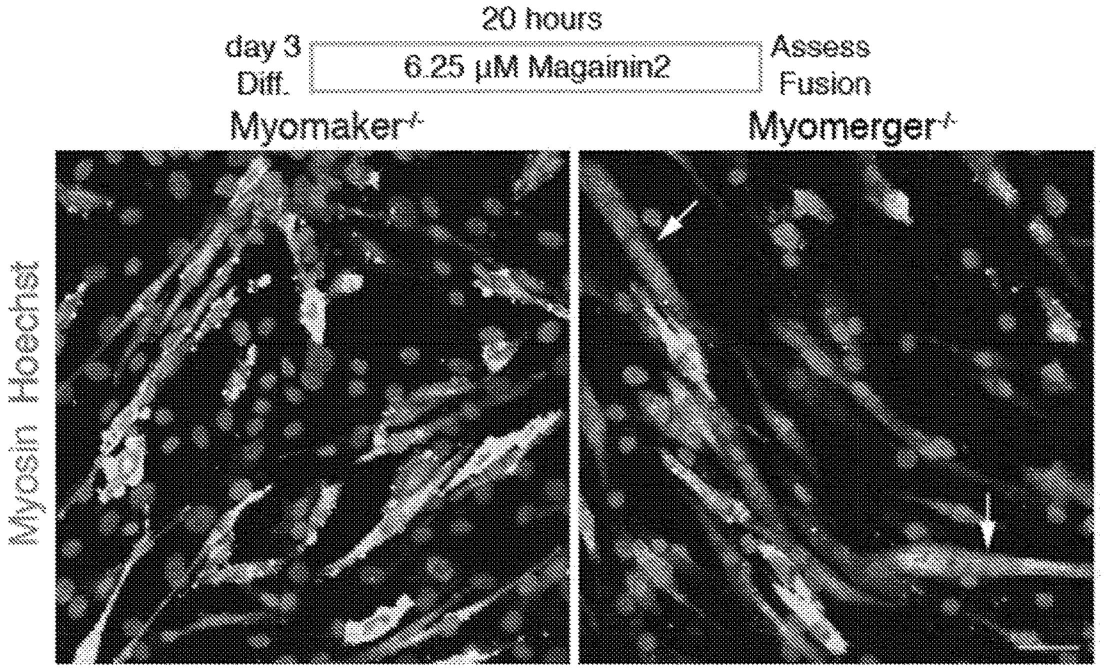
Figure 2:
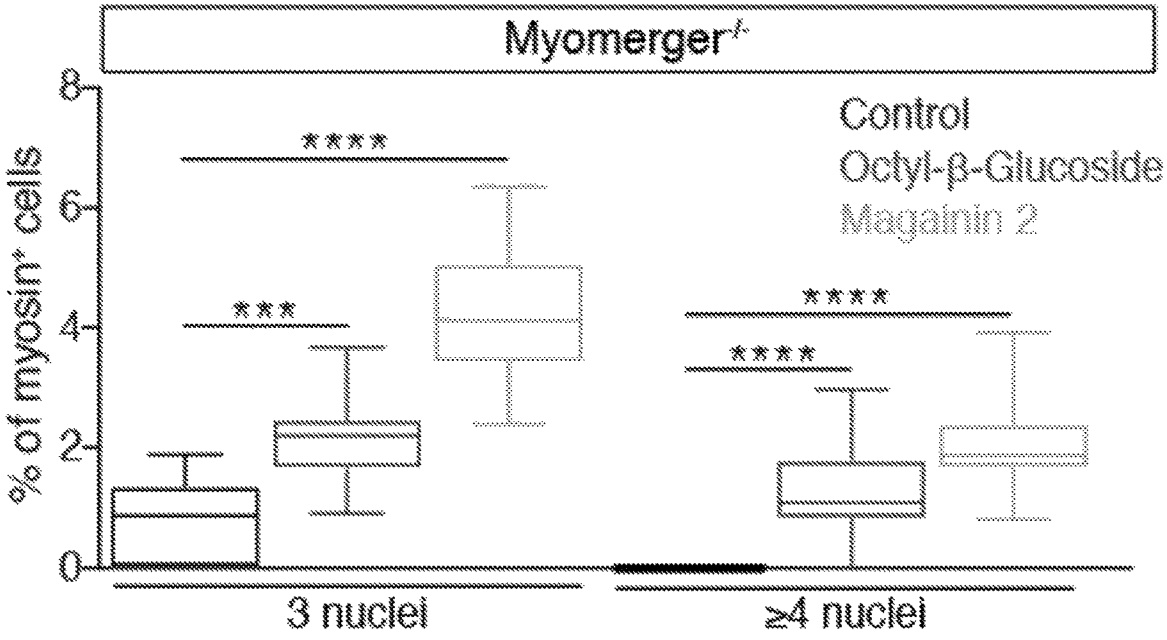
Figure 2:
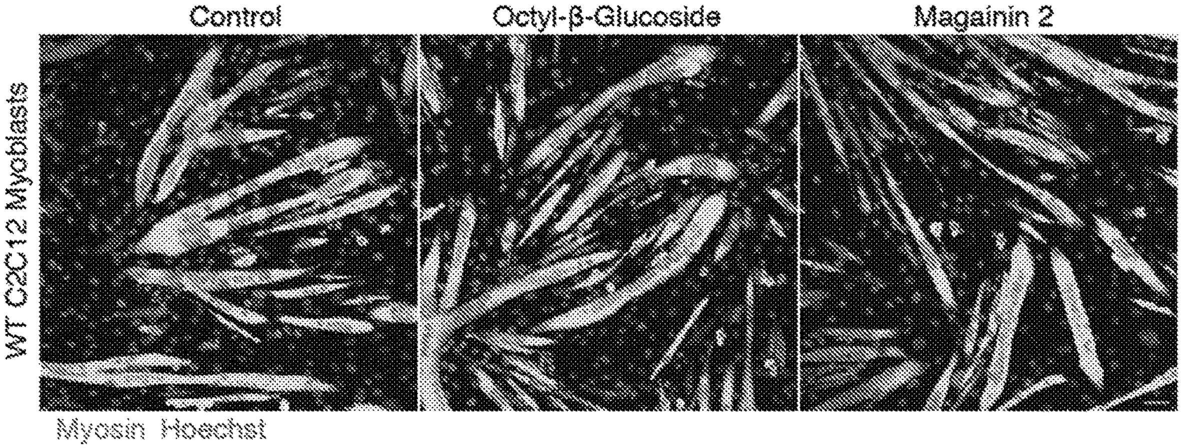
Figure 2:
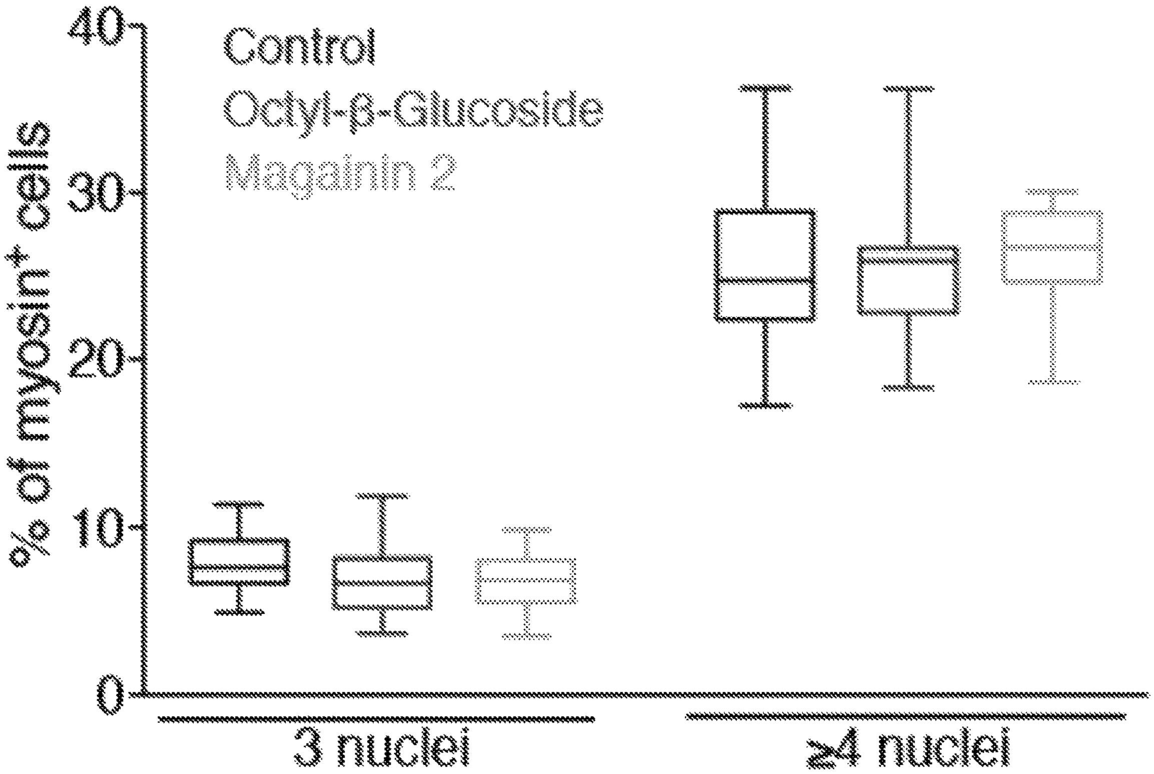

To probe the mechanisms underlying the involvement of Myomerger in pore formation, we developed multiple strategies to functionally compensate for Myomerger deficiency. In our first approach, we subjected the cells to hypotonic osmotic shock. Cell swelling generates tension and stress on the membrane lipid bilayer, and is a method that can force cell fusion completion if hemifusion connections are already present. We differentiated WT, $Myomaker^{-/-}$, and $Myomerger^{-/-}$ myoblasts for 48 hours, labeled them with lipid and content probes and co-plated the labeled cells with unlabeled cells for 24 hours in differentiation medium to allow establishment of hemifusion connections. Then the cells were treated with a hypotonic buffer (1:3 PBS:Water) for 60 seconds (FIG. 2A). Hypotonic shock had no detectable effect on myotube formation in WT cultures confirming that all hemifusion events in these cells advanced to complete fusion. Myomaker$^{-/-}$ cells did not respond to hypotonic shock confirming the lack of hemifusion connections in Myomaker-deficient myoblasts (FIG. 2B). In contrast, complete fusion was observed in Myomerger$^{-/-}$ cells after hypotonic shock further indicating that hemifusion connections are present in these cells (FIG. 2B and FIG. 2C). Similarly, hypotonic shock induced fusion of Myomerger null primary myoblasts (FIG. 2D).

Since the mechanism by which hypotonic shock resolves hemifusion connections is through global membrane bilayer stress, we also tested if more subtle modifications of membrane bilayer could drive fusion. We found that fusion of Myomerger-deficient myoblasts can be rescued by the detergent Octyl-β-Glucoside (OG) and by the anti-microbial peptide Magainin 2 (Mag2), both directly interact with the lipid bilayer and generate membrane stresses that cause permeabilization. We applied OG to differentiated Myomaker$^{-/-}$ and Myomerger myoblasts for 30 minutes and then washed the cells. Fusion was assessed 5 hours after the treatment. We found that Myomaker$^{-/-}$ cells treated with OG did not fuse, but we observed obvious fusion events in Myomerger$^{-/-}$ cells (FIG. 2E). The ability of OG to compensate for loss of Myomerger was confirmed in primary myoblasts (FIG. 2F). Application of Mag2 also partially rescued fusion of Myomerger$^{-/-}$ myoblasts. Fusion was increased in Myomerger$^{-/-}$, but not Myomaker$^{-/-}$, myoblasts after 20 hours of incubation with Mag2 (FIG. 2G). The ability of OG and Mag2 to increase fusion was quantified by analyzing the percentage of myosin$^{+}$ (a marker of muscle differentiation) cells with 3 or ≥4 nuclei. OG and Mag2 not only increased the percentage of cells with 3 nuclei but also induced formation of myotubes with ≥4 nuclei (FIG. 2H). OG or Mag2 did not have an effect on fusion of C2C12 myoblasts (FIGS. 2I and 2J), revealing that WT cells are likely maximally efficient at converting hemifusion to full fusion thus the reaction does not stall at intermediate stages.

The extent of fusion rescue for Myomerger$^{-/-}$ myoblasts above did not reach WT levels. We hypothesized that the magnitude of rescue could be limited by the transient character of hemifusion intermediates. Myoblast fusion is a relatively slow process where many multinucleated myotubes form over multiple days. Thus, at any given time there are a finite number of hemifusion connections. These connections appear to be energy intensive structures that, if not converted into complete fusion, likely dissociate within minutes. We reasoned that the treatments promoting hemifusion-to-fusion transition for the myomerger-deficient myoblasts could be more effective if applied to cells undergoing synchronized fusion. WT, Myomaker$^{-/-}$, or Myomerger$^{-/-}$ C2C12 myoblasts, labeled with either green cell tracker or orange cell tracker, were differentiated for 48 hours and then the reversible hemifusion inhibitor lysophosphatidylcholine (LPC) was applied for 16 hours in differentiation medium (LEIKINA et al. (2013) "Extracellular annexins and dynamin are important for sequential steps in myoblast fusion" J Cell Biol, Vol. 200, pp. 109-123, which is herein incorporated by reference in its entirety) (FIG. 3A). At the time of LPC removal, we treated the cells with either hypotonic medium (1:3 PBS:$H_2O$) or chlorpromazine (CPZ), which is to induce hemifusion-to-fusion transition, for 60 seconds. The percentage of nuclei in multinucleated cells was assayed as syncytium formation 30 minutes after LPC removal. We compared these treatments to uninterrupted fusion where myoblasts were not exposed to LPC (Control (-LPC)) (FIG. 3A). Application of either hypotonic shock or CPZ had little effect on fusion of WT myoblasts (FIGS. 3B and 3C). This indicates that hemifusion intermediates in WT cells effectively advance to complete fusion without further treatments, reinforcing the absence of stalled intermediates in WT cells. No fusion was observed for Myomaker$^{-/-}$ cells in the absence of LPC or after treatment the LPC-synchronized cells with hypotonic shock or CPZ, confirming that these cells do not hemifuse (FIGS. 3B and 3C). Finally, synchronized Myomerger$^{-/-}$ myoblasts subjected to either hypotonic shock or CPZ reached fusion levels observed for WT myoblasts (FIG. 3C). A robust rescue of fusion in these experiments by treatments promoting hemifusion-to-fusion transition demonstrates that the lack of Myomerger does not appear to impact the efficiency of hemifusion and that Myomaker does not appear to involve Myomerger to establish hemifusion connections capable of being transitioned to full fusion. Moreover, pleiotropic membrane stresses that promote pore formation appear to compensate for loss of Myomerger.

Myomerger Contains a C-Terminal Ectodomain that Appears to Function from Outside the Cell.

Figure 4:
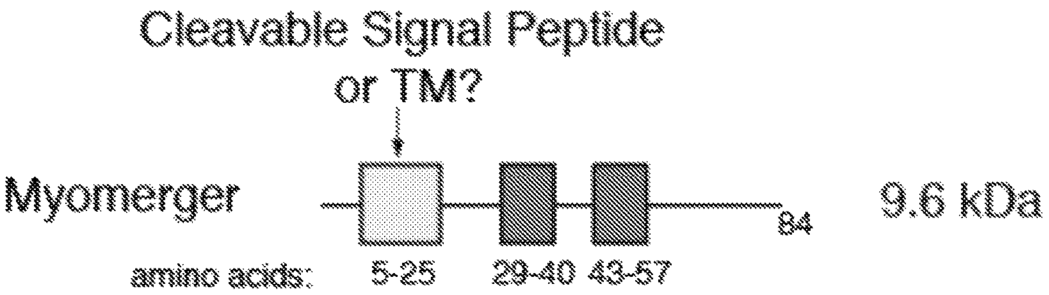
FIG. 4: The C-terminal ectodomain of Myomerger appears to function from outside the cell. (H) Immunoblot for Myomerger from the surface biotinylated fraction (IP: Streptavidin) and total lysates (input) from differentiated C2C12 myoblasts. Cells not treated with biotin were used as a control. Absence of the cytosolic protein (Tubulin) from the biotinylated fraction confirms surface-specific labeling. Data shown is representative from 3 independent experiments. (I) Schematic of the synchronized fusion assay. Myoblasts that had been differentiated for 48 hours were labeled with either DiI (lipid probe) or green cell tracker (content probe). Addition of LPC accumulates myoblasts that are ready-to-fuse and removal of LPC (LPC/Wash) allows cells to undergo hemifusion and complete fusion. Antibodies to Myomerger ectodomain, or IgG as a control, were added during this wash phase. (J) Quantification of synchronized fusion for WT C2C12 (n=3 independent experiments) myoblasts was achieved by assessing formation of mononucleated cells with both membrane and content probes (hemifusion, left) and multinucleated myotubes (complete fusion, right). (O) Incubation of rMBP-Myomerger$^{26-84}$ for 20 hours in differentiation media induces fusion of Myomerger$^{-/-}$ (arrows), but not Myomaker$^{-/-}$ C2C12 myoblasts. Cultures were immunostained with myosin antibodies to identify differentiated muscle cells and Hoechst dye was used as a nuclear stain. (P) The percentage of myosin$^{+}$ cells that contain 3 or ≥4 nuclei after incubation with rMBP or rMBP-Myomerger$^{26-84}$ (n=4 independent experiments with two independent protein purifications) at various concentrations of recombinant protein. Statistical analyses and data presentation: (J), (P), Mann-Whitney test; box-and-whisker plots show median (center line), 25th-75th percentiles (box) and minimum and maximum values (whiskers); $^{*}P<0.05$, $^{}P<0.01$,$^{*}P<0.001$, $^{****}P<0.0001$. Scale bar, 50 μm. See also (A)-(G) and (K)-(N).
Figure 4:
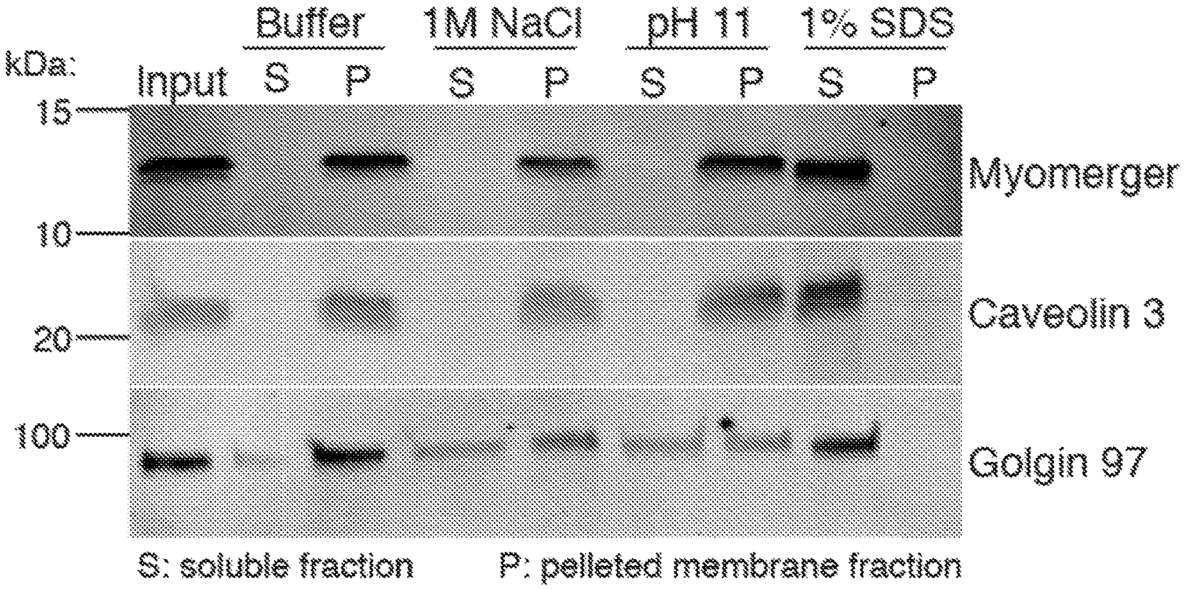
Figure 4:
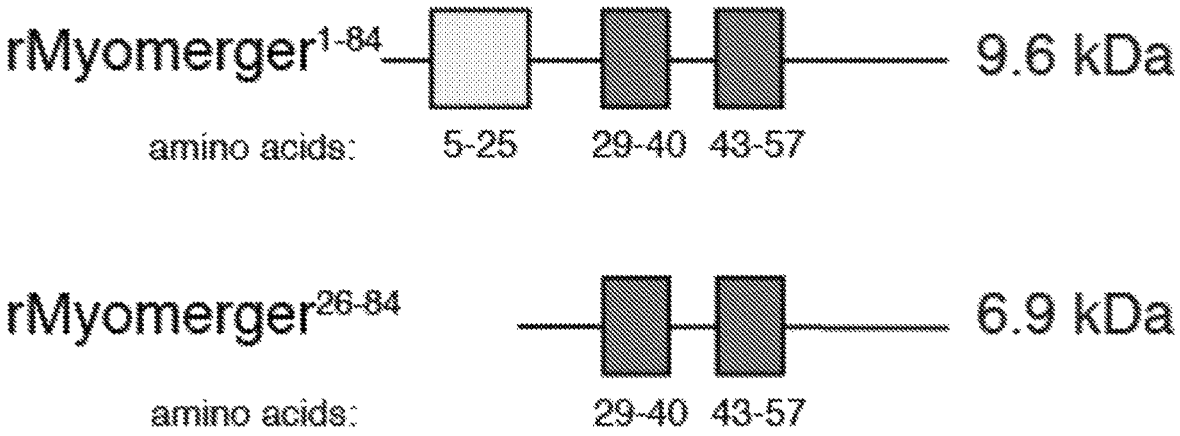
Figure 4:
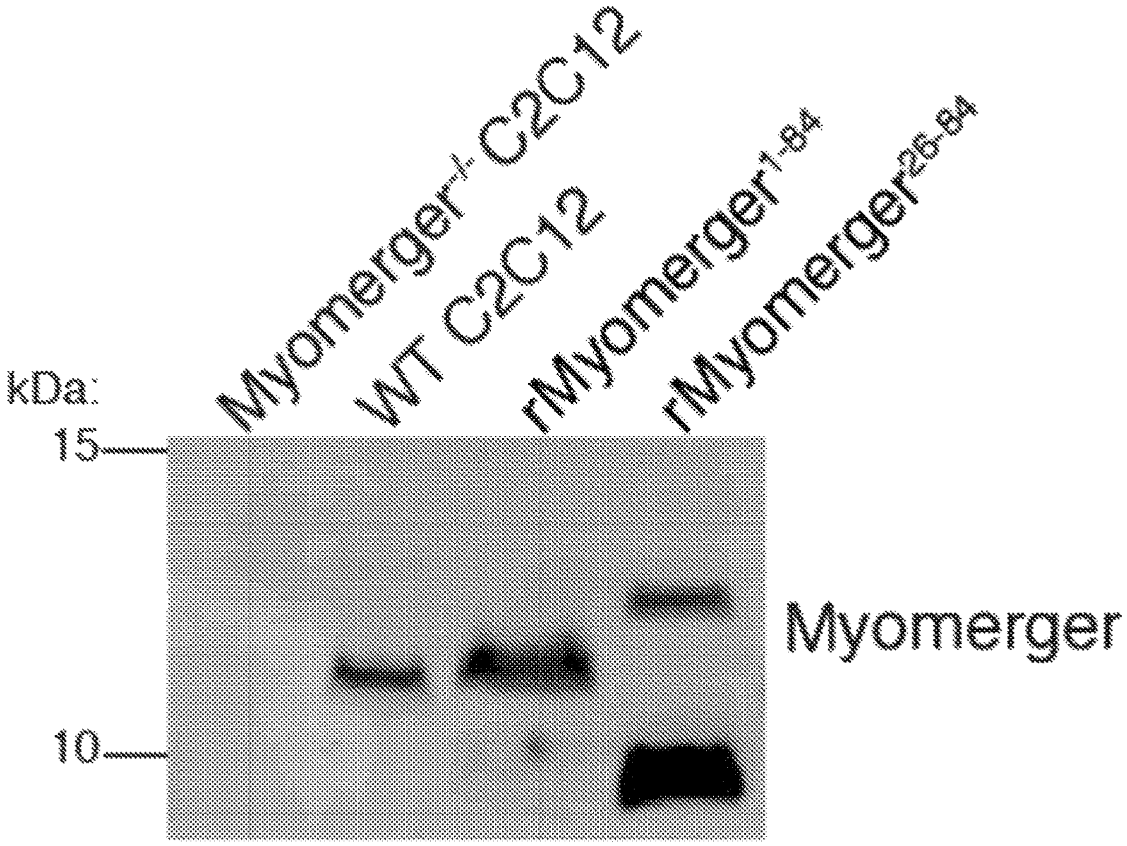
Figure 4:
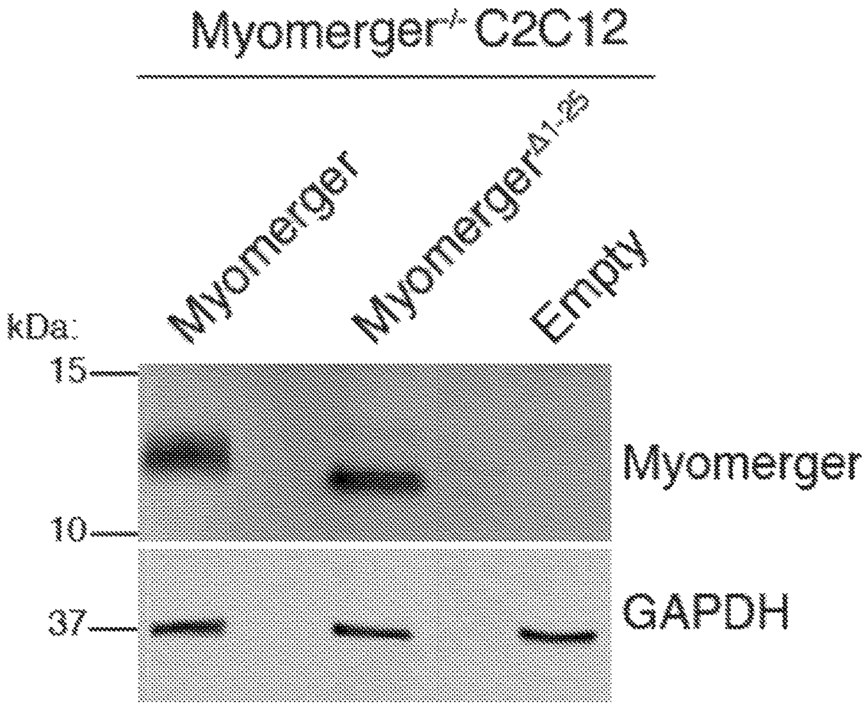
Figure 4:
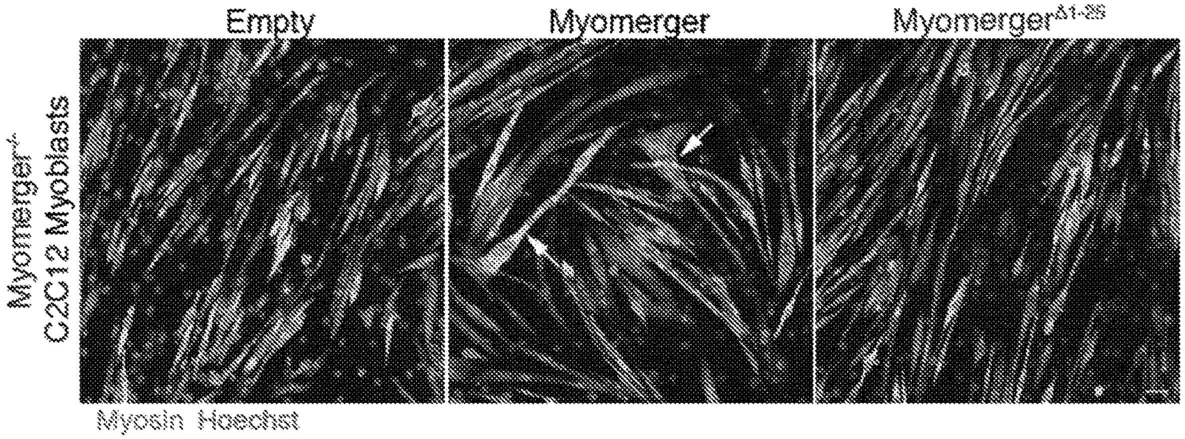
Figure 4:
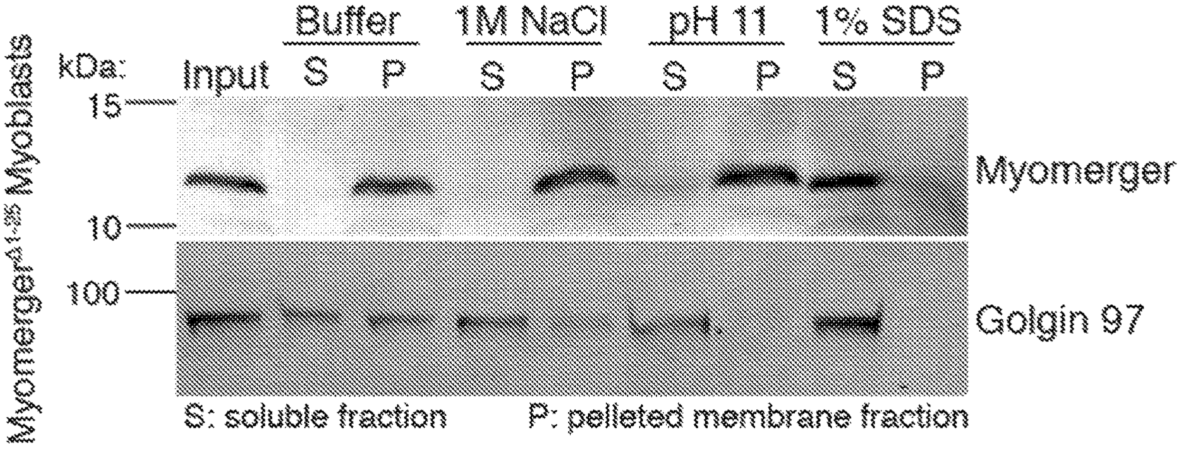
Figure 4:
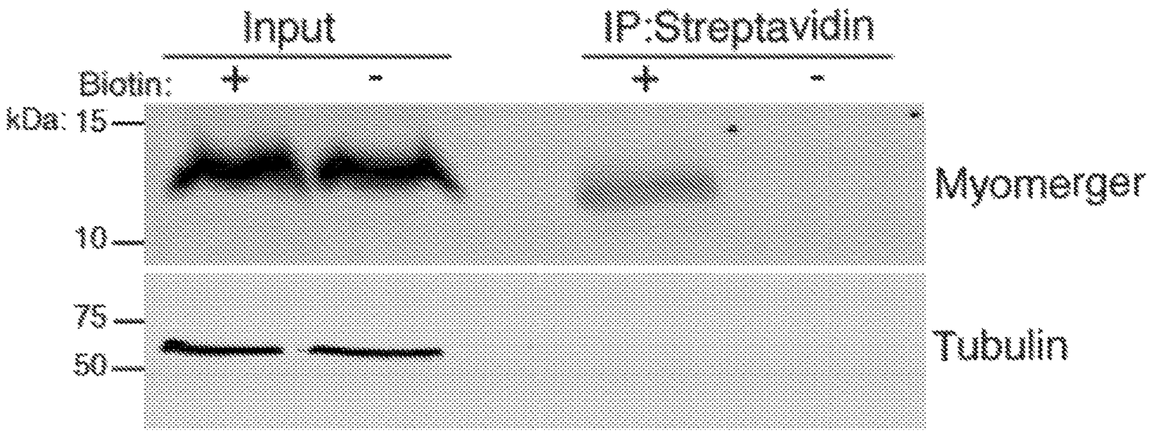
Figure 4:
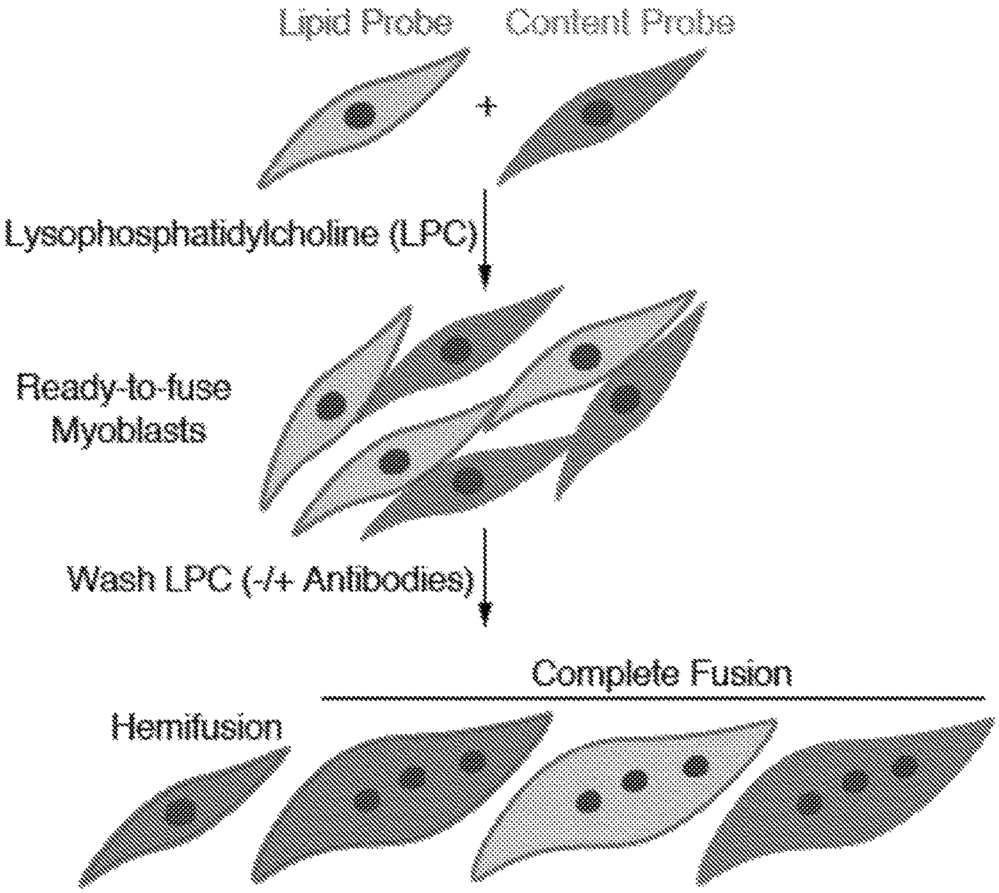
Figure 4:
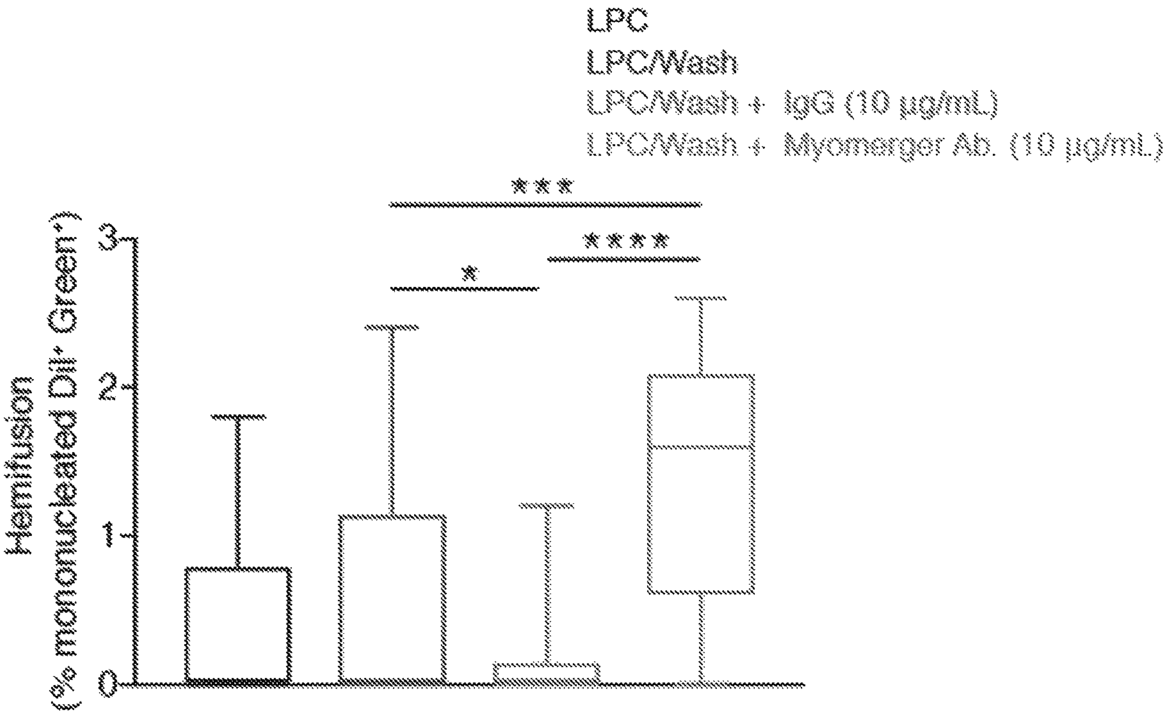
Figure 4:
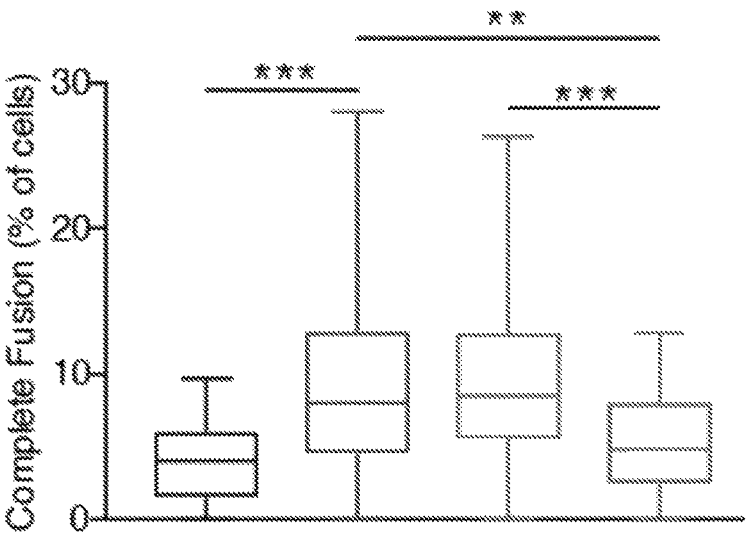
Figure 4:
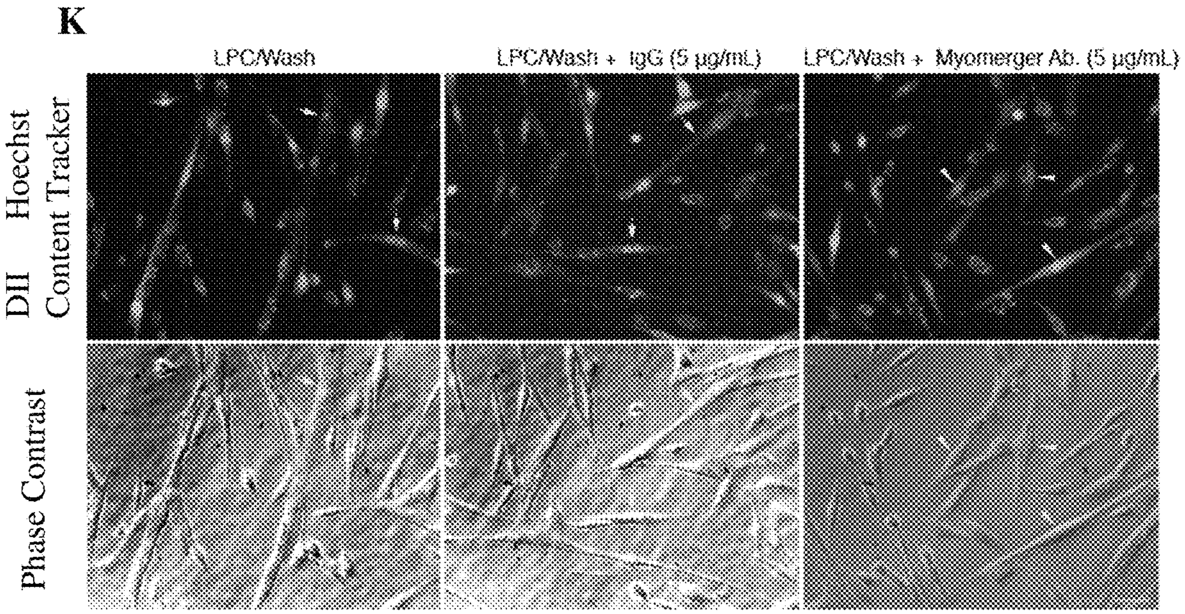
Figure 4:
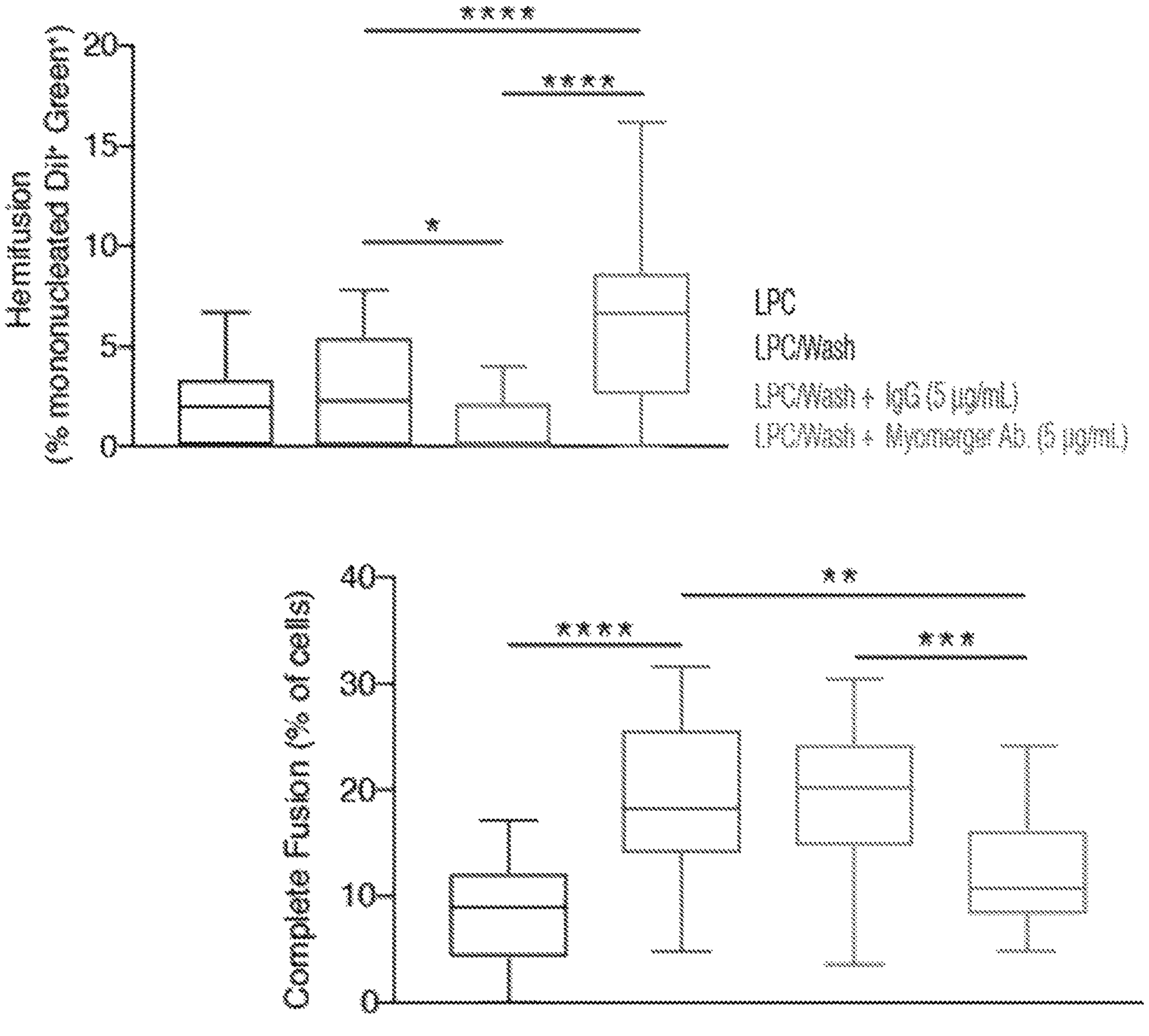
Figure 4:
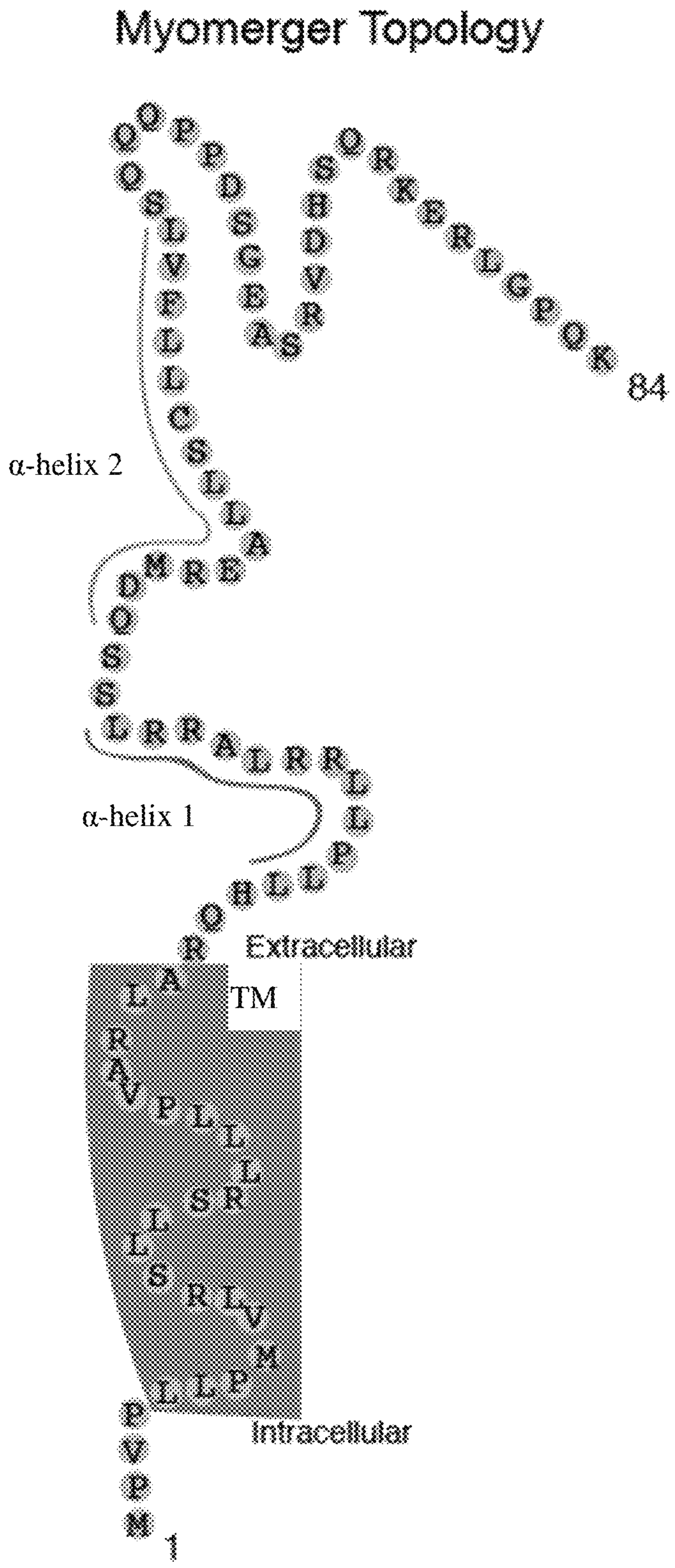
Figure 4:
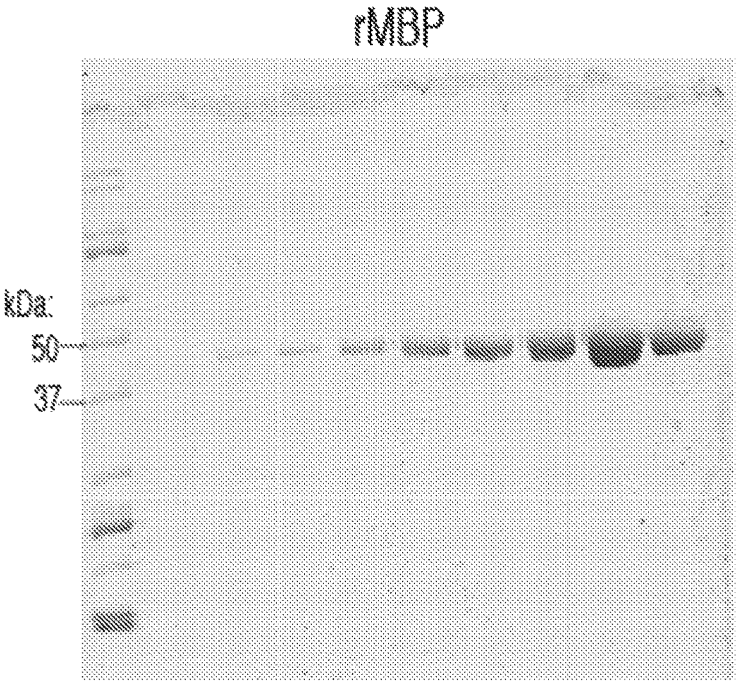
Figure 4:
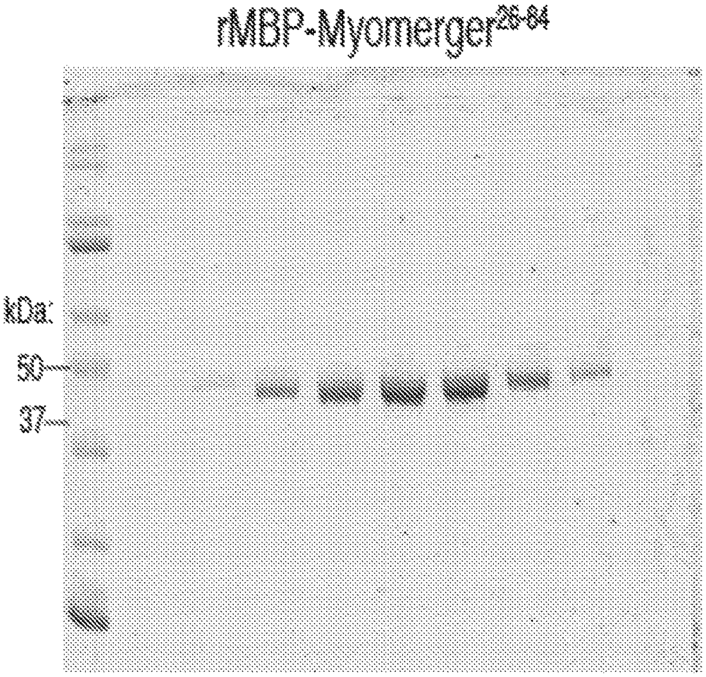
Figure 4:
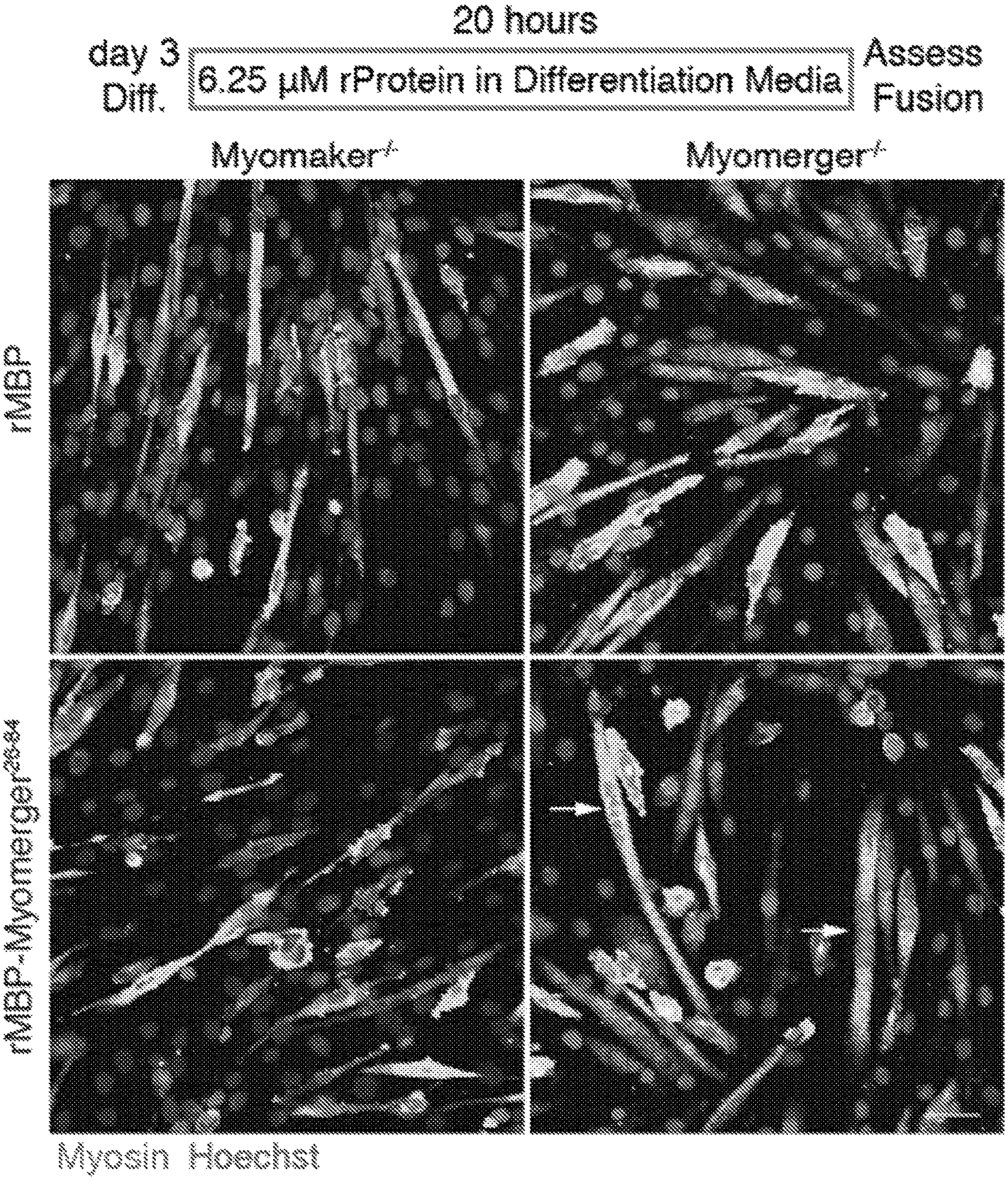
Figure 4:
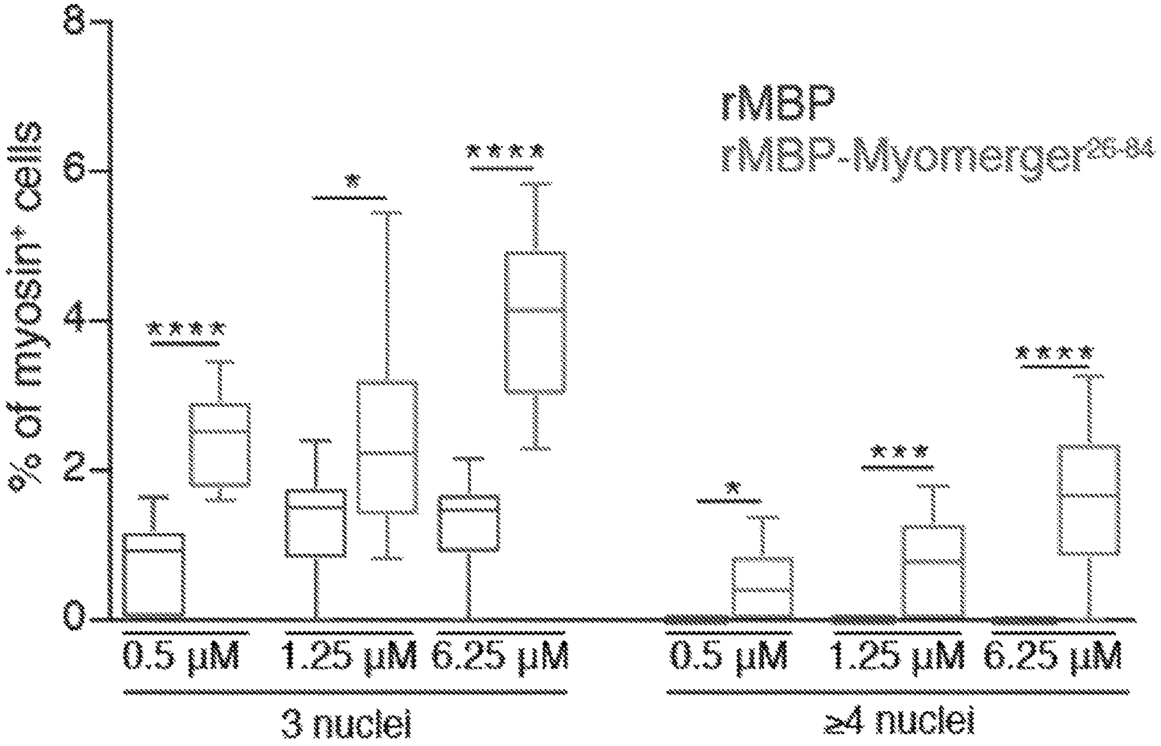

We next sought to understand the mechanisms by which Myomerger drives fusion completion. Myomerger contains three conserved α-helical domains that could presumably interact with a membrane, and the second helix is highly conserved suggesting a conserved function. In contrast to the downstream helical domains (amino acids 29-40 and 43-57), the N-terminal is-helix of Myomerger (amino acids 5-25) is long enough to span the bilayer (FIG. 4A). To test if Myomerger is an integral membrane protein we fractionated membranes from WT C2C12 myoblasts on day 2 of differentiation. Membrane fractions were then incubated with either low salt buffer, high salt buffer (1M NaCl), alkaline buffer (pH11), or detergent (1% SDS), followed by centrifugation and assessment of membrane and soluble fractions by western blot. While high salt and alkaline buffers solubilized the peripheral membrane protein Golgin 97, Myomerger remained with the pelleted membrane fraction (FIG. 4B). Myomerger was only solubilized with detergent indicating that this protein is tightly associated with the membrane. To confirm the N-terminal region is not a signal sequence cleaved during protein processing, we expressed a full-length Myomerger (rMyomerger$^{1-84}$) protein and a Myomerger protein lacking the N-terminal region (rMyomerger$^{26-84}$) in *E. coli* (FIG. 4C). Comparison of these proteins to WT C2C12 lysates by western blotting for Myomerger revealed that endogenous Myomerger migrates at a size similar to rMyomerger$^{1-84}$, whereas rMyomerger$^{26-84}$ runs at a lower molecular weight (FIG. 4D).

To assess the functional importance of the N-terminal helical region we generated a mutant where amino acids 5-25 of Myomerger were replaced with a cleavable synthetic signal sequence from HA. We expressed this mutant (Myomerger$^{\Delta 1-25}$) or WT Myomerger in Myomerger$^{-/-}$ myoblasts. While WT Myomerger and Myomerger$^{\Delta 1-25}$ were expressed at similar levels (FIG. 4E), only WT Myomerger was able to rescue fusion (FIG. 4F). Isolation of membrane fractions showed that Myomerger$^{\Delta 1-25}$ also associated with membranes (FIG. 4G), suggesting that the N-terminal region of Myomerger does not appear to be involved for membrane attachment but could be helpful for orientation of the protein in the membrane or localization to the proper domain. These data establish that the N-terminal α-helical region of Myomerger is helpful for function when endogenously expressed.

An association between membranes and Myomerger leads to the question of which cellular membrane compartment contains this protein. If the protein functions in membrane events that drive fusion it might be expected to be present on the plasma membrane. We labeled proteins at the surface of WT C2C12 cells with a cell-impermeable biotinylation reagent and then immunoprecipitated biotinylated proteins with streptavidin. Immunoblotting of the isolated proteins with Myomerger antibodies showed that Myomerger is normally expressed on the cell surface and suggested that the non-transmembrane region of Myomerger is extracellular (FIG. 4K).

To verify that Myomerger-membrane interactions promote fusion rather than some pre-fusion stages, we employed the synchronized fusion assay described above. We labeled one population of WT C2C12 myoblasts with a lipid probe (DiI) and the other with a content probe (green cell tracker) and accumulated ready-to-fuse C2C12 cells in the presence of LPC. 30 minutes after replacing LPC-supplemented differentiation medium with normal differentiation medium (LPC/Wash) we measured fusion by the syncytium formation assay and hemifusion by the lipid mixing assay that assesses the appearance of mononucleated double-labeled cells (FIG. 4I). Myomerger or non-specific control IgG antibodies were applied at the time of LPC removal. LPC removal (LPC/Wash) resulted in an increase in complete fusion relative to that observed in the control experiment in which LPC was not removed (LPC) (FIG. 4J). Removal of LPC did not increase the numbers of hemifused cells beyond the background level observed in the presence of LPC reflecting efficiency of hemifusion-to-fusion transition for WT myoblasts. Control non-specific IgG applied at the time of LPC removal had a minor effect on hemifusion but no apparent impact on complete fusion (FIG. 4J). We interpret the minor effect on hemifusion to be due to non-specific binding of IgG antibodies, which could sterically hinder per hemifusion. In contrast to control IgG, application of Myomerger antibodies that recognize the region of the protein after amino acid 25, reduced the number of complete fusion events (FIG. 4J). These antibodies also increased the number of cells scored as hemifused at 30 minutes after LPC removal but, possibly, advancing to complete fusion at later time. The synchronized fusion assay on WT primary myoblasts with Myomerger antibodies also revealed an increase in the number of hemifused cells and decrease in the number of complete fusion events in the presence of Myomerger antibodies, confirming a prominent role for cell surface Myomerger in fusion pore formation (FIG. 4K and FIG. 4L).

Taken together, our data suggest a topology model for Myomerger where the N-terminal helical region is embedded in the plasma membrane and the short helical regions are extracellular (FIG. 4M). That the N-terminal mutant (Myomerger$^{\Delta 1\text{-}25}$) tracks with membrane fractions (FIG. 4G) suggests that the short extracellular helical regions may interact with the outer layer of the plasma membrane. To explore this model further, we purified the ectodomain of Myomerger and tested its ability to rescue fusion of Myomerger null myoblasts. We expressed in *E. coli* the extracellular region of Myomerger (amino acids 26-84 of the mouse protein) linked to maltose binding protein (MBP) to improve solubility. MBP or MBP-Myomerger$^{26\text{-}84}$ were purified to 95% homogeneity through an amylose column and size exclusion chromatography (FIG. 4N). We applied rMBP-Myomerger$^{26\text{-}84}$ or rMBP as a control to either Myomaker$^{-/-}$ or Myomerger$^{-/-}$ myoblasts for 20 hours on day 3 of differentiation, then assessed fusion. rMBP-Myomerger$^{26\text{-}84}$ had no effect on Myomaker$^{-/-}$ C2C12 myoblasts but promoted fusion of Myomerger$^{-/-}$ myoblasts indicating that myoblast fusion depends on the interactions between the ectodomain of Myomerger and the plasma membrane of the myoblasts (FIG. 4O). We performed this experiment with multiple concentrations of rMBP or rMBP-Myomerger$^{26\text{-}84}$ and found that Myomerger ectodomains induce formation of myotubes with 4 or more nuclei (FIG. 4P). These data are consistent with the model that the ectodomain of Myomerger functions from outside the cell to drive completion of the fusion reaction.

Myomerger Appears to Stress Membranes

Figure 5:
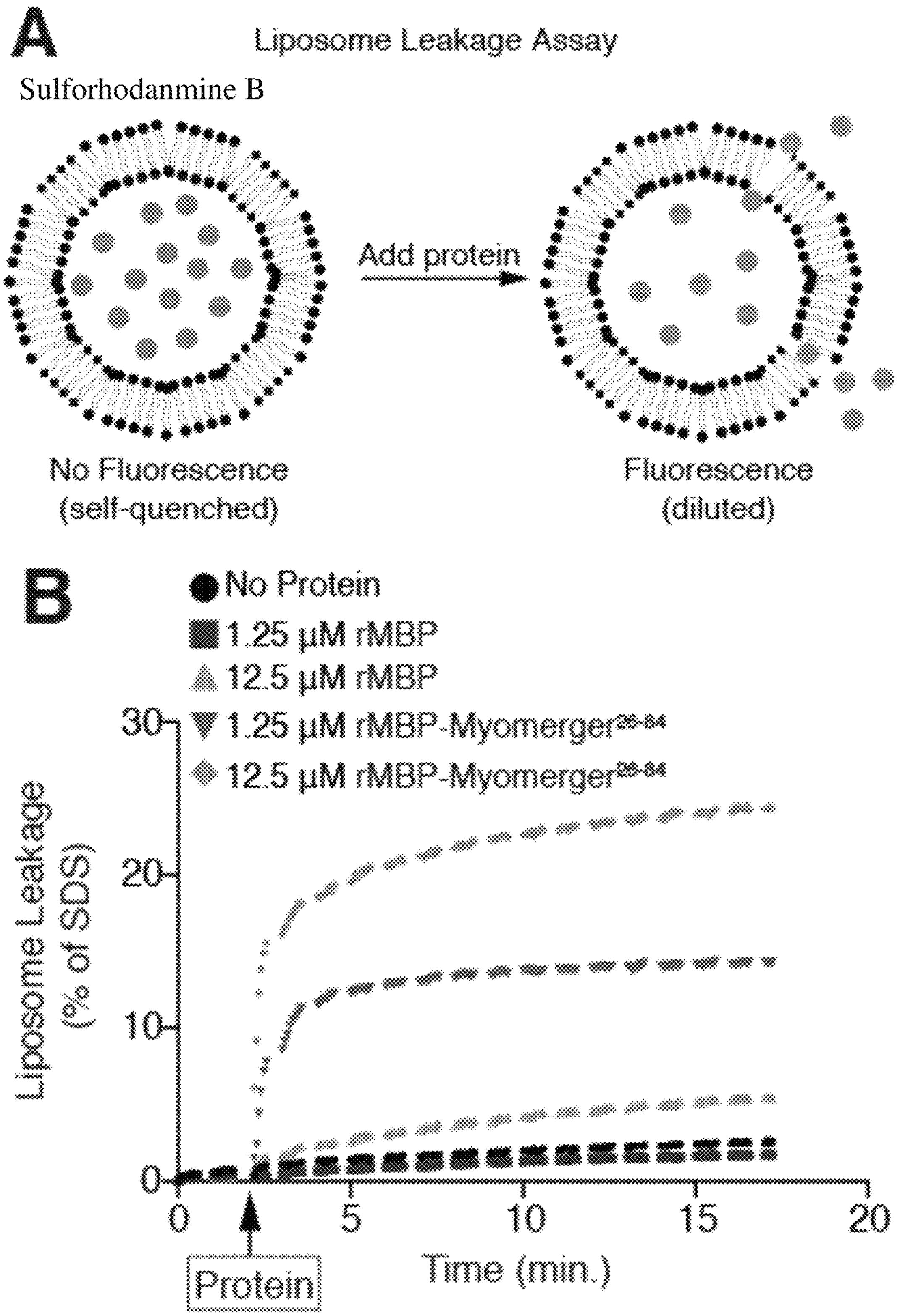
FIG. 5: Myomerger functions to stress membranes. (A) Schematic showing that disruption of the liposome membrane releases self-quenched Sulforhodamine B from the liposomes generating a fluorescence signal. (B) Liposome content release was monitored as an increase in Sulforhodamine B fluorescence and is presented as a percentage of the fluorescence measured after complete dequenching of the fluorescence by SDS application at the end of each experiment. Leakage was observed when liposomes were subjected to rMBP-Myomerger$^{26-84}$ but not to rMBP. (C) Analysis of leakage two minutes after the addition of various concentrations of recombinant protein (n=4 independent experiments with two independent protein purifications and two independent liposome preparations). (I) A permeabilization assay to determine an effect for Myomerger on the plasma membranes of cells. Myoblasts are incubated with water (induces osmotic swelling, membrane tension, and pore(s)) and fluorescent phalloidin (F-actin probe) for 30 seconds and detection of phalloidin$^+$ cells indicates permeabilization. (J) Representative images show phalloidin labeling and Hoechst-labeled nuclei from proliferating WT C2C12 myoblasts and differentiating WT, Myomaker$^{-/-}$, and Myomerger$^{-/-}$ C2C12 myoblasts after hypotonic shock. (K) Quantification of the percentage of phalloidin$^+$ cells from E (n=3 independent experiments). Statistical analyses and data presentation: (C) two-tailed Student's t-test; (K) Mann-Whitney test; (C) mean±standard deviation; (K) box-and-whisker plots show median (center line), 25th-75th percentiles (box) and minimum and maximum values (whiskers); *P<0.05, P<0.01, *P<0.001, ****P<0.0001; Scale bar, 50 μm. See also (D)-(H).
Figure 5:
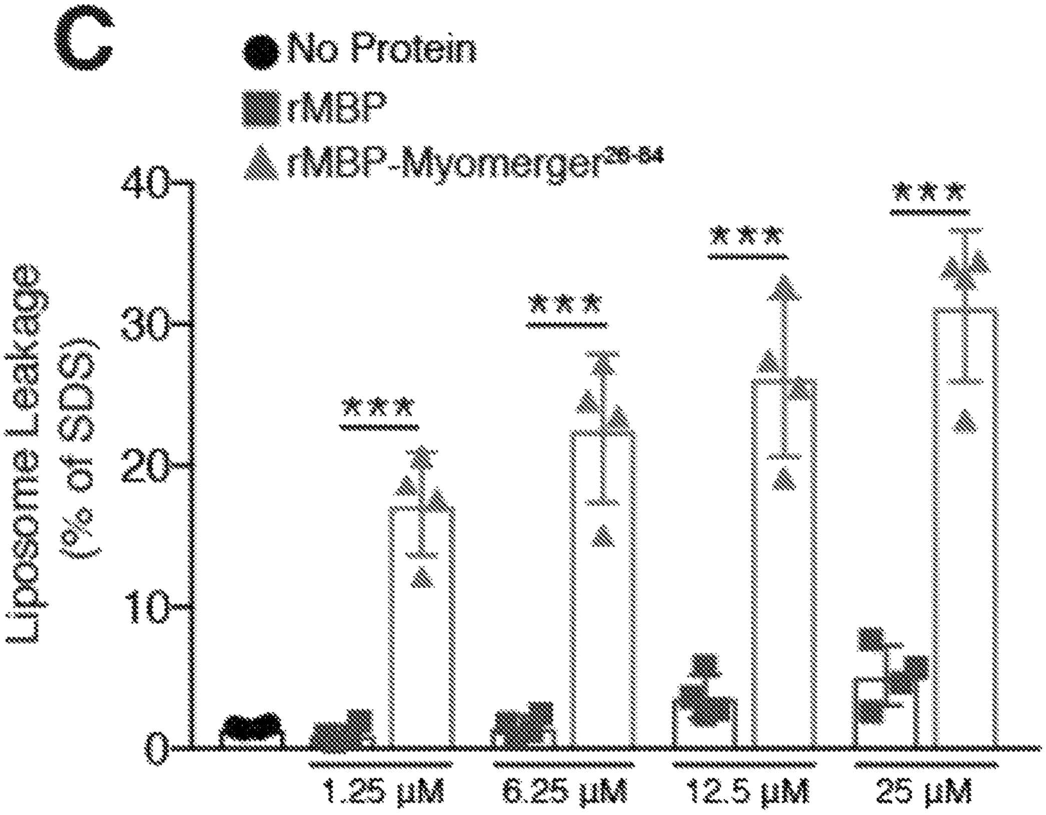
Figure 5:
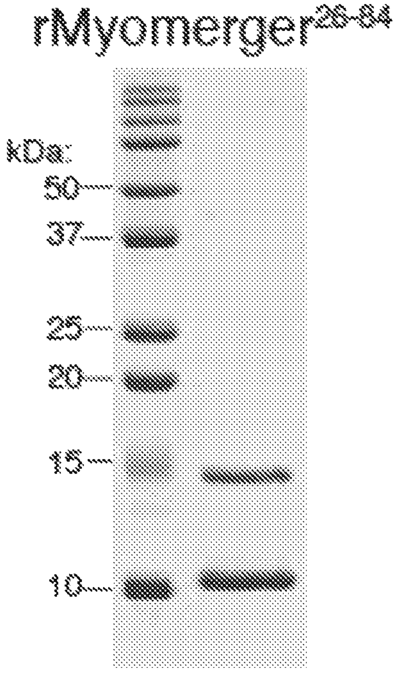
Figure 5:
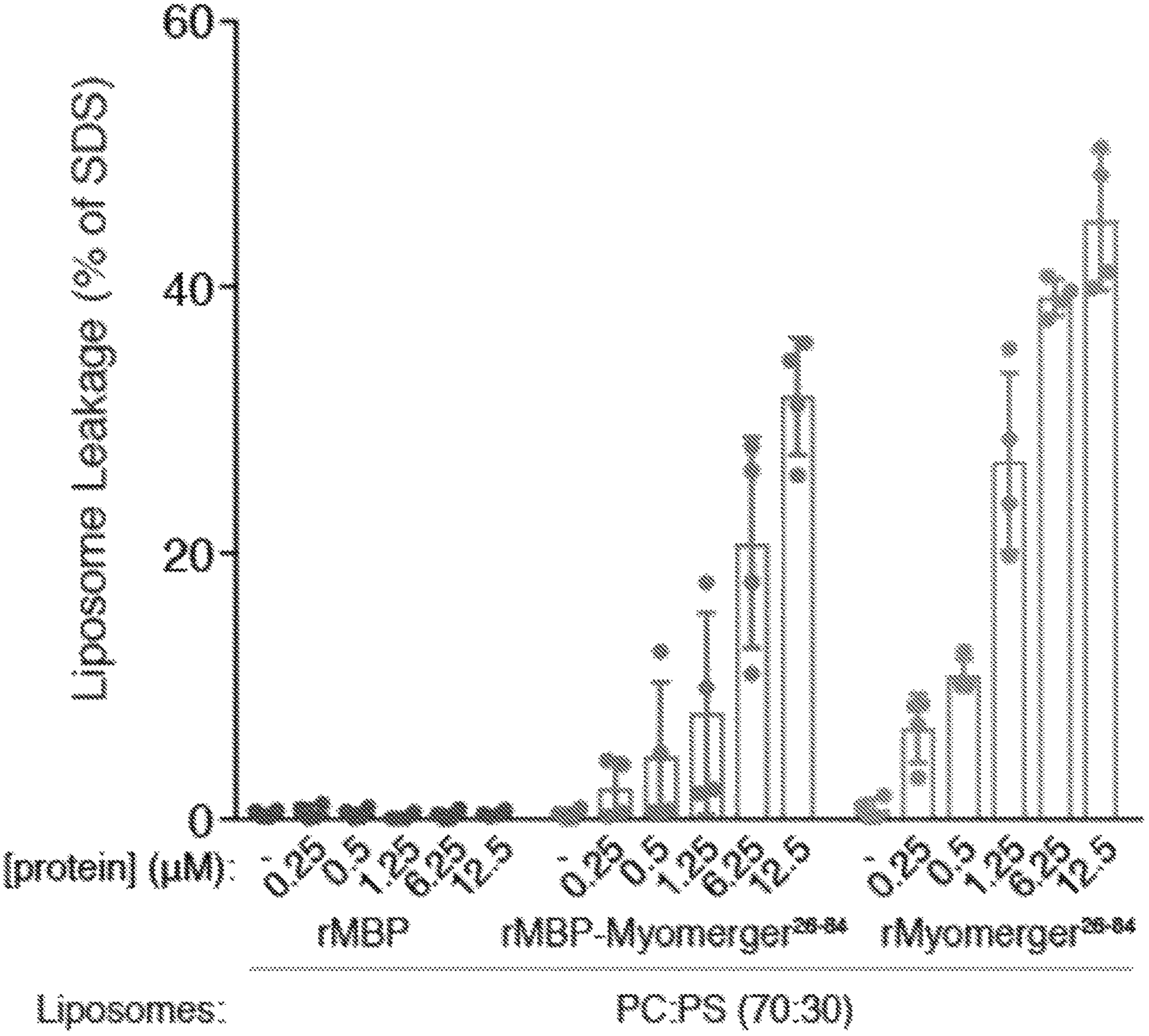
Figure 5:
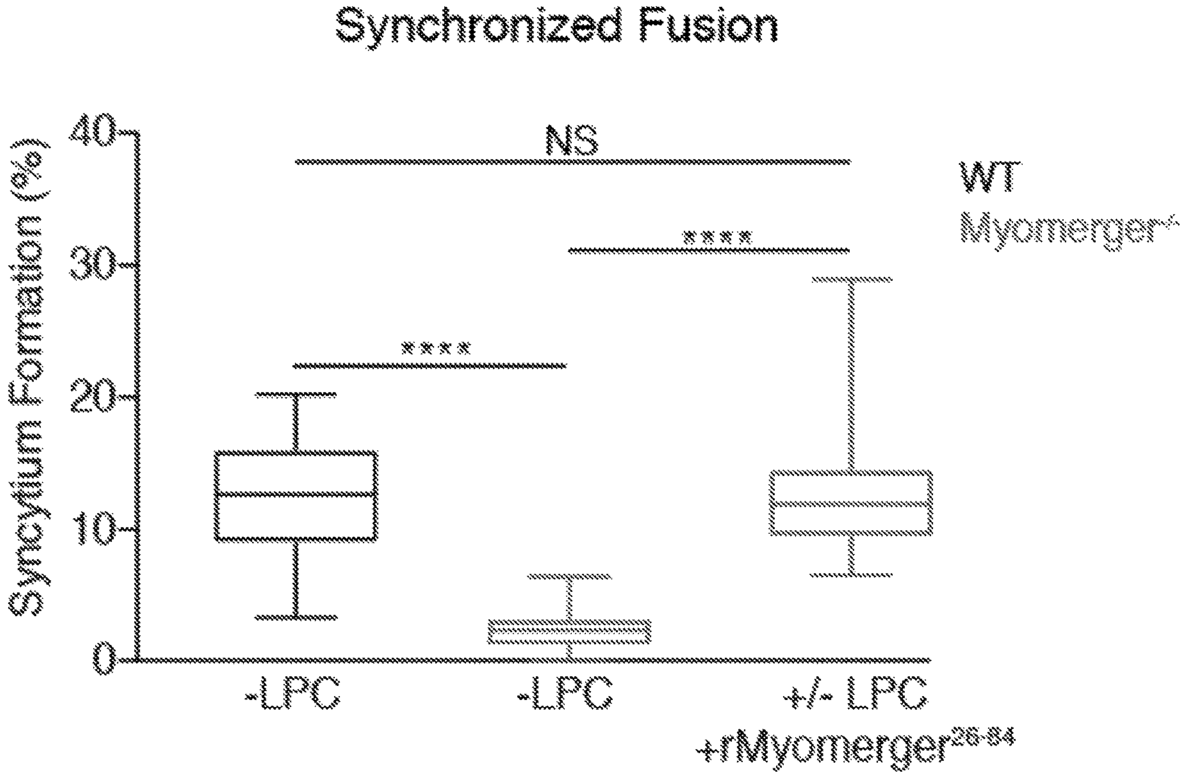
Figure 5:
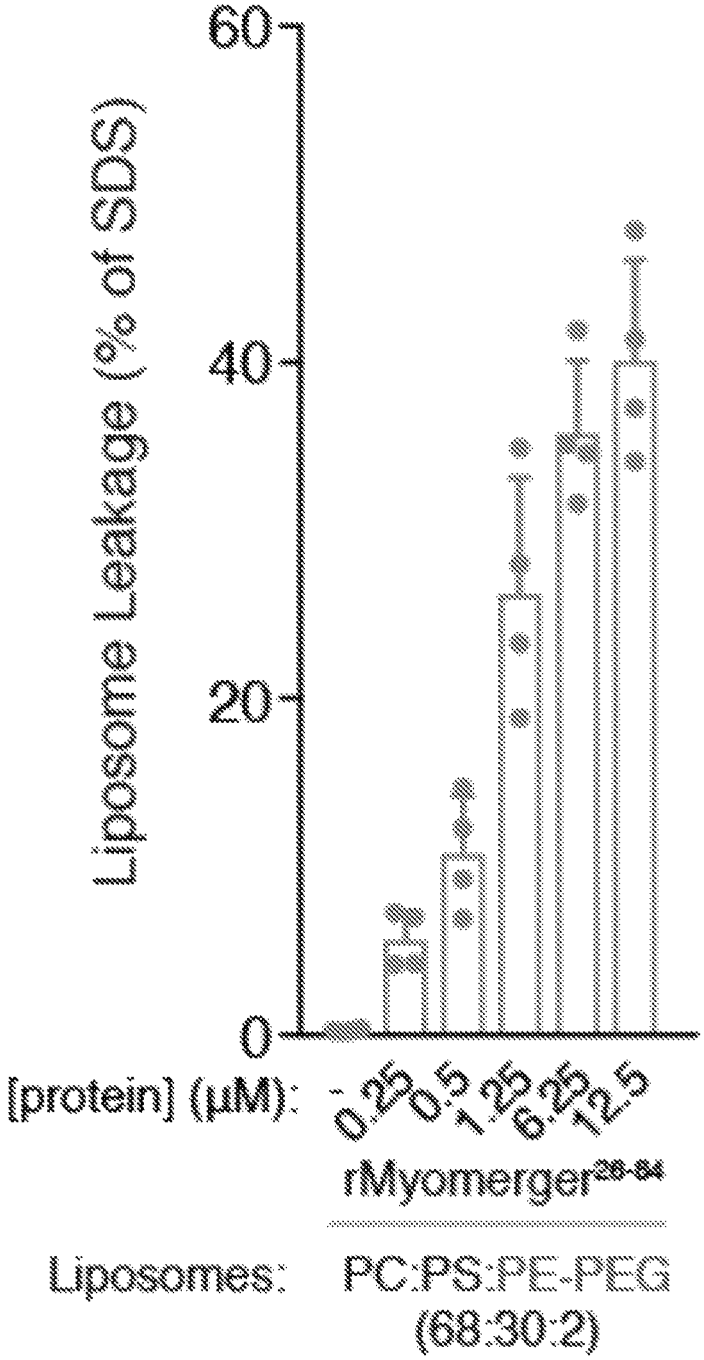
Figure 5:
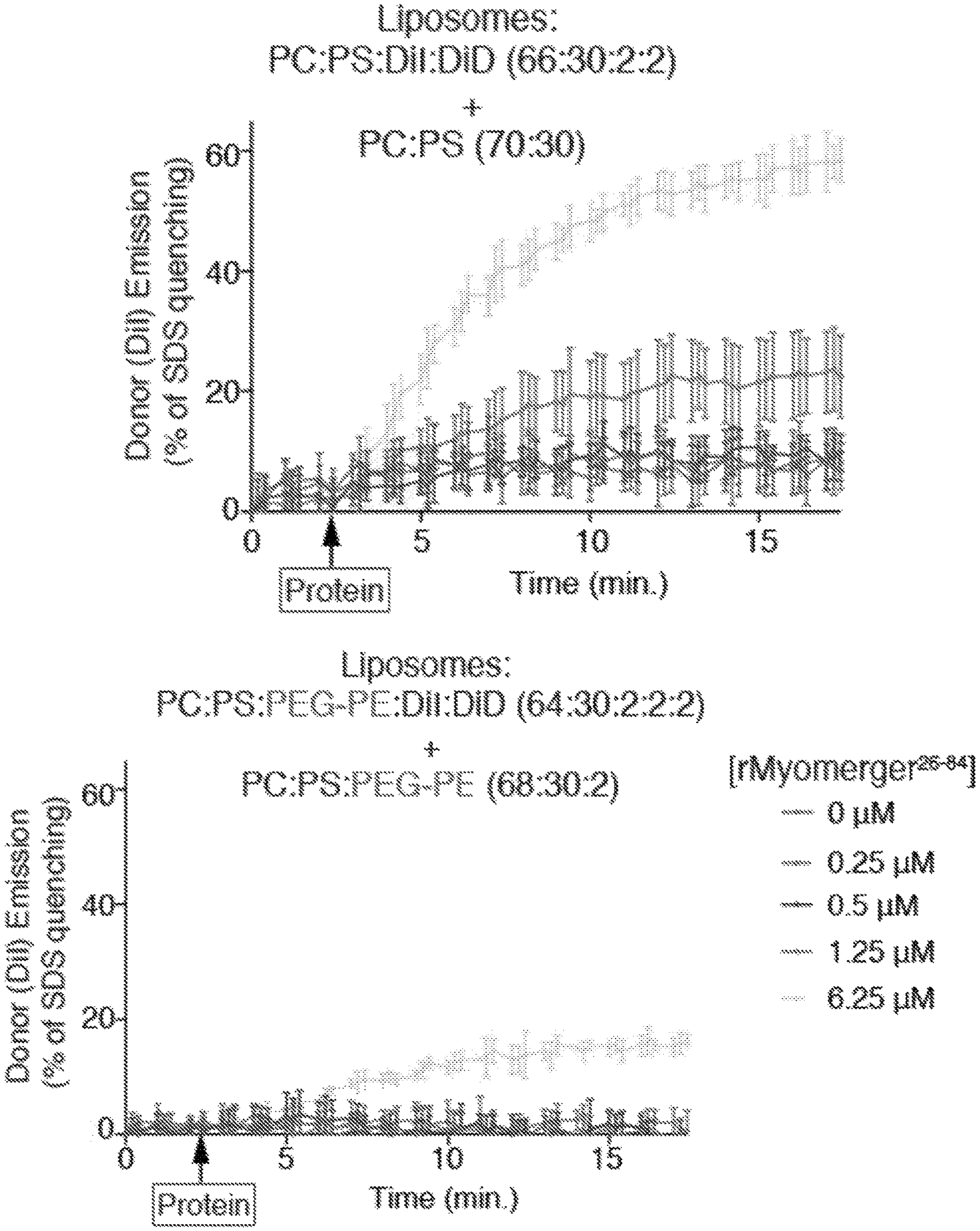
Figure 5:
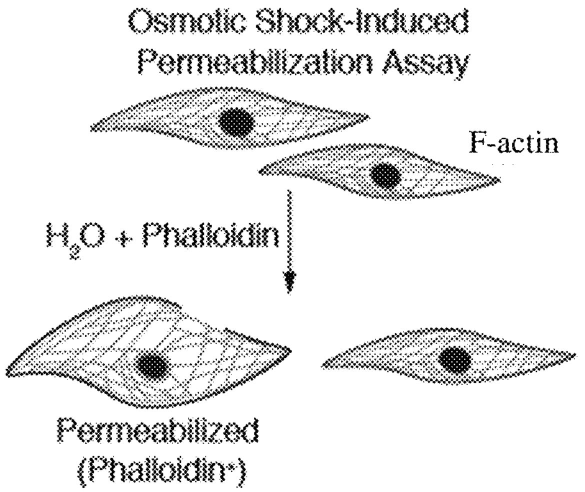
Figure 5:
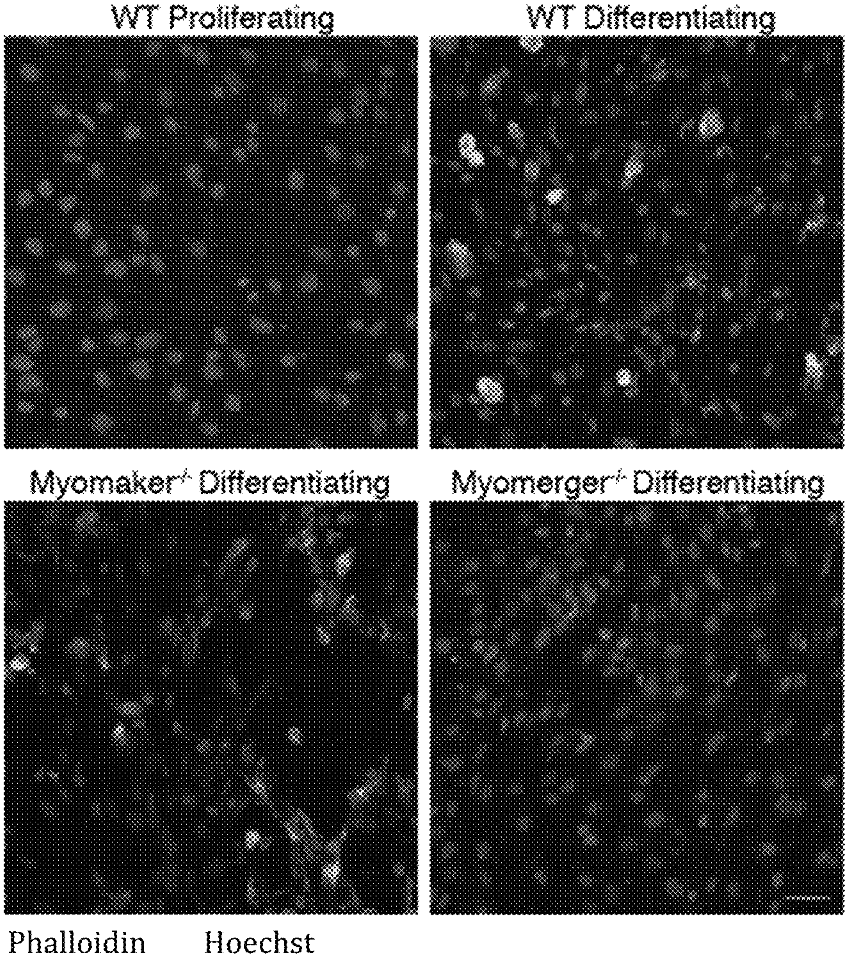
Figure 5:
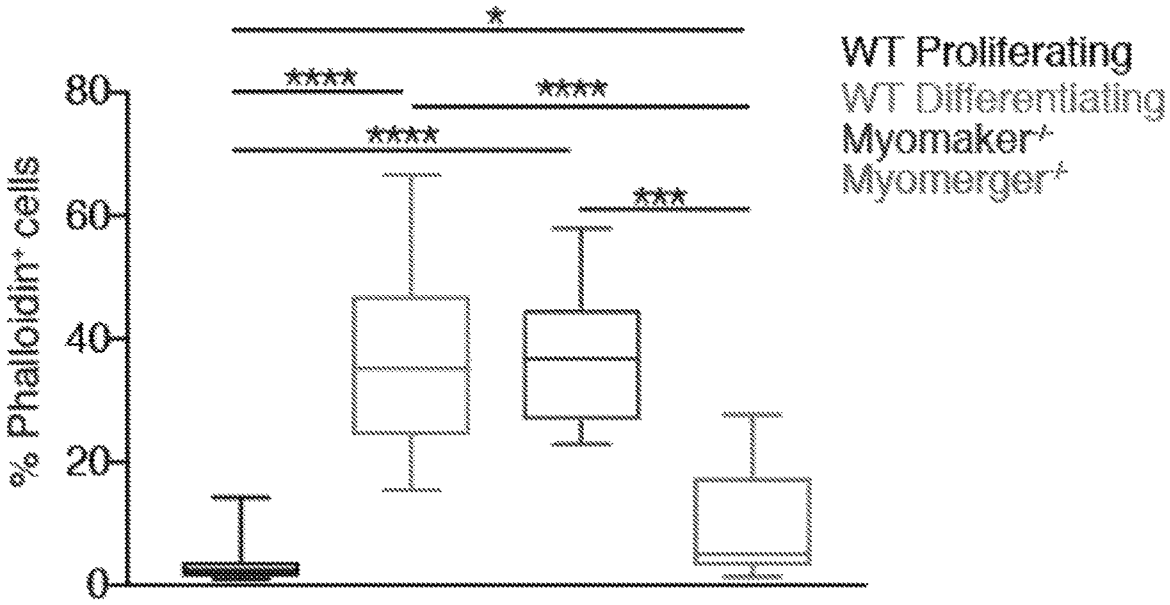

Pleiotropic membrane manipulations that we found to compensate for Myomerger deficiency can generate membrane stresses leading to pore formation. To test if Myomerger function in fusion involves direct effects of the protein on the membrane lipid bilayer, we first tested if Myomerger directly interacts with lipid bilayers and promotes bilayer permeabilization. We incubated recombinant Myomerger ectodomains with protein-free liposomes encapsulated with sulforhodamine B at self-quenching concentrations. Protein-induced leakage of liposome content dilutes the probe and increases its fluorescence (FIG. 5A). Fluorescence was normalized to the fluorescence detected when all liposomes were lysed by application of SDS. Liposome leakage was observed upon addition of rMBP-Myomerger$^{26\text{-}84}$ but not rMBP (FIG. 5B). Quantification of liposome leakage two minutes after the addition of various concentrations of protein confirmed an ability for rMBP-Myomerger$^{26\text{-}84}$ to rearrange membrane lipids (FIG. 5C). To control for the possibility that the MBP epitope tag impacted our analysis, we removed MBP and purified recombinant Myomerger$^{26\text{-}84}$ (FIG. 5D). rMyomerger$^{26\text{-}84}$ induced liposome leakage (FIG. 5E) and rescued synchronized fusion of Myomerger myoblasts (FIG. 5F). These findings indicate that the membrane-destabilizing and fusion-rescuing activities of rMBP-Myomerger$^{26\text{-}84}$ do not depend on the MBP tag.

Proteins and peptides can lyse liposomes through multiple mechanisms including directly promoting pore formation in the liposomal bilayer, by driving liposome-liposome adhesion strong enough to deform and rupture the liposomes, or by inducing liposome fusion that in some cases may be accompanied by a temporal increase in bilayer permeability ("leaky fusion"). To assess if Myomerger induces liposome leakage through an adhesion-dependent mechanism, we included 2 mole % of polyethylene glycol (PEG-PE) 2000 grafted lipid into the liposome composition. While these and even lower amounts of PEGylated lipid suppress liposome aggregation, rMyomerger$^{26\text{-}84}$ effectively permeabilized PEGylated liposomes indicating that it does so through an adhesion-independent mechanism (FIG. 5G). Next, to determine if Myomerger-induced liposome leakage is accompanied by lipid mixing we incubated DiI- and DiD-labeled liposomes with unlabeled liposomes, and then added rMyomerger$^{26\text{-}84}$. In this FRET-based system, where DiI is the donor and DiD is the acceptor, lipid mixing between labeled and unlabeled liposomes would dilute the FRET between DiI and DiD and result in an increase of DiI emission. At the end of each of the FRET experiments, we added detergent to measure DiI emission corresponding to infinite dilution of the probes (100% lipid mixing). While 1.25 μM (1 protein per 40 lipids) and higher concentrations of rMyomerger$^{26\text{-}84}$ induced lipid mixing (FIG. 5H), lower concentrations of the protein that we found to be sufficient to induce leakage (FIG. 5E), did not induce lipid mixing indicating that liposome leakage does not depend on fusion. This conclusion was further substantiated by finding that supplementing liposome composition with PEGylated lipid suppresses lipid mixing but not liposome leakage (FIG. 5H, 5G). The finding that liposome leakage does not depend on either adhesion or fusion of the liposomes indicates a direct lipid-destabilizing activity for the ectodomain helices of Myomerger.

In another approach, to explore whether Myomerger expression alters cell membrane properties that are helpful for pore formation, we focused on the ability of myoblasts to withstand hypotonic osmotic shock. Exposure to distilled water increases osmotic pressure across the plasma membrane, removes excess surface area and generates tension in the plasma membrane. When the critical membrane tension is reached, it generates pore(s) resulting in a membrane that is now permeable to normally impermeable molecules. The higher propensity for the membrane lipid bilayer to form a pore, the lower the critical tension required for permeabilization of plasma membrane of the cells subjected to the osmotic shock. We examined the effects of Myomaker and Myomerger expression on the osmotic shock-induced permeabilization of C2C12 cells. The cells were incubated in water for 30 seconds in the presence of a fluorescent F-actin probe (phalloidin) that does not enter intact cells. Cells with the pores were identified as being phalloidin$^+$ (FIG. 5I). Correlation of Myomerger expression with elevated sensitivity to osmotic shock was illuminated by the finding that proliferating WT C2C12 myoblasts that do not express Myomerger were less sensitive to osmotic shock (i.e. a lower percentage of the cells became phalloidin$^+$ after application of hypotonic osmotic shock) compared to differentiating WT C2C12 cells (FIG. 5J). Moreover, we observed that differentiating Myomerger$^{-/-}$ myoblasts were less sensitive to osmotic shock than WT and Myomaker$^{-/-}$ myoblasts, as evidenced by a lower percentage of permeabilized Myomerger$^{-/-}$ cells (FIG. 5J and FIG. 5K). Each of these findings are consistent with the idea that Myomerger facilitates pore formation in the lipid bilayer of the plasma membranes of differentiating myoblasts.

Myomerger Appears to Drive Fusion Completion Independent of Myomaker

Figure 3:
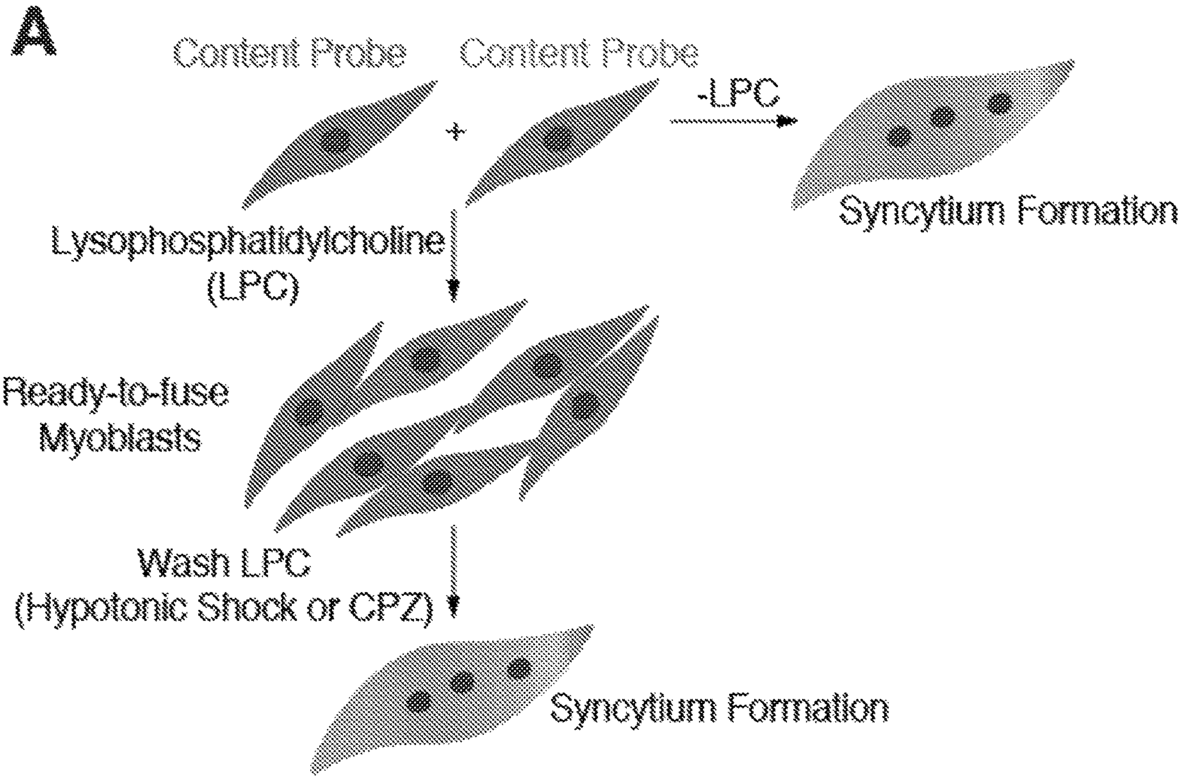
FIG. 3: Myomaker does not appear to require Myomerger to efficiently initiate hemifusion structures. (A) Myoblasts were labeled with content probes (either orange cell tracker or green cell tracker) and differentiated for 48 hours. One set of myoblasts was allowed to fuse uninterrupted without ITC (Control (-LPC)), while others were treated with the synchronization agent LPC for 16 hours in differentiation medium to accumulate myoblasts that are ready-to-fuse. At the time of LPC removal, which allows cells to undergo hemifusion and complete fusion, the cells ware exposed to either hypotonic shock (1:3 PBS:$H_2O$) or chlorpromazine (CPZ) for 60 seconds, washed and assayed for fusion after 30 minutes. (B) Representative images show fusion for myoblasts that were not exposed to LPC (Control (-LPC)) and myoblasts that were synchronized with LPC and then treated with CPZ. (C) Quantification of syncytium formation as the percentage of nuclei n multinucleated cells (defined as cells with 2 or more nuclei). Statistical analyses and data presentation: (C) Mann-Whitney test; box-and-whisker plots show median (center line), 25th-75th percentiles (box) and minimum and maximum values (whiskers); NS not significant, $^{*}P<0.05$, $^{*}P<0.001$, $^{**}P<0.0001$; Scale bar, 50 μm.
Figure 3:
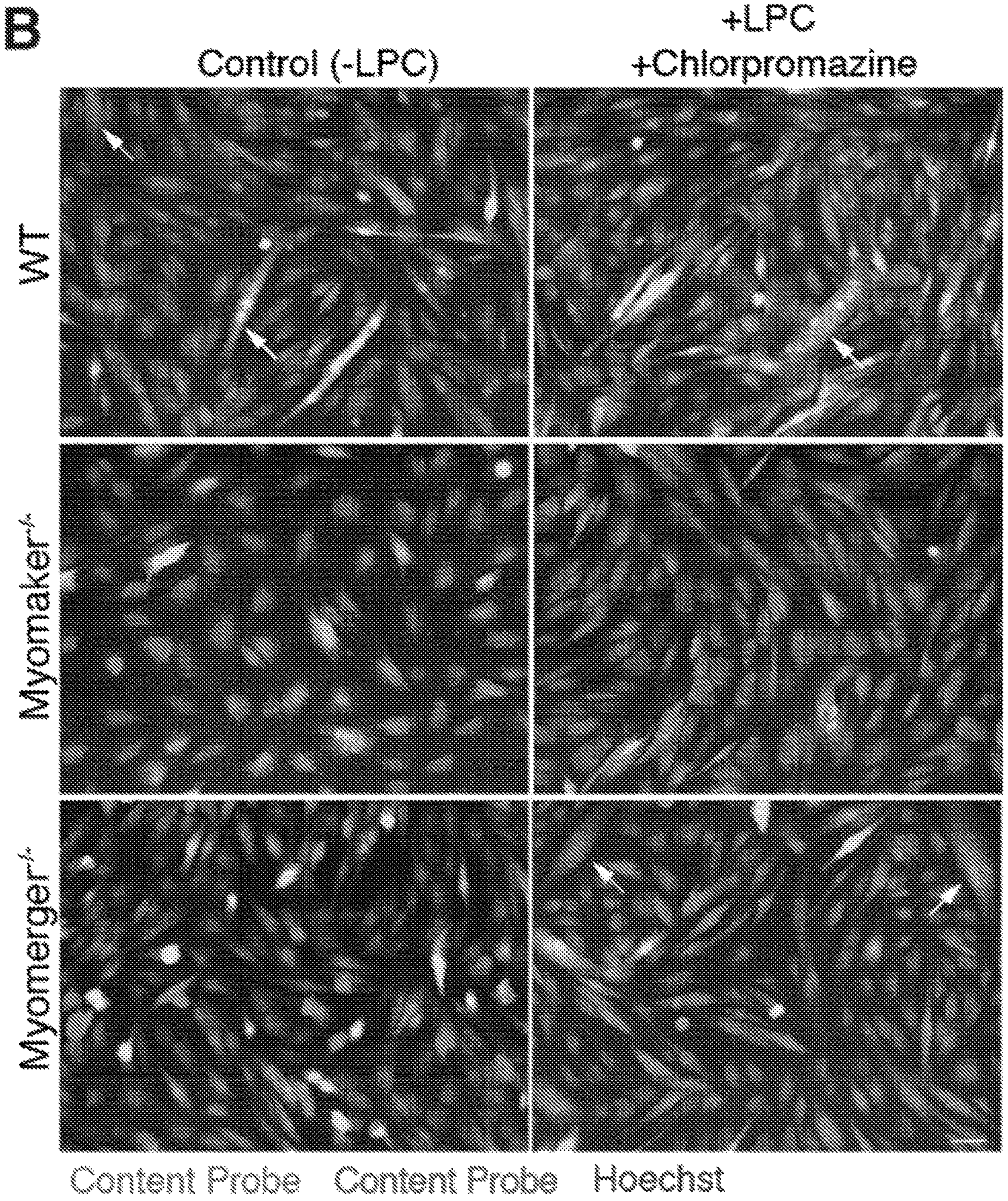
Figure 3:
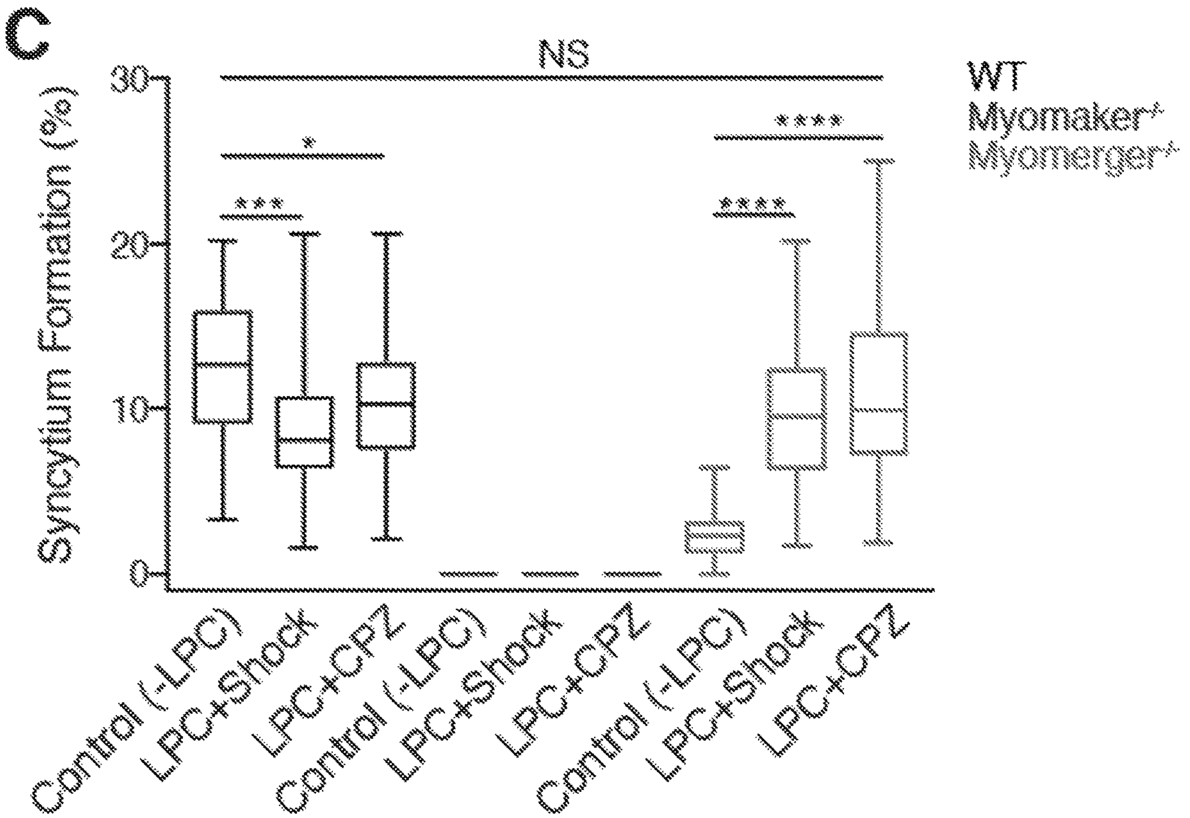

Our data thus far indicate that Myomaker and Myomerger appear to govern distinct aspects of the fusion reaction and suggest a step-wise fusion reaction in myoblasts, where different proteins perform independent functions that culminate in membrane coalescence. Further support for this model is that Myomaker can establish hemifusion connections in the absence of Myomerger (FIG. 3). If the reaction proceeds through a step-wise mechanism with independent functions one could predict that a physical interaction between Myomaker and Myomerger may not be not obligatory for function. Thus, we next sought to determine if Myomerger possesses an activity independent of Myomaker and probed the requirement for a physical interaction.

Figure 6:
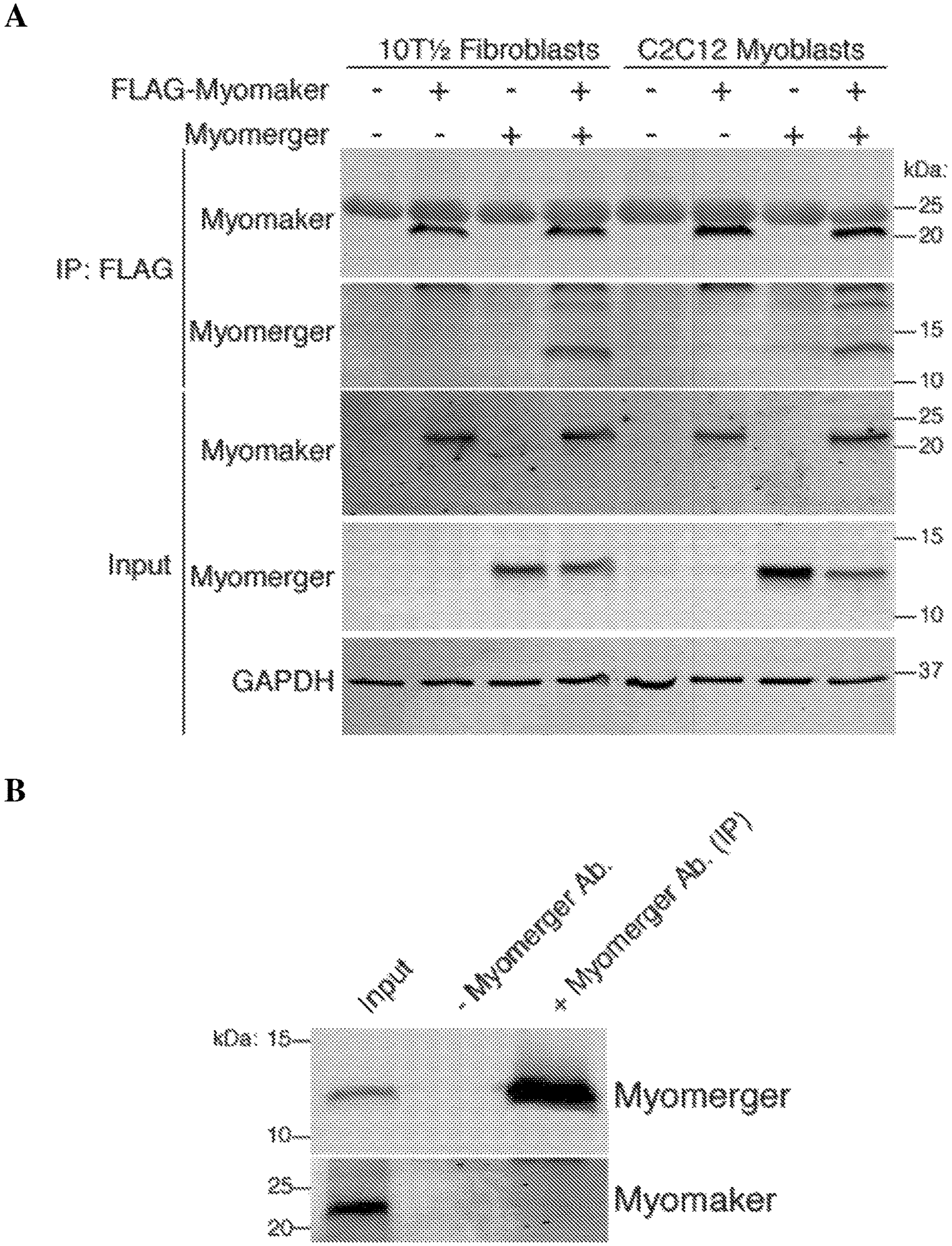
FIG. 6: Myomerger appears to drive fusion completion independent of Myomaker. (K) Schematic showing heterologous fusion assay. 3T3 fibroblasts expressing hemagglutinin (HA) were transfected with empty, Myomaker or Myomerger plasmids and mixed with erythrocytes that were labeled with both lipid and content probes. (M) At selected sub-optimal conditions, HA only drives hemifusion (fibroblasts labeled with the lipid probe, arrowhead). Since fibroblasts are much larger than erythrocytes, hemifusion events are seen as appearance of large cells labeled with only lipid probe. Expression of Myomerger but not Myomaker appears to drive complete fusion (fibroblasts labeled with both lipid and content probes, arrows). (N) Quantification of hemifusion (left) and complete fusion (right) from (M) (n=3 independent experiments). Statistical analyses and data presentation: Mann-Whitney test; box-and-whisker plots show median (center line), 25th-75th percentiles (box) and minimum and maximum values (whiskers); *P<0.05, *P<0.001, **P<0.0001. NS, not significant. Scale bar, 50 μm. See also (A)-(J) and (L).
Figure 6:
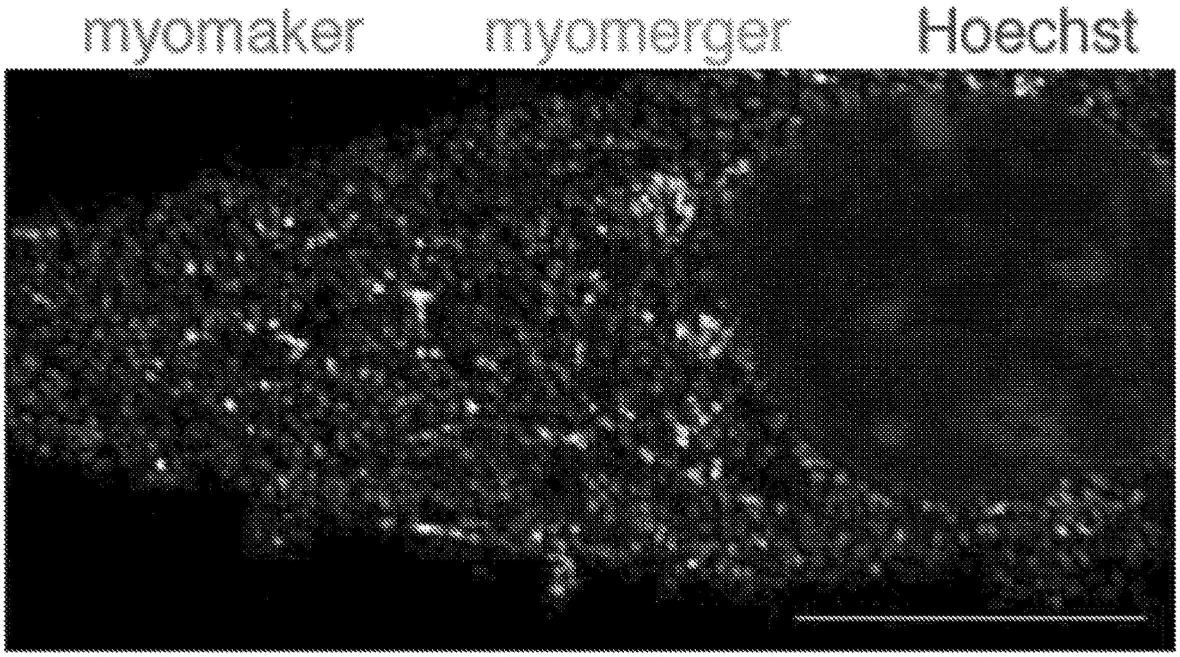
Figure 6:
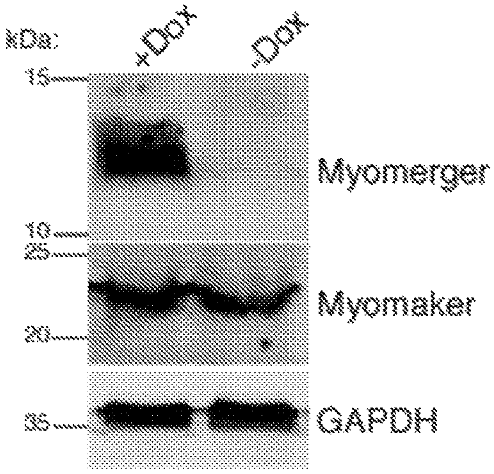
Figure 6:
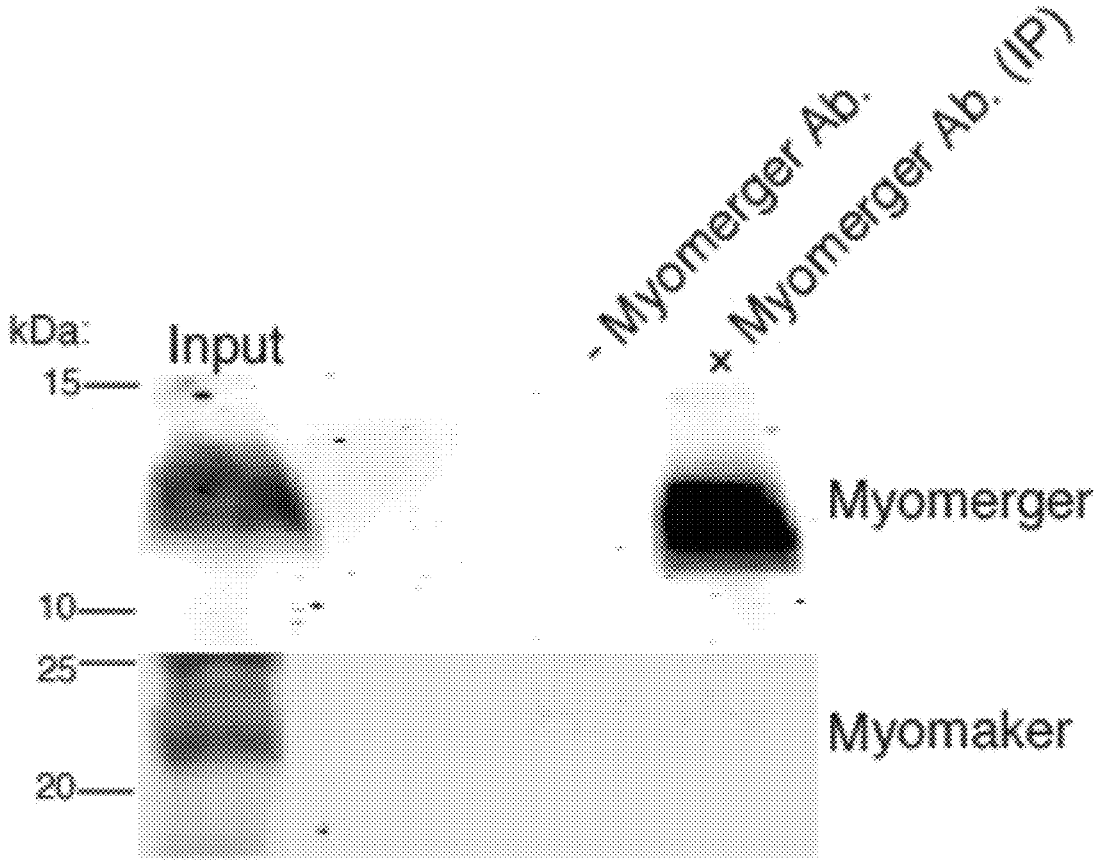
Figure 6:
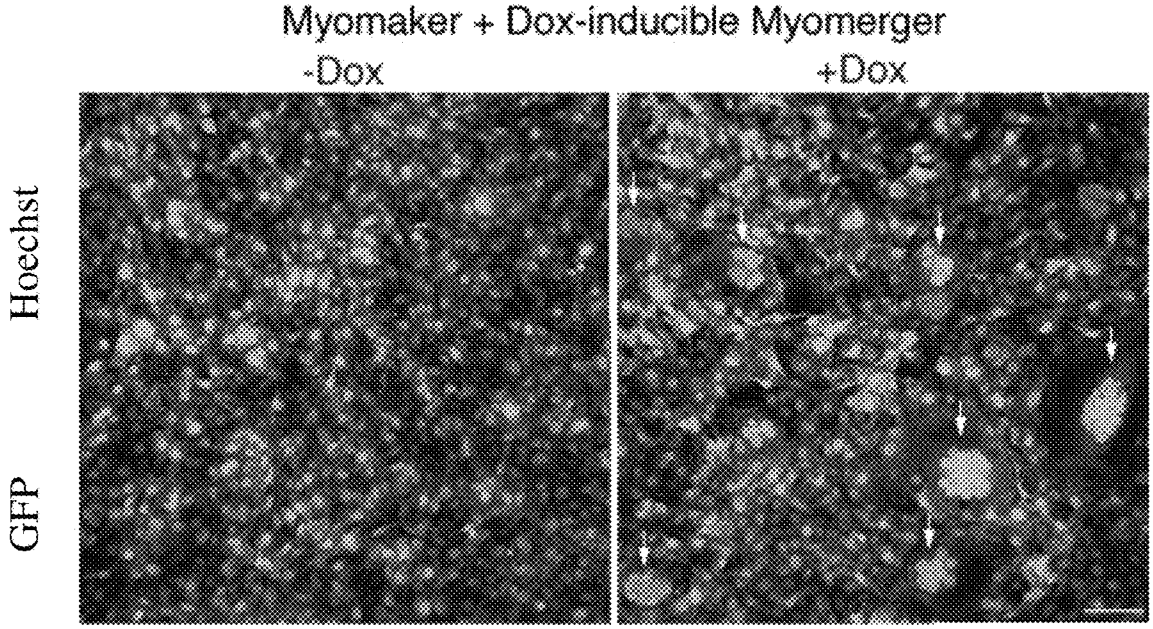
Figure 6:
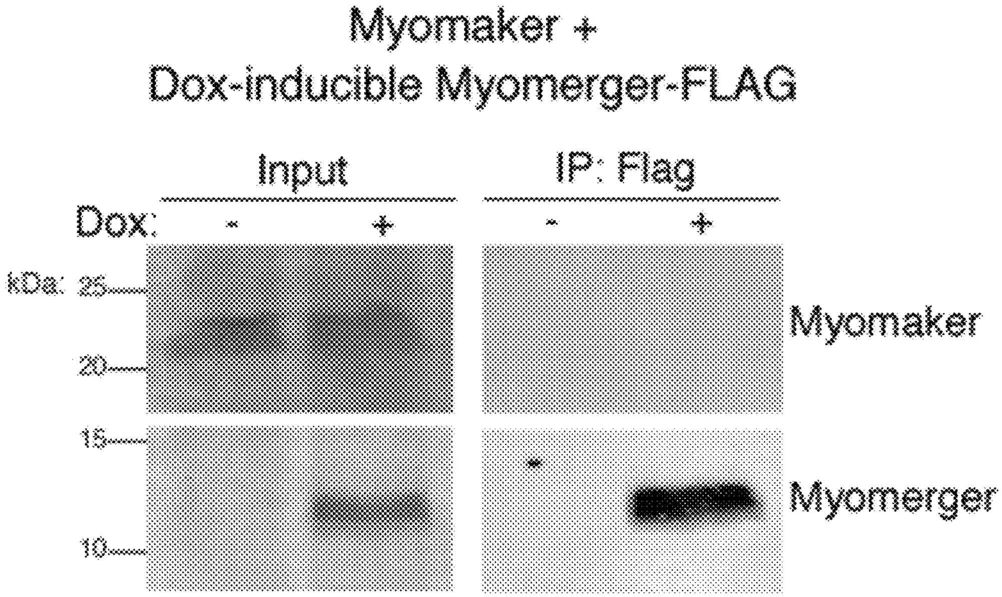
Figure 6:
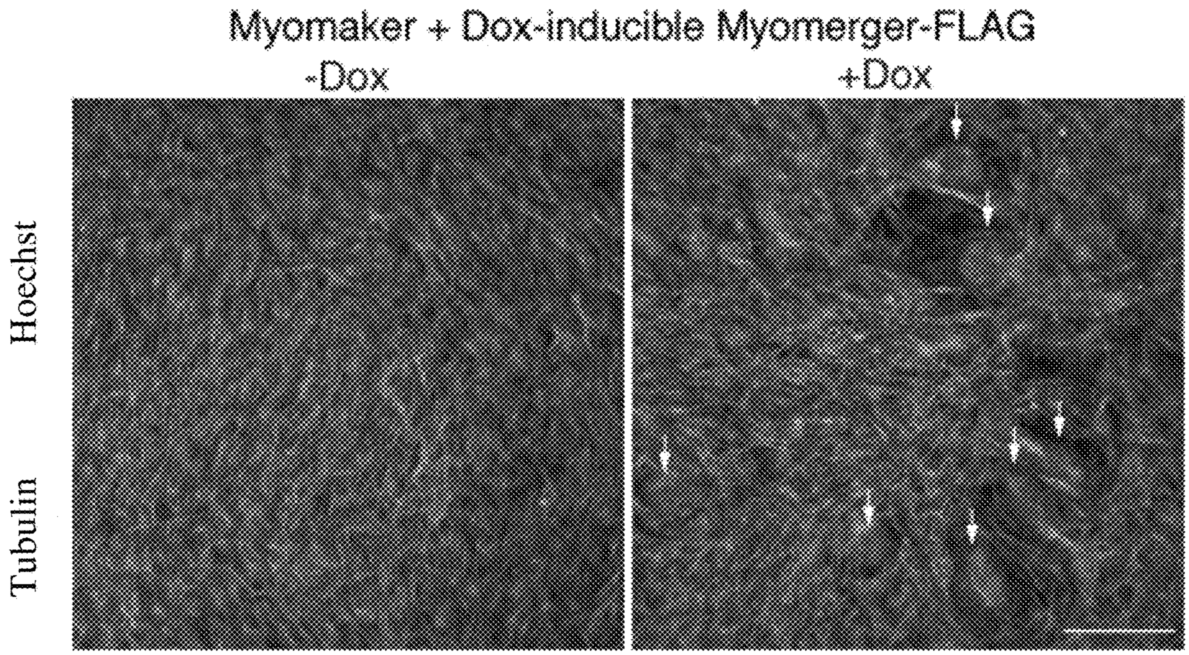
Figure 6:
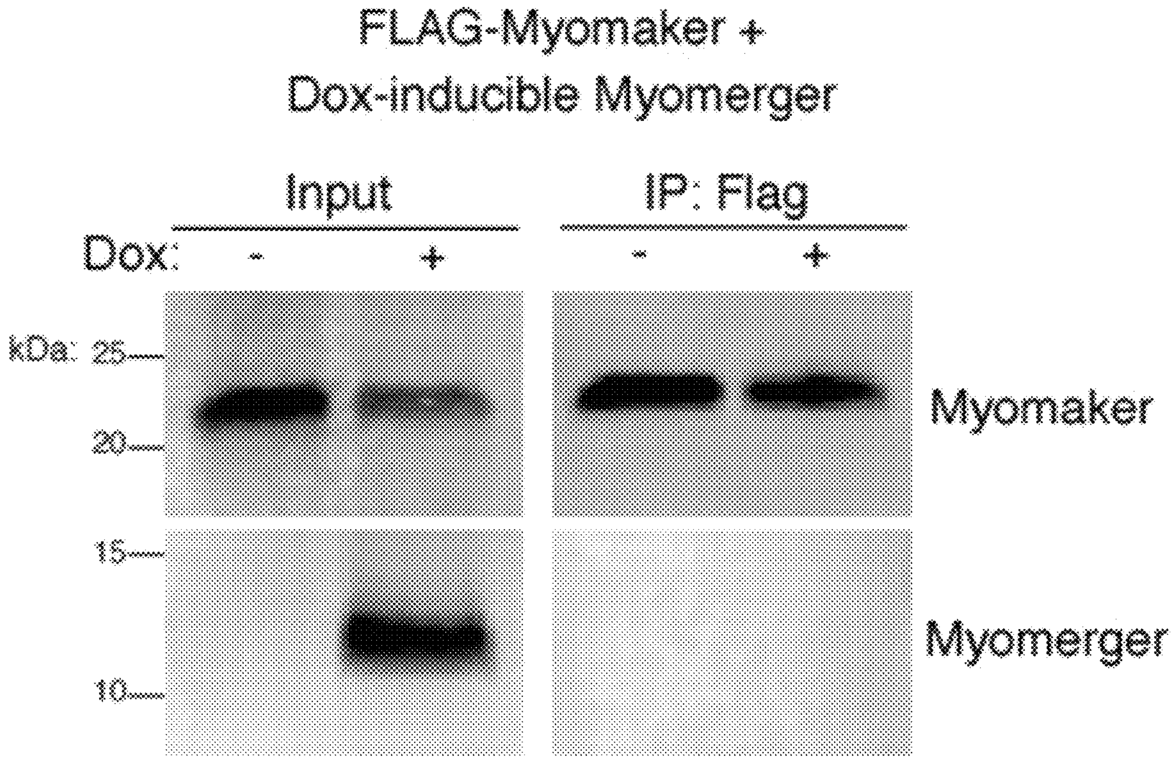
Figure 6:
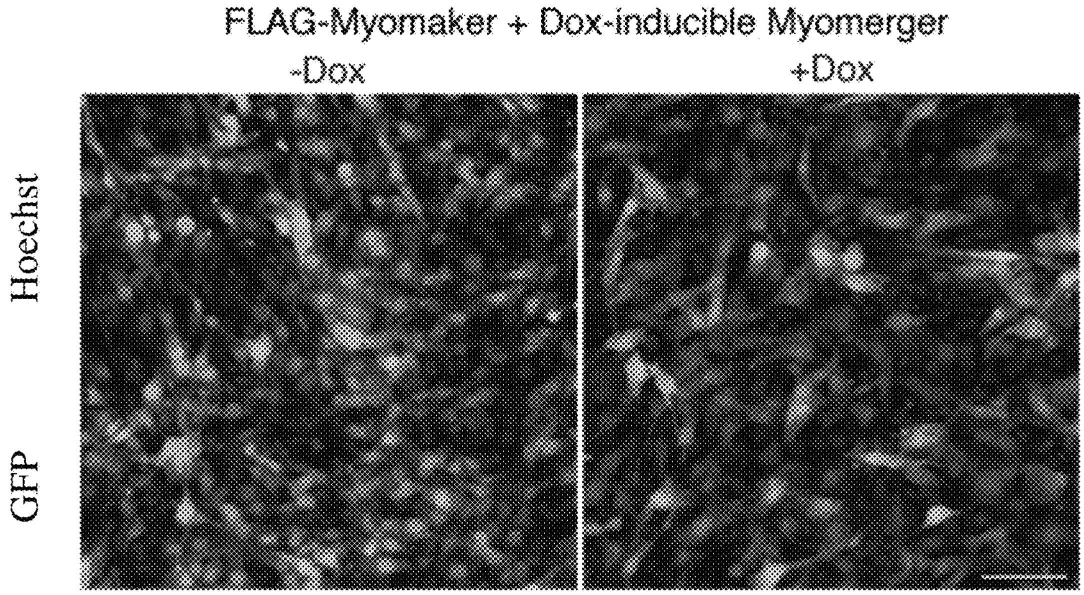
Figure 6:
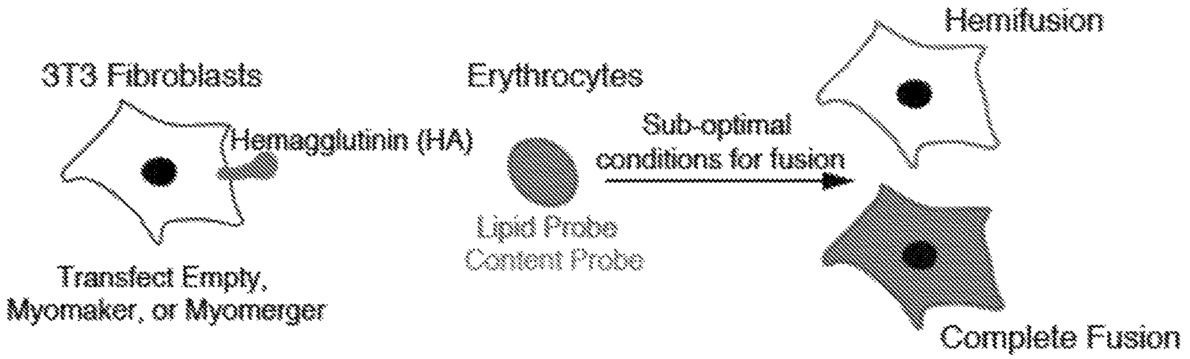
Figure 6:
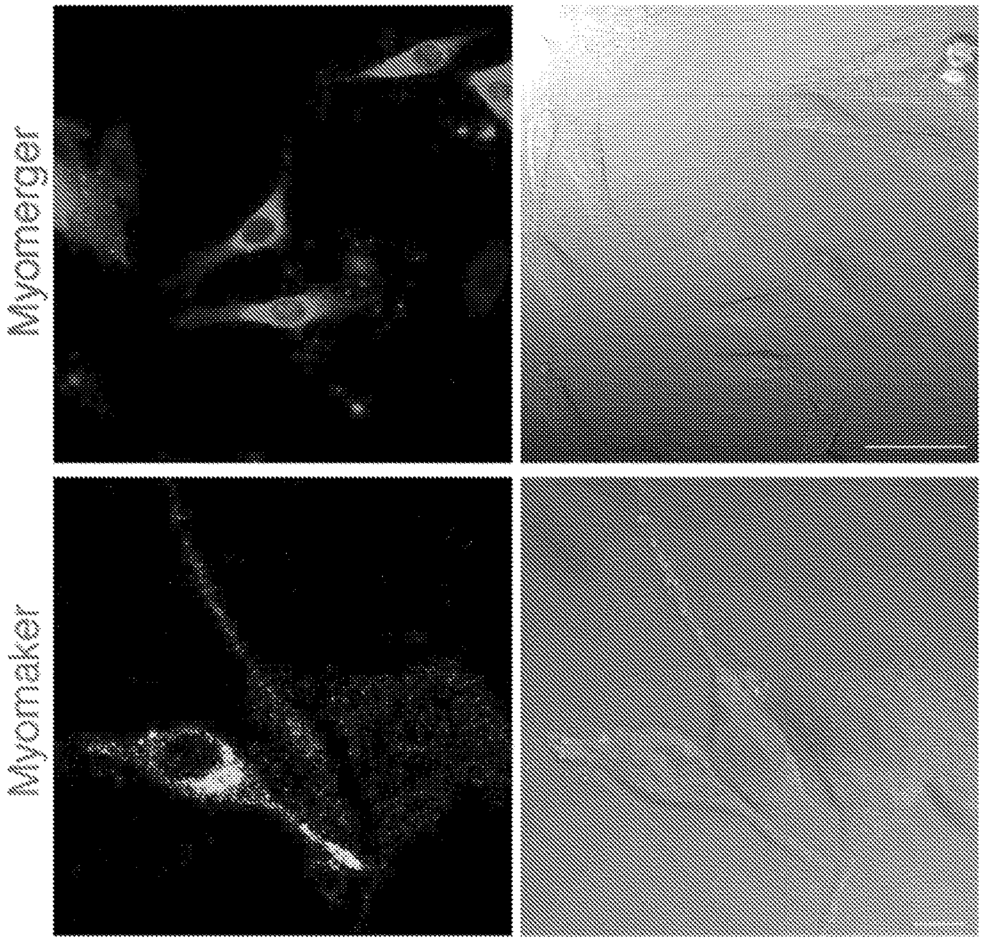
Figure 6:
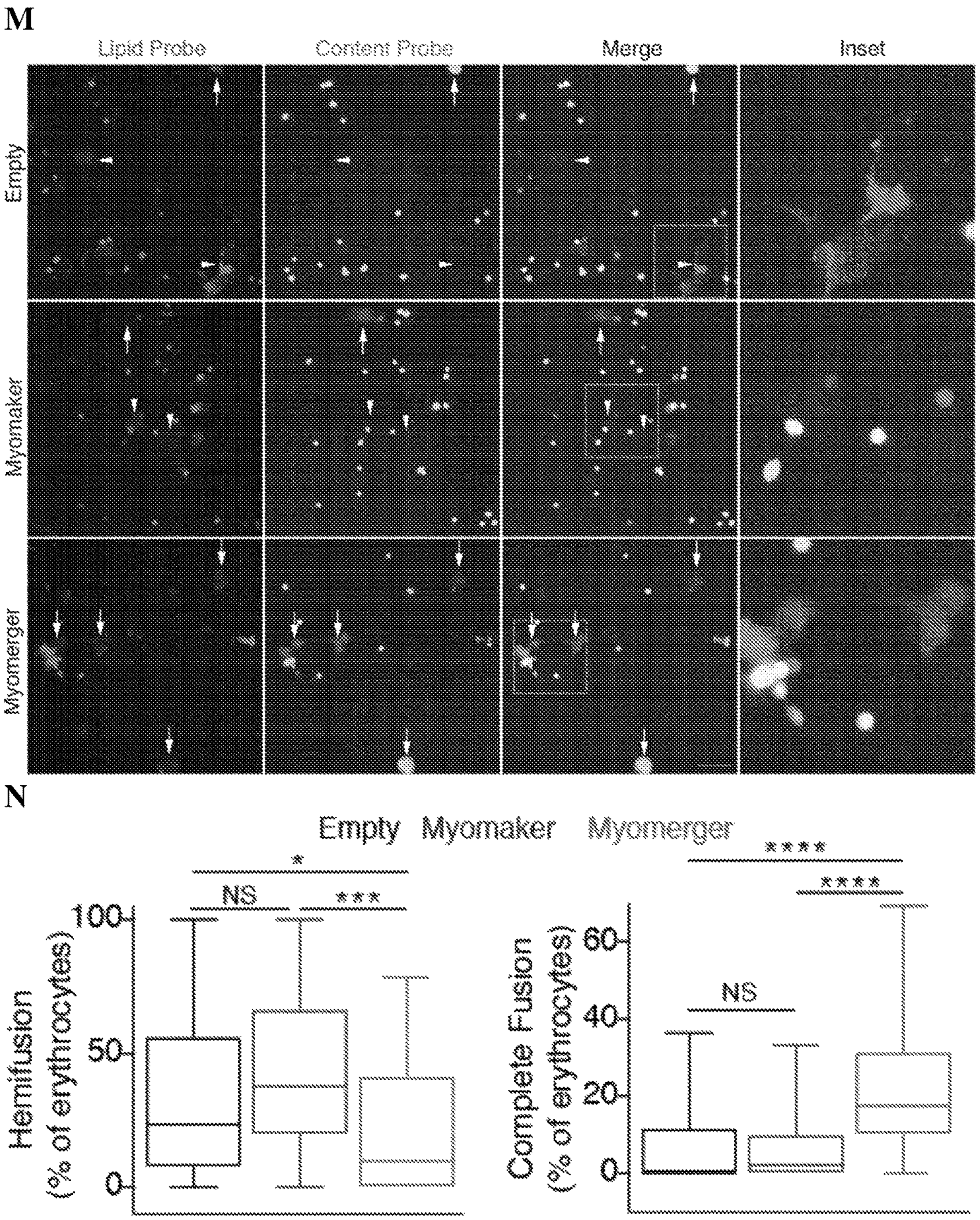

A physical interaction was previously demonstrated between FLAG-Myomaker and Myomerger through co-immunoprecipitations (co-IP) after acute retroviral infection, leading to the idea that an interaction could be relevant for function. While we have confirmed a physical interaction between FLAG-Myomaker and Myomerger in the acute retroviral system (FIG. 6A), we have not detected co-localization in intracellular compartments in differentiated myoblasts using standard confocal microscopy. We also did not detect a physical interaction in C2C12 myoblasts overexpressing untagged Myomaker with endogenous levels of Myomerger (FIG. 6B), and found no co-localization of these proteins through super-resolution microscopy (FIG. 6C). Thus, whether Myomaker and Myomerger directly interact and work as a complex remains an open question.

One possible complication with the detected physical interaction is that it is achieved through retroviral infection, which involves the presence of a viral fusogen that could impact the reconstitution assay. We thus established an inducible fusion reconstitution system that does not rely on acute retroviral infection. 10T½ fibroblasts were transduced sequentially with a Myomaker retrovirus and a lentivirus containing a Dox-inducible Myomerger construct, then selected with puromycin over multiple passages. Myomaker was expressed in −Dox and +Dox samples but Myomerger expression was only detected after the addition of Dox (FIG. 6D). A Myomaker-Myomerger interaction by co-IP was not detected using the same detergent conditions as in the retroviral system, however fusion was reconstituted (FIG. 6E and FIG. 6F). We also generated two additional cell lines with FLAG-tagged proteins. No physical interaction was detected in Myomaker$^+$ fibroblasts with Dox-inducible Myomerger-FLAG despite an induction of fusion (FIG. 6G and FIG. 6H). FLAG-Myomaker$^+$ fibroblasts with Dox-inducible Myomerger also did not yield a physical interaction and fusion was not reconstituted (FIG. 6I and FIG. 6J). This suggests that FLAG-Myomaker does not fully recapitulate untagged Myomaker function, which raises the possibility that the interaction detected in acute retroviral systems may not be functionally relevant. Our data indicate that Myomaker and Myomerger collaboration in fusion does not appear to require a physical interaction between these proteins.

The absence of detectable Myomaker-Myomerger complexes supports our hypothesis that these proteins have independent and distinct functions. While Myomaker and Myomerger may form transient interactions that are difficult to capture, another question is whether Myomerger drives fusion completion in the absence of Myomaker. We used a heterologous fusion assay between 3T3 fibroblasts, expressing the viral fusogen hemagglutinin (HA), and erythrocytes (red blood cells, RBCs) containing both lipid and content probes (FIG. 6K). We transfected HA-expressing fibroblasts with either empty vector, Myomaker, or Myomerger, and mixed the cells with labeled RBCs.

We confirmed expression of Myomaker and Myomerger in fibroblasts through immunostaining (FIG. 6L). HA binding to sialic acid receptors at the surface of RBCs brings the membranes of HA$^+$ fibroblasts and RBCs into tight contact (LEIKINA et al (2004) "Influenza hemagglutinins outside of the contact zone are necessary for fusion pore expansion" J Biol Chem, Vol. 279, pp. 26526-26532). To acquire fusion-competence, HA has to be first cleaved by trypsin and then activated by acidic pH. Lowering the number of fusion-competent HAs in HA$^+$ fibroblasts by using reduced trypsin concentrations and suboptimal pH decreases fusion extents, and shifts the observed fusion phenotype from full fusion (lipid- and content-mixing) to mostly hemifusion (lipid mixing without content mixing) (FIG. 6K). Under these conditions, more hemifusion events (since fibroblasts are larger than RBCs, hemifusion events are seen as appearance of large cells labeled with only lipid probe) compared to fully fused cells (fibroblasts with content probe) were observed in empty and Myomaker$^+$ HA$^+$ fibroblasts (FIG. 6M). In contrast, complete fusion events were readily observed in Myomerger-expressing HA$^+$ fibroblasts (FIG. 6M). Quantification of hemifusion and complete fusion as a percentage of RBCs that transferred to fibroblasts only lipid probe (hemifusion) or both lipid and content probe (complete fusion) shows an increase in complete fusion when $HA^+$ fibroblasts are expressing Myomerger (FIG. 6N). This finding appears to demonstrate that Myomerger drives fusion pore formation and fusion completion in a Myomaker-independent manner.

Discussion

Figure 7:
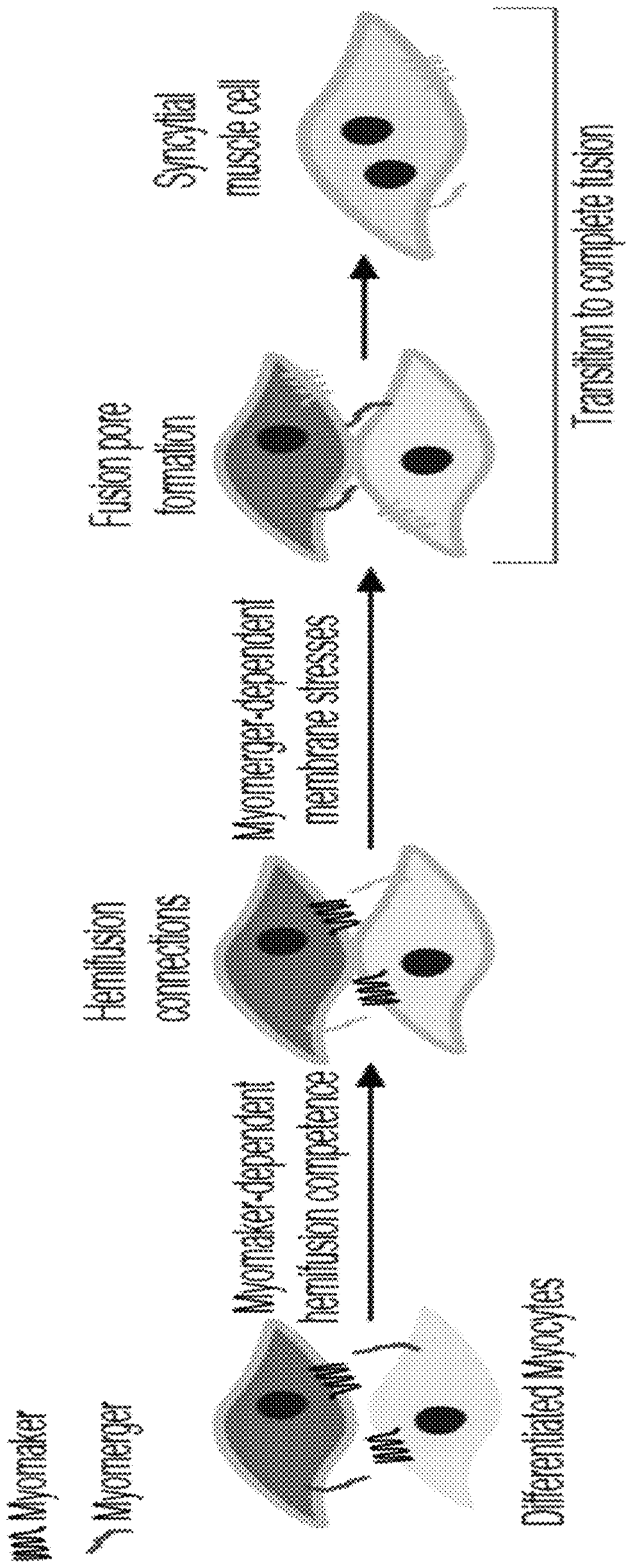
FIG. 7: Schematic of the division of fusogenic labor between Myomaker and Myomerger. Myomaker and Myomerger independently control two distinct stages of fusion in myoblasts. Both proteins are likely expressed simultaneously in differentiated fusion-committed myocytes. Colored proteins are shown during the stage at which they are essential although they may also be active during other times. At the first stage, Myomaker appears to control development of hemifusion competence and appears to be indispensable for hemifusion connections (mixing of lipids (blue)), and Myomerger does not appear to be required for this step. The fusion reaction would stall at this stage without the presence of Myomerger, which at the second stage of the reaction generates membrane-stresses to drive the transition to complete fusion (green-yellow content mixing) in a Myomaker-independent manner. Note that the schematic is meant solely to illustrate how the independent activities of Myomaker and Myomerger cooperate during myoblast fusion, and the other factors that also impact the process are omitted for clarity.

Myoblast fusion is fundamental for proper muscle development and regeneration, and dysregulation of the process leads to myopathies. Here, we further the understanding of myoblast fusion by demonstrating that this fusion reaction appears to proceed through a novel stepwise mechanism where different proteins function at independent points in the pathway. Although not wishing to be bound by theory, we propose a model in FIG. 7 where Myomaker function is helpful for fusion initiation and formation of hemifusion intermediates, and Myomerger appears to drive subsequent fusion pore formation and expansion by generating membrane stresses. In more well-characterized fusion systems (viral and intracellular membrane fusion), reactions can be stalled at the hemifusion stage, but both hemifusion and pore formation are driven by the same protein complex. Thus, we have revealed a membrane fusion mechanism that appears to be divergent from well-established models of fusion such as SNARE-mediated intracellular fusion, HA-mediated viral fusion, and Eff-1 developmental fusion.

The discovery of two factors for myoblast fusion has led to questions about how they may work together to drive the process. Our data indicate that Myomaker does not appear to need Myomerger to mediate hemifusion. Indeed, the treatments promoting hemifusion-to-fusion transition of Myomerger$^{-/-}$ myoblasts result in levels of complete fusion comparable to WT levels, showing that the lack of Myomerger does not compromise Myomaker-dependent hemifusion. Similarly, we also establish that Myomerger does not appear to have an obligate requirement for Myomaker to complete the fusion reaction. Myomerger can drive completion of heterologous fusion reactions mediated by the viral fusion protein HA, a system apparently devoid of Myomaker. Furthermore, we utilized extensive co-IP analysis and super-resolution microscopy to demonstrate a lack of physical interaction, or obvious co-localization, between Myomaker and Myomerger. We only detect a physical interaction with epitope-tagged versions of Myomaker after retroviral infection. While our analysis does not preclude the possibility that Myomaker and Myomerger interact in discrete domains on the plasma membrane, or an interaction could be detected with certain detergents or improved antibodies, our results suggest that physical interactions between these proteins are likely irrelevant for their function in myoblast fusion.

Our data indicate that myoblast fusion stalls at hemifusion in the absence of Myomerger. Indeed, cell-to-cell redistribution of lipid probe in the absence of redistribution of content probe is a defining hallmark of hemifusion. The conclusion that Myomerger-deficient cells form hemifusion connections was further supported by two independent experimental approaches that do not utilize lipid mixing assay. We found that fusion intermediates formed by Myomerger-deficient cells could be effectively transformed into full fusion by mild hypotonic shock and CPZ applications, two treatments used in studies on viral fusion to reveal hemifusion structures by their transformation into full fusion. Since neither of the three hemifusion-revealing approaches we used (lipid mixing assay, hypotonic shock and CPZ applications), detected hemifusion for Myomaker-deficient cells, we conclude that Myomaker functions at the hemifusion stage or prior to it. Myomaker might directly control hemifusion, possibly by acting in trans on both fusing cells to bring membranes in close enough proximity to mix lipids, or indirectly through cooperation with additional cellular machinery. The stalling of fusion at the hemifusion stage in Myomerger$^{-/-}$ myoblasts provides the first evidence of a 'divided' fusion reaction. Since other developmental cell-cell fusion processes apparently also proceed through hemifusion intermediates, some or all of these processes may utilize a similar division of functions between fusogenic proteins providing a regulatory checkpoint to ensure fidelity of the fusion reaction.

Myomerger possesses membrane stressing activities potentially through its helical regions in the ectodomain. The first helical region in the ectodomain has an amphipathic character and is 12 amino acids, whereas the second helix is hydrophobic and contains 15 amino acids. Our surface biotinylation experiments in which we found lysines in the C-terminal region of Myomerger (the only lysines in the protein) to be biotinylated by a membrane impermeable reagent suggest extracellular localization of the non-transmembrane region of Myomerger. Furthermore, antibodies to the Myomerger ectodomain inhibit synchronized fusion showing functional relevance of Myomerger ectodomain located at the surface of myoblasts. However, we can not exclude a scenario in which Myomerger influences actin dynamics acting from outside the cell.

As reported above, Myomerger renders membranes susceptible to permeabilization, and reagents found to compensate for Myomerger deficiency are also known to promote membrane permeabilization. Given that Myomerger facilitates opening of pores in a membrane bilayer and thus likely generates convex (positive) curvature of the lipid monolayer, it is possible that this positive curvature effect of Myomerger at the negatively-curved rim of the hemifusion structure generates additional elastic stresses that nucleates fusion pore formation.

Example Set B

Figure 8:
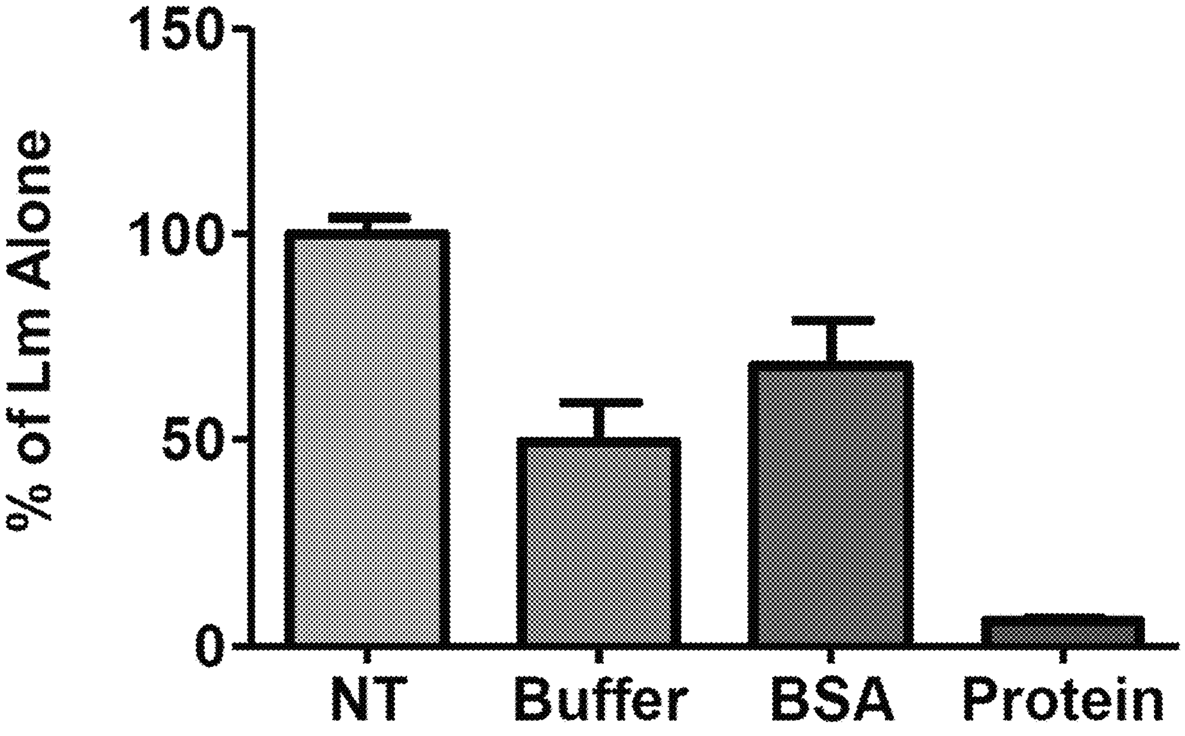
FIG. 8: Membrane Disruption and Bacterialcidal Effects of Myomerger Ectodomain.
Figure 8:
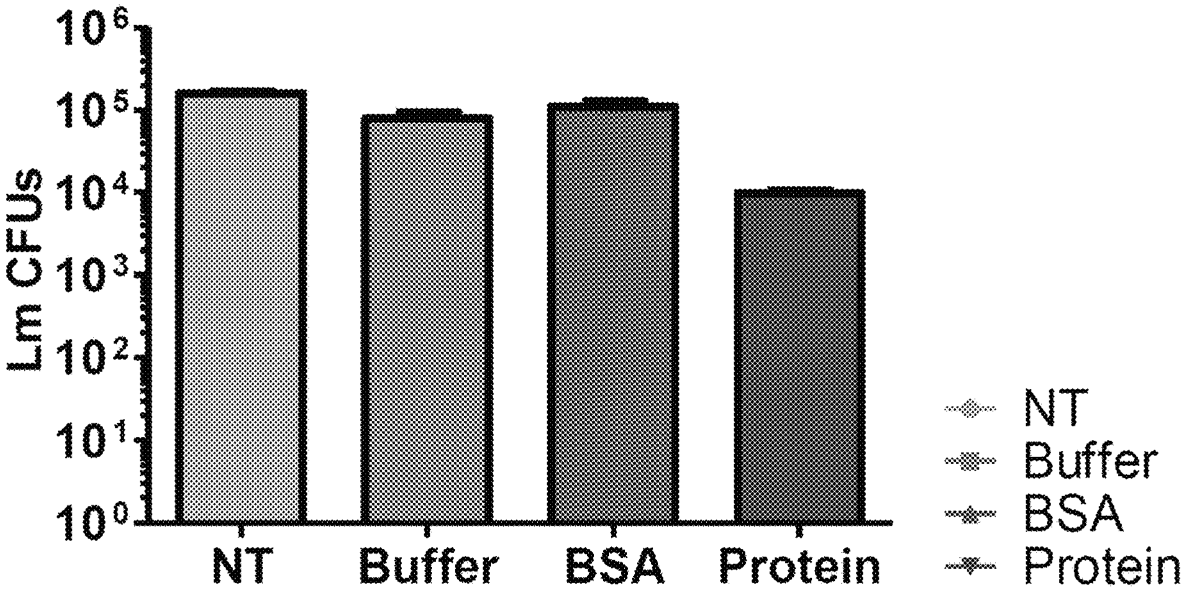
Figure 8:
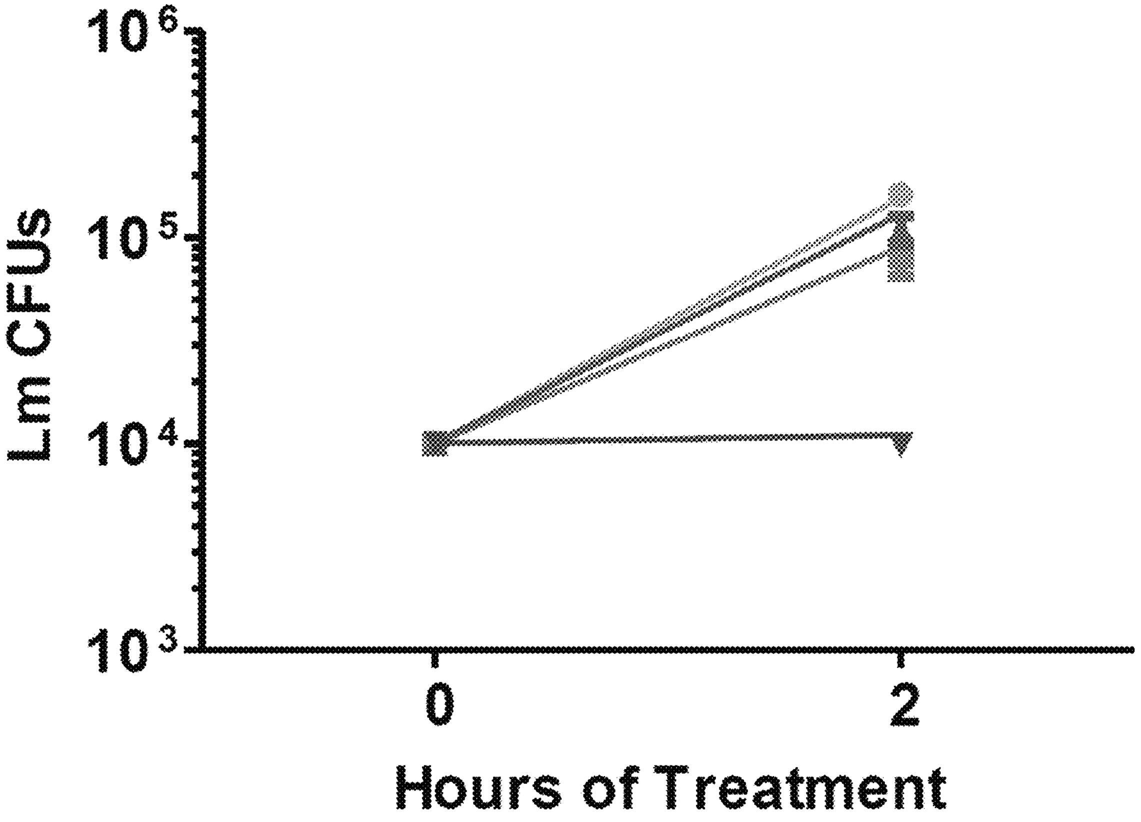
Figure 8:
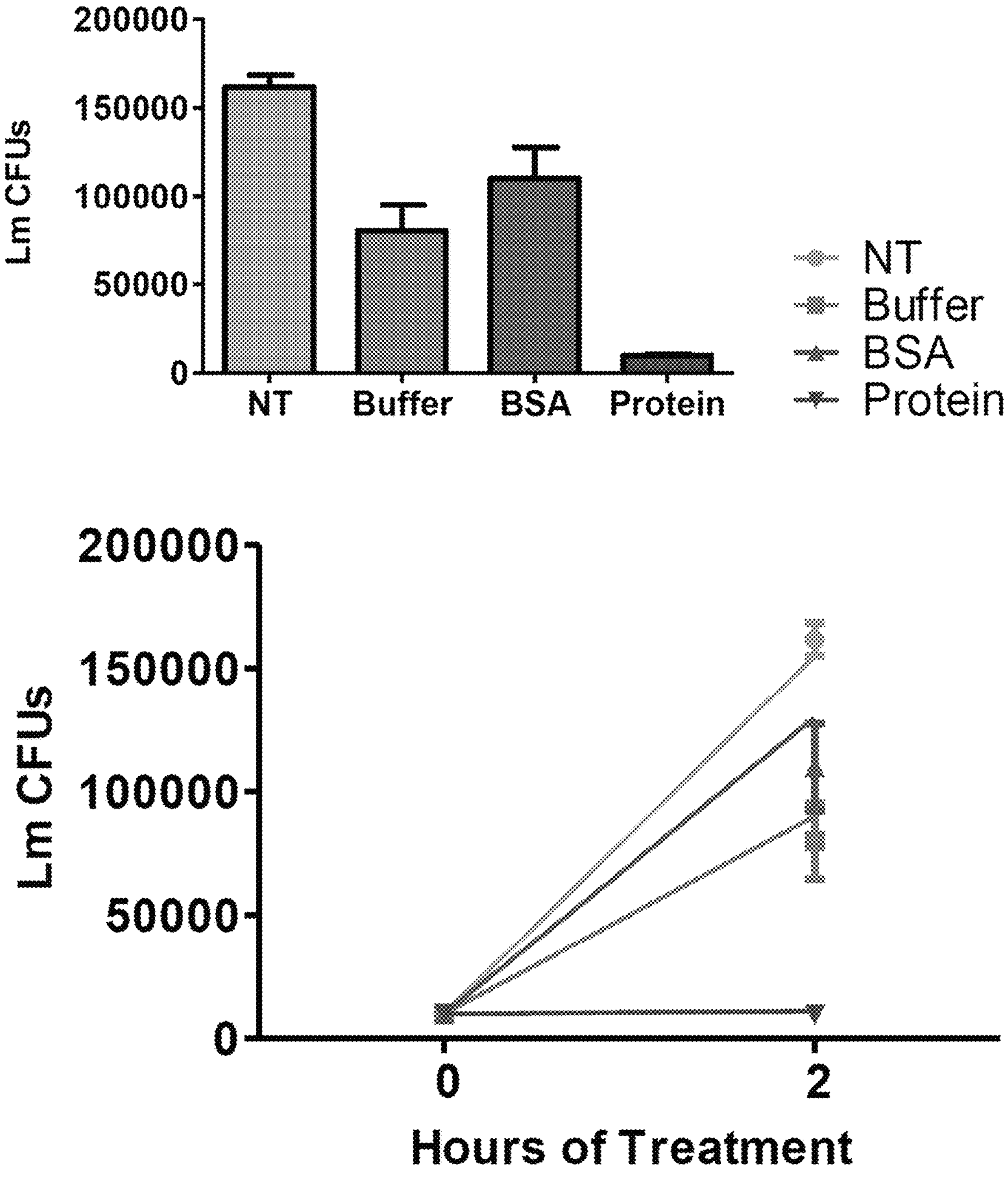
Figure 8:
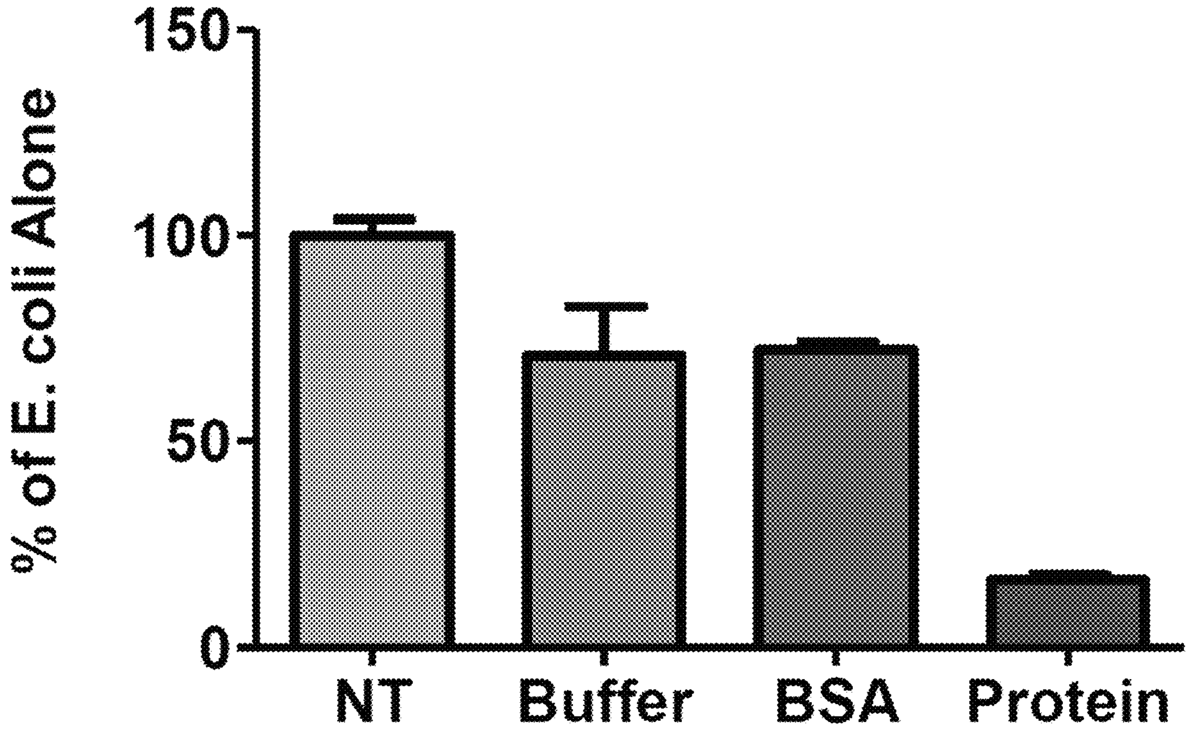
Figure 8:
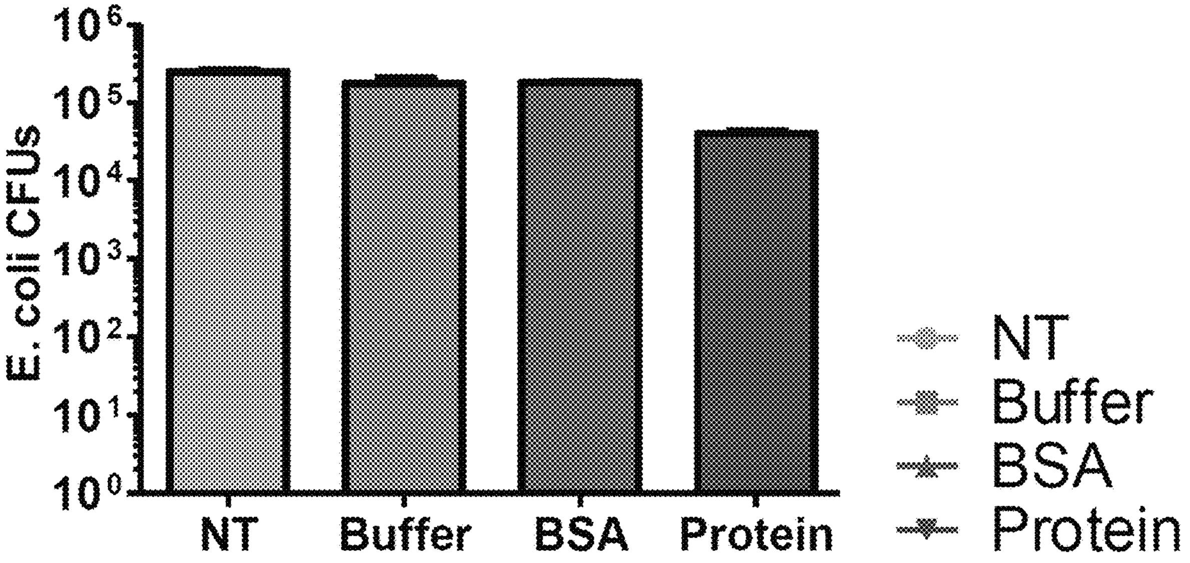
Figure 8:
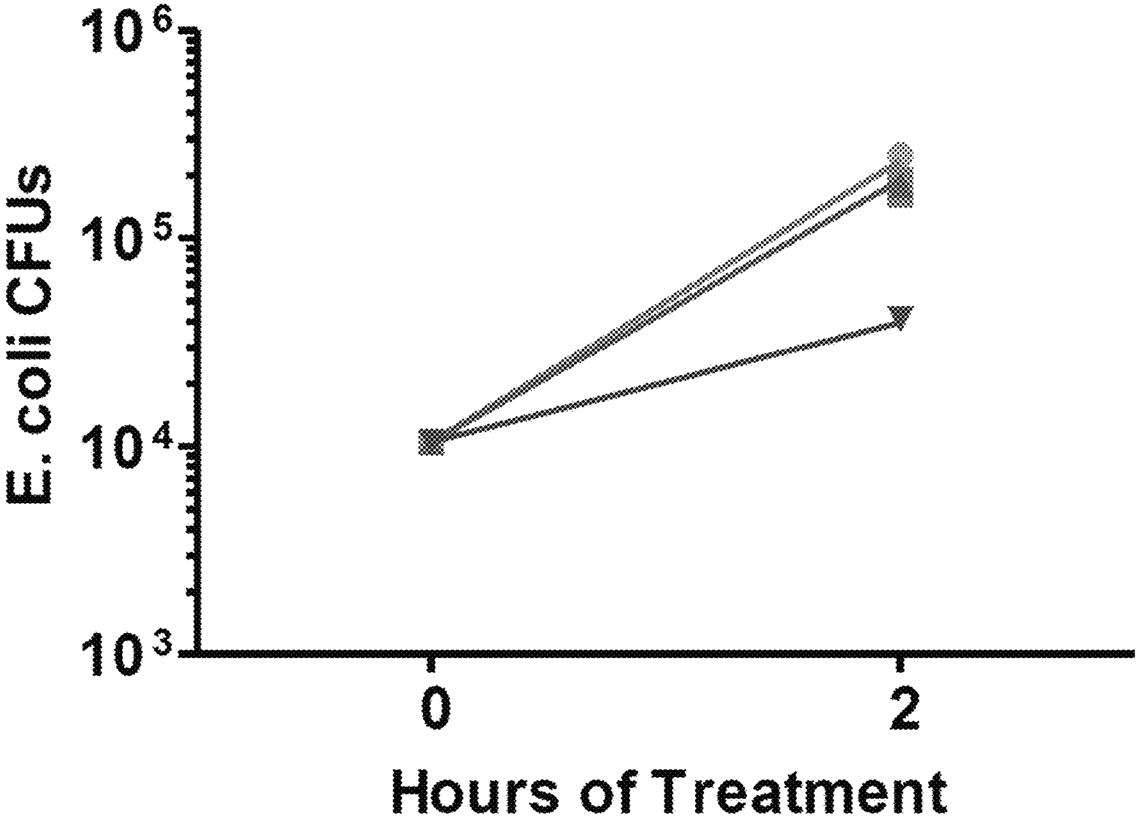
Figure 8:
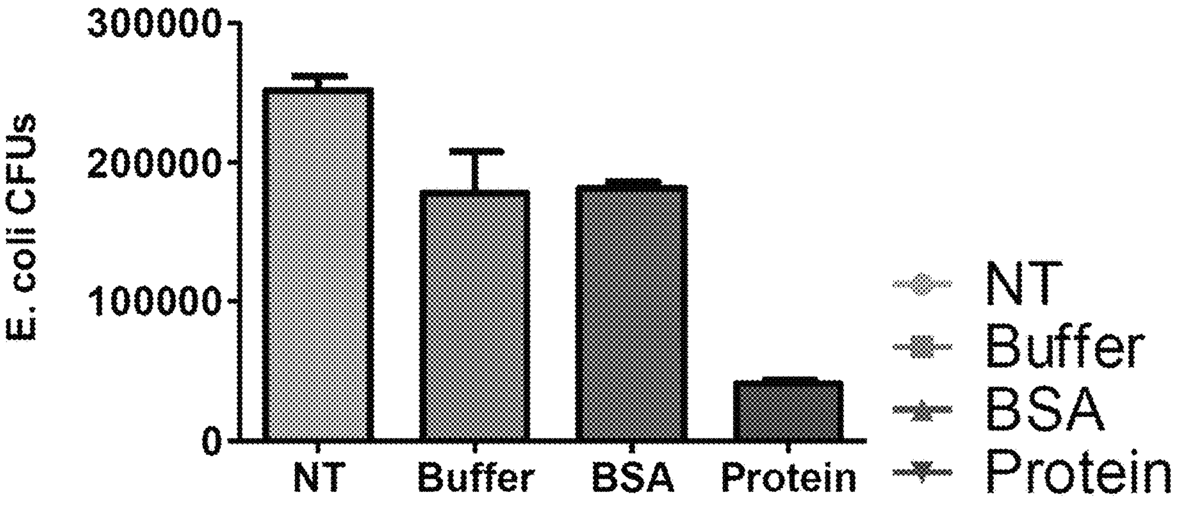
Figure 8:
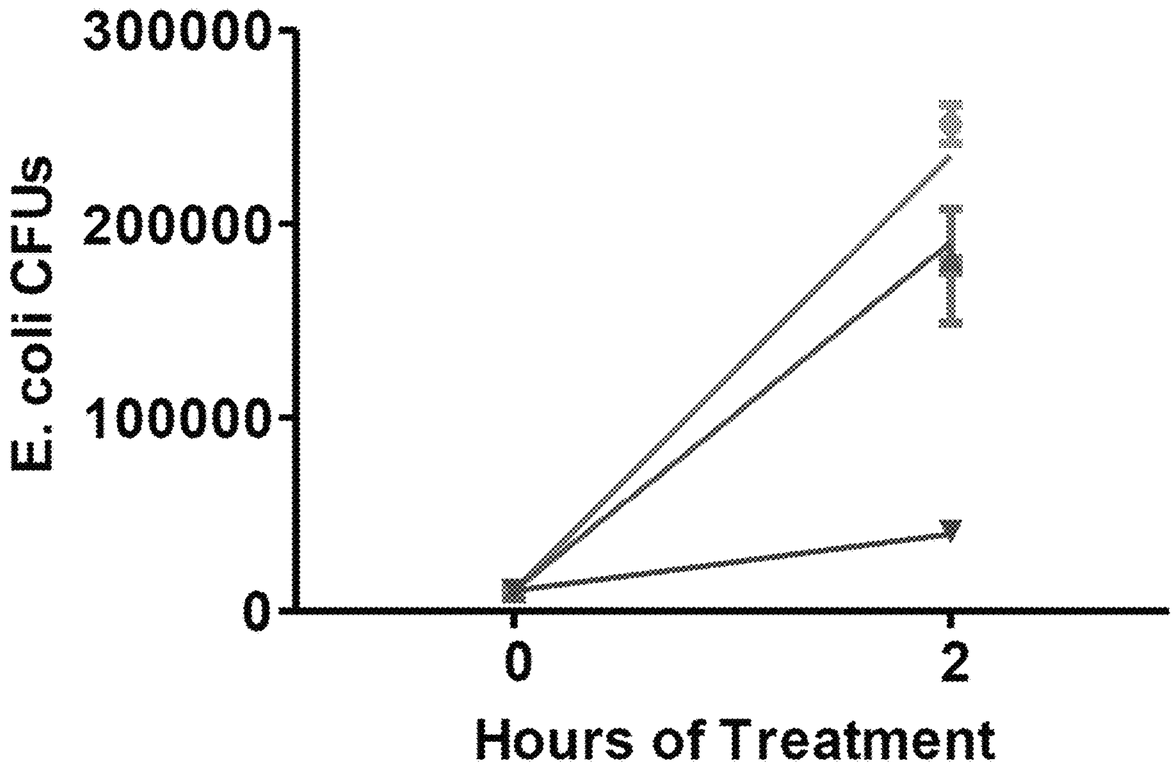

Gram-positive bacteria *Listeria monocytogenes* (Lm) and gram-negative bacteria *Escherichia coli* (*E. coli*) were treated with 25 μM recombinant Myomerger ectodomain (labeled as "protein" in FIG. 8) for 2 hours. Colony forming units (CFU) were measured, showing that Myomerger ectodomain disrupts the growth of both Lm and *E. coli* (FIG. 8). Myomerger appears to have more of an effect on gram-positive Lm as compared to gram-negative *E. Coli.*

Figure 9:
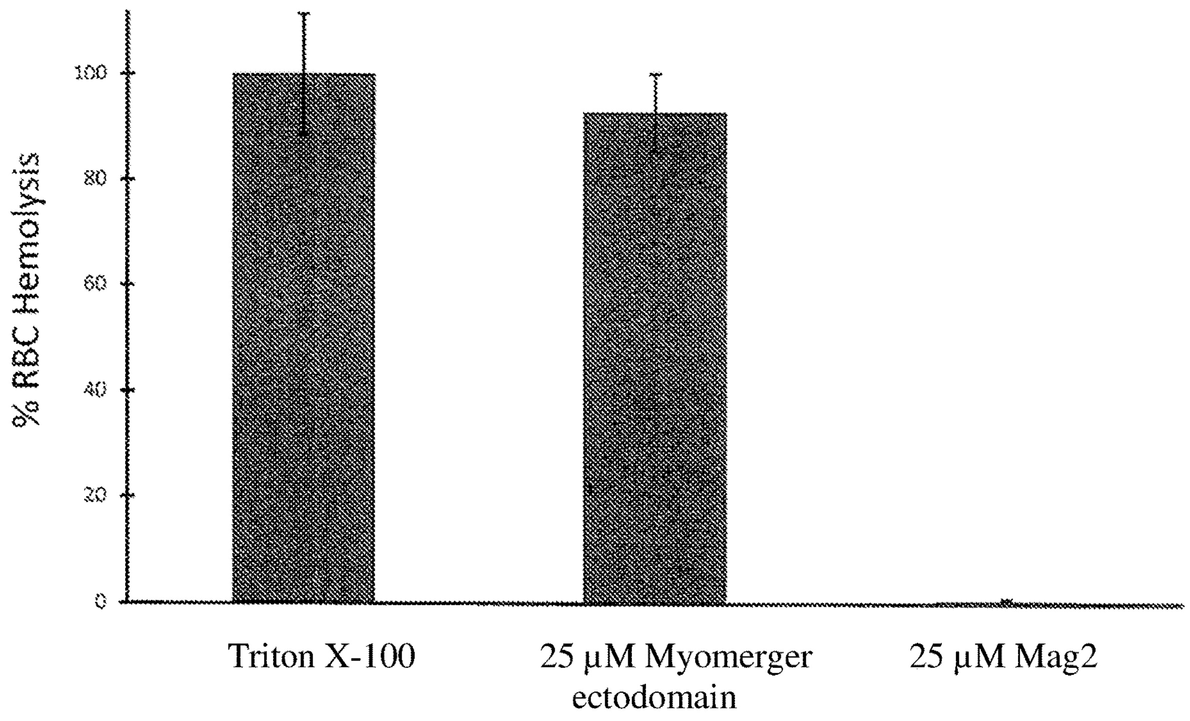
FIG. 9: Membrane Disruption and Red Blood Cell Hemolysis by Myomerger Ectodomain.

Myomerger ectodomain (amino acids 26-84) was added to mouse Red Blood Cells (RBCs) and hemolysis was measured using a spectrophotometer (FIG. 9). 25 μM Myomerger ectodomain induced lysis of RBCs while Mag2 (magainin 2), a known anti-microbial peptide, had no measurable effect. These data show that Myomerger ectodomain can disrupt cellular membranes and its activity appears to be different from Mag2.

The headings used in the disclosure are not meant to suggest that all disclosure relating to the heading is found within the section that starts with that heading. Disclosure for any subject may be found throughout the specification.

It is noted that terms like "preferably," "commonly," and "typically" are not used herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

As used in the disclosure, "a" or "an" means one or more than one, unless otherwise specified. As used in the claims, when used in conjunction with the word "comprising" the words "a" or "an" means one or more than one, unless otherwise specified. As used in the disclosure or claims, "another" means at least a second or more, unless otherwise specified. As used in the disclosure, the phrases "such as", "for example", and "e.g." mean "for example, but not limited to" in that the list following the term ("such as", "for example", or "e.g.") provides some examples but the list is not necessarily a fully inclusive list. The word "comprising" means that the items following the word "comprising" may include additional unrecited elements or steps; that is, "comprising" does not exclude additional unrecited steps or elements.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

Detailed descriptions of one or more embodiments are provided herein. It is to be understood, however, that the present invention may be embodied in various forms. Therefore, specific details disclosed herein (even if designated as preferred or advantageous) are not to be interpreted as limiting, but rather are to be used as an illustrative basis for the claims and as a representative basis for teaching one skilled in the art to employ the present invention in any appropriate manner. Indeed, various modifications of the invention in addition to those described herein will become apparent to those skilled in the art from the foregoing description and the accompanying figures. Such modifications are intended to fall within the scope of the appended claims.

What is claimed is:

1. A method for lysing a liposome or a cell selected from the group consisting of an animal cell or a bacterial cell, comprising contacting the liposome or the cell with an isolated extracellular myomerger polypeptide selected from the group consisting of SEQ ID NO: 19, SEQ ID NO: 20, SEQ ID NO: 21, SEQ ID NO: 22, SEQ ID NO: 23, and SEQ ID NO: 24 or a composition comprising the isolated extracellular myomerger polypeptide, a nucleic acid molecule encoding the isolated extracellular myomerger polypeptide, or a vector comprising the nucleic acid molecule, and lysing the liposome or the cell as a result of the contacting step, wherein the composition does not comprise myomaker polypeptide or a nucleic acid molecule encoding myomaker polypeptide.

2. The method of claim 1, wherein the method is for lysing the cell and the cell is a mammalian cell.

3. The method of claim 1, wherein the method is for lysing the cell and the cell is a bacterial cell or a mammalian cell.

4. The method of claim 1, wherein the method is for lysing the cell and the cell is a gram-positive bacterial cell or a gram-negative bacterial cell.

5. The method of claim 1, wherein the method is for lysing the cell and the cell is a cancer cell.

6. The method of claim 1, wherein the method is for lysing the cell and the cell is a cancer cell and the cancer cell is a tumor cell.

7. The method of claim 1, wherein the contacting occurs in vitro.

8. The method of claim 1, wherein the contacting occurs in vivo.

9. The method of claim 1, wherein the contacting comprises an injection.

10. The method of claim 1, wherein the method results in one or more pores in the cell membrane or the liposome membrane.

11. The method of claim 1, wherein the method comprises contacting the cell or the liposome with the isolated extracellular myomerger polypeptide or a composition comprising the isolated extracellular myomerger polypeptide.

12. The method of claim 11, wherein the isolated extracellular myomerger polypeptide is SEQ ID NO: 19.

13. The method of claim 11, wherein the isolated extracellular myomerger polypeptide is SEQ ID NO: 20.

14. The method of claim 11, wherein the isolated extracellular myomerger polypeptide is SEQ ID NO: 21.

15. The method of claim 11, wherein the isolated extracellular myomerger polypeptide is SEQ ID NO: 22.

16. The method of claim 11, wherein the isolated extracellular myomerger polypeptide is SEQ ID NO: 23.

17. The method of claim 11, wherein the isolated extracellular myomerger polypeptide is SEQ ID NO: 24.

18. The method of claim 1, wherein the isolated extracellular myomerger polypeptide is SEQ ID NO: 19.

19. The method of claim 1, wherein the isolated extracellular myomerger polypeptide is SEQ ID NO: 20.

20. The method of claim 1, wherein the isolated extracellular myomerger polypeptide is SEQ ID NO: 21.

21. The method of claim 1, wherein the isolated extracellular myomerger polypeptide is SEQ ID NO: 22.

22. The method of claim 1, wherein the isolated extracellular myomerger polypeptide is SEQ ID NO: 23.

23. The method of claim 1, wherein the isolated extracellular myomerger polypeptide is SEQ ID NO: 24.

24. The method of claim 1, wherein the nucleic acid molecule is included in a vector, a viral vector, or a plasmid.

25. The method of claim 1, wherein the amount of the isolated extracellular myomerger polypeptide, the nucleic acid molecule, or the vector is from about 0.0001% (by weight total composition) to about 99%.

26. The method of claim 1, wherein the composition is a pharmaceutical composition.

27. The method of claim 1, wherein (a) the composition is a pharmaceutical composition and (b) the amount of the isolated extracellular myomerger polypeptide, the nucleic acid molecule, or the vector is from about 0.0001% (by weight total composition) to about 50%.

* * * * *

SEQUENCE LISTING

```
<160> NUMBER OF SEQ ID NOS: 27

<210> SEQ ID NO 1
<211> LENGTH: 108
<212> TYPE: PRT
<213> ORGANISM: Artificial Sequence
<220> FEATURE:
<223> OTHER INFORMATION: Myomerger mouse-long

<400> SEQUENCE: 1

Met Pro Glu Glu Ser Cys Thr Val Lys Leu Ile Gln Leu Lys Thr Gly
1               5                   10                  15

Glu Tyr Arg Gly Ala Gly Pro Ala Met Pro Val Pro Leu Leu Pro Met
            20                  25                  30

Val Leu Arg Ser Leu Leu Ser Arg Leu Leu Leu Pro Val Ala Arg Leu
        35                  40                  45

Ala Arg Gln His Leu Leu Pro Leu Leu Arg Arg Leu Ala Arg Arg Leu
    50                  55                  60

Ser Ser Gln Asp Met Arg Glu Ala Leu Leu Ser Cys Leu Leu Phe Val
65                  70                  75                  80

Leu Ser Gln Gln Gln Pro Pro Asp Ser Gly Glu Ala Ser Arg Val Asp
                85                  90                  95

His Ser Gln Arg Lys Glu Arg Leu Gly Pro Gln Lys
            100                 105


<210> SEQ ID NO 2
<211> LENGTH: 84
<212> TYPE: PRT
<213> ORGANISM: Artificial Sequence
<220> FEATURE:
<223> OTHER INFORMATION: Myomerger - Mouse (short)

<400> SEQUENCE: 2

Met Pro Val Pro Leu Leu Pro Met Val Leu Arg Ser Leu Leu Ser Arg
1               5                   10                  15

Leu Leu Leu Pro Val Ala Arg Leu Ala Arg Gln His Leu Leu Pro Leu
            20                  25                  30
```

-continued

```
Leu Arg Arg Leu Ala Arg Arg Leu Ser Ser Gln Asp Met Arg Glu Ala
        35                  40                  45

Leu Leu Ser Cys Leu Leu Phe Val Leu Ser Gln Gln Gln Pro Pro Asp
    50                  55                  60

Ser Gly Glu Ala Ser Arg Val Asp His Ser Gln Arg Lys Glu Arg Leu
65                  70                  75                  80

Gly Pro Gln Lys


<210> SEQ ID NO 3
<211> LENGTH: 84
<212> TYPE: PRT
<213> ORGANISM: Artificial Sequence
<220> FEATURE:
<223> OTHER INFORMATION: Myomerger - Human

<400> SEQUENCE: 3

Met Pro Thr Pro Leu Leu Pro Leu Leu Leu Arg Leu Leu Leu Ser Cys
1               5                   10                  15

Leu Leu Leu Pro Ala Ala Arg Leu Ala Arg Gln Tyr Leu Leu Pro Leu
            20                  25                  30

Leu Arg Arg Leu Ala Arg Arg Leu Gly Ser Gln Asp Met Arg Glu Ala
        35                  40                  45

Leu Leu Gly Cys Leu Leu Phe Ile Leu Ser Gln Arg His Ser Pro Asp
    50                  55                  60

Ala Gly Glu Ala Ser Arg Val Asp Arg Leu Glu Arg Arg Glu Arg Leu
65                  70                  75                  80

Gly Pro Gln Lys


<210> SEQ ID NO 4
<211> LENGTH: 84
<212> TYPE: PRT
<213> ORGANISM: Artificial Sequence
<220> FEATURE:
<223> OTHER INFORMATION: Myomerger - Cat

<400> SEQUENCE: 4

Met Pro Ala Pro Leu Leu Pro Leu Leu Leu Arg Thr Leu Met Ser Arg
1               5                   10                  15

Leu Leu Leu Pro Ala Thr Arg Leu Ala Arg Arg His Leu Leu Pro Leu
            20                  25                  30

Leu Arg Arg Leu Ala Arg Arg Leu Gly Ser Gln Asp Val Arg Glu Ala
        35                  40                  45

Leu Leu Gly Cys Leu Leu Phe Ile Leu Ser Gln Ser Arg Pro Pro Asp
    50                  55                  60

Ala Glu Glu Val Ser Arg Val Ala Gly Gln Glu Arg Arg Glu Arg Leu
65                  70                  75                  80

Ala Pro Pro Lys


<210> SEQ ID NO 5
<211> LENGTH: 85
<212> TYPE: PRT
<213> ORGANISM: Artificial Sequence
<220> FEATURE:
<223> OTHER INFORMATION: Myomerger - Rabbit

<400> SEQUENCE: 5

Met Pro Ala Pro Leu Leu Pro Leu Leu Leu Arg Thr Leu Leu Ser Arg
1               5                   10                  15
```

-continued

```
Leu Leu Leu Pro Ala Ala Arg Leu Ala Arg Arg His Leu Leu Pro Leu
            20                  25                  30

Leu Arg Arg Leu Ala Gln Arg Leu Gly Ser Gln Gly Thr Arg Glu Ala
        35                  40                  45

Leu Leu Gly Cys Leu Leu Phe Val Leu Ser Gln Arg Gln Pro Pro Asp
    50                  55                  60

Ala Ser Gly Glu Ala Ser Arg Val Asp Pro Pro Glu Arg Lys Glu Arg
65                  70                  75                  80

Leu Gly Arg Gln Lys
                85


<210> SEQ ID NO 6
<211> LENGTH: 84
<212> TYPE: PRT
<213> ORGANISM: Artificial Sequence
<220> FEATURE:
<223> OTHER INFORMATION: Myomerger - Dog

<400> SEQUENCE: 6

Met Pro Ala Pro Leu Leu Pro Leu Leu Leu Arg Thr Leu Val Ser Arg
1               5                   10                  15

Leu Leu Leu Pro Ala Ala Arg Leu Ala Arg Arg His Leu Leu Pro Leu
            20                  25                  30

Leu Arg Gly Leu Ala Arg Arg Leu Gly Ser Gln Glu Val Arg Glu Ala
        35                  40                  45

Leu Leu Gly Cys Leu Leu Phe Ile Leu Ser Gln Arg His Pro Pro Asp
    50                  55                  60

Ala Glu Glu Ala Ser Arg Val Ala Gly Gln Glu Arg Lys Glu Arg Leu
65                  70                  75                  80

Ala Pro Pro Lys


<210> SEQ ID NO 7
<211> LENGTH: 84
<212> TYPE: PRT
<213> ORGANISM: Artificial Sequence
<220> FEATURE:
<223> OTHER INFORMATION: Myomerger - Elephant

<400> SEQUENCE: 7

Met Pro Val Pro Leu Leu Ser Leu Leu Leu Arg Ala Leu Leu Ser Arg
1               5                   10                  15

Leu Leu Leu Pro Ala Ala Arg Leu Ala Arg Gln His Leu Leu Pro Leu
            20                  25                  30

Leu Arg Arg Leu Ala Arg Arg Leu Gly Ser Gln Asp Met Arg Gln Ala
        35                  40                  45

Leu Leu Gly Cys Leu Leu Phe Val Leu Ser Gln Gln His Pro Pro Asp
    50                  55                  60

Ala Gly Glu Ala Ser Arg Glu Ala Leu Ser Glu Arg Arg Gly Arg Leu
65                  70                  75                  80

Ala Pro Gln Lys


<210> SEQ ID NO 8
<211> LENGTH: 327
<212> TYPE: DNA
<213> ORGANISM: Artificial Sequence
<220> FEATURE:
<223> OTHER INFORMATION: Myomerger - Mouse (long) cDNA

<400> SEQUENCE: 8
```

-continued atgccagaag aaagctgcac tgtaaaacta atccagttga aaactgggga gtacagaggt 60
gcaggtcctg ccatgcccgt tccattgctc ccgatggtgc ttcgatcgct gctgtcccgc 120
ctgctgctgc ctgttgcccg cctggcccgg cagcacctcc tgcccttgct gcgccggctg 180
gcccgccgac tgagctccca agacatgaga gaggctctgc tgagctgtct gctctttgtc 240
ctcagccagc aacagccacc ggattctgga gaggcctcca gagtggacca ctcccagagg 300
aaggagagat tgggcccccca gaagtga 327

<210> SEQ ID NO 9
<211> LENGTH: 255
<212> TYPE: DNA
<213> ORGANISM: Artificial Sequence
<220> FEATURE:
<223> OTHER INFORMATION: Myomerger - Mouse (short) cDNA

<400> SEQUENCE: 9
atgcccgttc cattgctccc gatggtgctt cgatcgctgc tgtcccgcct gctgctgcct 60
gttgcccgcc tggcccggca gcacctcctg cccttgctgc gccggctggc ccgccgactg 120
agctcccaag acatgagaga ggctctgctg agctgtctgc tctttgtcct cagccagcaa 180
cagccaccgg attctggaga ggcctccaga gtggaccact cccagaggaa ggagagattg 240
ggcccccaga agtga 255

<210> SEQ ID NO 10
<211> LENGTH: 255
<212> TYPE: DNA
<213> ORGANISM: Artificial Sequence
<220> FEATURE:
<223> OTHER INFORMATION: Myomerger - Human cDNA

<400> SEQUENCE: 10
atgcccacgc cactgctccc gctgctgctt cgattgctgc tgtcctgcct gctgctgcct 60
gctgcccgcc tggcccgcca atacctcctg cccctgctgc gccgattggc ccgccgcctg 120
ggctcccagg acatgcgaga ggctttgctg ggctgtctgc tgttcattct cagccagcga 180
cactcgccag acgctgggga ggcctcaaga gtggaccgcc tggagaggag ggagaggtta 240
ggcccccaaa agtga 255

<210> SEQ ID NO 11
<211> LENGTH: 255
<212> TYPE: DNA
<213> ORGANISM: Artificial Sequence
<220> FEATURE:
<223> OTHER INFORMATION: Myomerger - Cat cDNA

<400> SEQUENCE: 11
atgcccgctc cactgctccc actgctgctt cgaaccctga tgtcccgctt gctgctgcct 60
gccacccgcc tggcccgccg gcacctcctg cccctcctgc gccgactggc ccgccgcctg 120
ggctcgcagg atgttcgaga agctttgctg ggctgtctgt tgttcatcct cagccagagc 180
cgcccgcccg acgctgagga ggtctccaga gtggctggcc aggagaggag ggagaggcta 240
gctcccccaa aatga 255

<210> SEQ ID NO 12
<211> LENGTH: 258
<212> TYPE: DNA
<213> ORGANISM: Artificial Sequence
<220> FEATURE:
<223> OTHER INFORMATION: Myomerger - Rabbit cDNA -continued

<400> SEQUENCE: 12
atgcctgccc ccctgctgcc gctgctgctg cgaacgctgc tgtcccgtct gctgctgccc 60
gctgcccgcc tggcccgccg gcacctcctg cccctgctgc gccgactggc tcaacgcctg 120
ggctcccagg gcacgcgcga ggctttgctg ggctgtttgc tgtttgtcct cagccagaga 180
cagccgccag atgcctctgg ggaggcctcc agagtggacc caccggagag gaaggagagg 240
ttaggccgcc aaaagtga 258

<210> SEQ ID NO 13
<211> LENGTH: 255
<212> TYPE: DNA
<213> ORGANISM: Artificial Sequence
<220> FEATURE:
<223> OTHER INFORMATION: Myomerger - Dog cDNA

<400> SEQUENCE: 13
atgcctgctc cactgctccc actgctgctg cgaacgctgg tgtctcgcct gctgctgcct 60
gctgcccgcc tggcccggcg gcacctcctg cccctgctgc gtggactggc ccgccgccta 120
ggctcgcagg aggttcgaga ggctttgctg ggctgtctgt tgttcatcct cagccagaga 180
catccgccgg acgccgagga ggcctccaga gtggctggcc aggagaggaa ggagaggcta 240
gctcccccca aatga 255

<210> SEQ ID NO 14
<211> LENGTH: 255
<212> TYPE: DNA
<213> ORGANISM: Artificial Sequence
<220> FEATURE:
<223> OTHER INFORMATION: Myomerger - Elephant cDNA

<400> SEQUENCE: 14
atgcccgtcc cgctgctctc gctgctgctg cgcgcgctgc tgtcccgcct gctgctgcct 60
gctgcccgcc tggcccgcca gcacctcctg cccctcctgc gccgacttgc tcgccgcctg 120
ggctcccagg acatgcgaca ggctctcttg ggatgtctgc tctttgtcct cagccagcaa 180
cacccgccgg acgctggtga ggcctccaga gaggccctct cagagaggag agggaggcta 240
gccccccaaa agtga 255

<210> SEQ ID NO 15
<211> LENGTH: 1275
<212> TYPE: DNA
<213> ORGANISM: Artificial Sequence
<220> FEATURE:
<223> OTHER INFORMATION: Myomerger - Human (+strand)

<400> SEQUENCE: 15
ctgcccggtg agagctgccg tggattggtg ggggtagggg actgagaggt cagggagtgt 60
caggtcaggg tggatcagga gccccaaaag aaaaattgag aattgcctgg agaagaactc 120
ctgctagact gagggagaag ggttagggaa ctccaggggc attgaggctg tgcaagagga 180
gggggtgact agaggaaggg aggggccagg gagcagtagg aatgcctgga gctgggaacg 240
gcaagctgta ggtcttggtt tactcttgcc ttggttcagt ctccccatct gtgctatggt 300
gagaaccttc ctgcctcagc tgccttgcca agagaaaggg cttcatgaaa gcaaaaatga 360
cctacaaatt gaggtcagga gcaggaaggt gtaaactgaa gggaggggga actcctgccc 420
accccatgtc cttgccaggt gaggcagaac caggacatgc aagcctaaag tctgtgttgt 480

```
cttcccaggc actgactcac tggccctgcc atgcccacgc cactgctccc gctgctgctt    540
cgattgctgc tgtcctgcct gctgctgcct gctgcccgcc tggcccgcca atacctcctg    600
cccctgctgc gccgattggc ccgccgcctg ggctcccagg acatgcgaga ggctttgctg    660
ggctgtctgc tgttcattct cagccagcga cactcgccag acgctgggga ggcctcaaga    720
gtggaccgcc tggagaggag ggagaggtta ggcccccaaa agtgaggcca caagtcctgg    780
cagcagctgt atccacaaaa tgctttcttt tggagtagga taatcctggc accagcactg    840
accgaagcct gcccagtgga cagaagatat agtgagggtt gtgcatgaga gggatctgcc    900
acagacatgc ctctccactc ccaacagaaa tgtctttctg gaagaatgcc ttgcatctag    960
cacaaaactg attattgccc ctctgtcctc cagcagttcc tcccaaagac cactcctaat   1020
cacctctggc ctcaggcggg aggggaacta acacccaccc acccctgccc tccctgcaaa   1080
tgggaacatc aaggttccca gtgcttaact gagggacaag tgacaattta gcagagaggc   1140
aagatttgaa tccagactgt cttccagact caggacctac cttaaaataa tatctgagtt   1200
gcttatggag gcagacctgc ctgcaaagcc cagcactcag caagtgctca ataaatattt   1260
gatttgaatt ctttc                                                    1275
```

<210> SEQ ID NO 16
<211> LENGTH: 1275
<212> TYPE: DNA
<213> ORGANISM: Artificial Sequence
<220> FEATURE:
<223> OTHER INFORMATION: Myomerger - Human (-strand, reverse complement)

<400> SEQUENCE: 16

```
gaaagaattc aaatcaaata tttattgagc acttgctgag tgctgggctt tgcaggcagg     60
tctgcctcca taagcaactc agatattatt ttaaggtagg tcctgagtct ggaagacagt    120
ctggattcaa atcttgcctc tctgctaaat tgtcacttgt ccctcagtta agcactggga    180
accttgatgt tcccatttgc agggagggca ggggtgggtg ggtgttagtt cccctcccgc    240
ctgaggccag aggtgattag gagtggtctt tgggaggaac tgctggagga cagaggggca    300
ataatcagtt ttgtgctaga tgcaaggcat tcttccagaa agacatttct gttgggagtg    360
gagaggcatg tctgtggcag atccctctca tgcacaaccc tcactatatc ttctgtccac    420
tgggcaggct tcggtcagtg ctggtgccag gattatccta ctccaaaaga aagcattttg    480
tggatacagc tgctgccagg acttgtggcc tcacttttgg gggcctaacc tctccctcct    540
ctccaggcgg tccactcttg aggcctcccc agcgtctggc gagtgtcgct ggctgagaat    600
gaacagcaga cagcccagca aagcctctcg catgtcctgg gagcccaggc ggcgggccaa    660
tcggcgcagc aggggcagga ggtattggcg ggccaggcgg gcagcaggca gcagcaggca    720
ggacagcagc aatcgaagca gcagcgggag cagtggcgtg ggcatggcag ggccagtgag    780
tcagtgcctg ggaagacaac acagacttta ggcttgcatg tcctggttct gcctcacctg    840
gcaaggacat ggggtgggca ggagttcccc ctcccttcag tttacacctt cctgctcctg    900
acctcaattt gtaggtcatt tttgctttca tgaagccctt tctcttggca aggcagctga    960
ggcaggaagg ttctcaccat agcacagatg gggagactga accaaggcaa gagtaaacca   1020
agacctacag cttgccgttc ccagctccag gcattcctac tgctccctgg cccctccctt   1080
cctctagtca ccccctcctc ttgcacagcc tcaatgcccc tggagttccc taacccttct   1140
ccctcagtct agcaggagtt cttctccagg caattctcaa tttttctttt ggggctcctg   1200
atccaccctg acctgacact ccctgacctc tcagtcccct acccccacca atccacggca   1260
```

gctctcaccg ggcag 1275

<210> SEQ ID NO 17
<211> LENGTH: 1136
<212> TYPE: DNA
<213> ORGANISM: Artificial Sequence
<220> FEATURE:
<223> OTHER INFORMATION: Myomerger - Mouse (+strand)

<400> SEQUENCE: 17
ccaataacaa cacactgtcc tcgtttattg actacctgct gcgtaccaag ctttgaaagt 60
actcattctt taacgggaag caagggctta taattttaag gtagacggga cagtttggat 120
ttaaatacca cctcttagct aaattgtctt gagtctaagt gaaacatcat ctcttaactg 180
accttgatac ccgcatttgc aggtccaccc tggaggccag agataaggca gagggagctg 240
cagagaggaa gggtcaatca acacaatctg tagcctgcta ggagctaggg gagtgggaac 300
tgttcaggtc agagccctct tgcactcagc ccggactgtc ttcgcccact gggcagtctg 360
ccgtccatgc ccgtgcgtgc ggaccgacgc ctggactaac cggctccaaa agtactttga 420
tgggcgttgc tgtttccagg acccgtggcc tcacttctgg gggcccaatc tctccttcct 480
ctgggagtgg tccactctgg aggcctctcc agaatccggt ggctgttgct ggctgaggac 540
aaagagcaga cagctcagca gagcctctct catgtcttgg gagctcagtc ggcgggccag 600
ccggcgcagc aagggcagga ggtgctgccg ggccaggcgg gcaacaggca gcagcaggcg 660
ggacagcagc gatcgaagca ccatcgggag caatggaacg ggcatggcag gacctgcacc 720
tgcaaaggga acccgggttt tagactgtac ctcaggcacg cacctcacct ggcaaagcag 780
ggtgcggggg tgtggagtcc tcccttcagc ttatacctct gtactcccca gttttcaact 840
ggattagttt tacagtgcag ctttcttctg gcatgaaagc tggttaagga gttcactcac 900
tgttatcaca gatgggaagg gagcccaggg ctggaaggtg gtggggactg aggctagggc 960
cttttccaga acccacttcc tttaatccct ccctcccttt gcatactctg acctgaagcc 1020
tgaacttctt gccctcctgc tcaccagttc taaccggcca gtggcagctc tcaccagtca 1080
gaactgctca gaatcaattt caggatgctt ttgcctgcgg tggattcagc atcact 1136

<210> SEQ ID NO 18
<211> LENGTH: 1136
<212> TYPE: DNA
<213> ORGANISM: Artificial Sequence
<220> FEATURE:
<223> OTHER INFORMATION: Myomerger - Mouse (-strand, reverse complement)

<400> SEQUENCE: 18
agtgatgctg aatccaccgc aggcaaaagc atcctgaaat tgattctgag cagttctgac 60
tggtgagagc tgccactggc cggttagaac tggtgagcag gagggcaaga agttcaggct 120
tcaggtcaga gtatgcaaag ggagggaggg attaaaggaa gtgggttctg gaaaaggccc 180
tagcctcagt ccccaccacc ttccagccct gggctccctt cccatctgtg ataacagtga 240
gtgaactcct taaccagctt tcatgccaga agaaagctgc actgtaaaac taatccagtt 300
gaaaactggg gagtacagag gtataagctg aagggaggac tccacacccc cgcaccctgc 360
tttgccaggt gaggtgcgtg cctgaggtac agtctaaaac ccgggttccc tttgcaggtg 420
caggtcctgc catgcccgtt ccattgctcc cgatggtgct tcgatcgctg ctgtcccgcc 480
tgctgctgcc tgttgcccgc ctggcccggc agcacctcct gcccttgctg cgccggctgg 540

-continued

```
cccgccgact gagctcccaa gacatgagag aggctctgct gagctgtctg ctctttgtcc    600

tcagccagca acagccaccg gattctggag aggcctccag agtggaccac tcccagagga    660

aggagagatt gggcccccag aagtgaggcc acgggtcctg gaaacagcaa cgcccatcaa    720

agtacttttg gagccggtta gtccaggcgt cggtccgcac gcacgggcat ggacggcaga    780

ctgcccagtg ggcgaagaca gtccgggctg agtgcaagag ggctctgacc tgaacagttc    840

ccactcccct agctcctagc aggctacaga ttgtgttgat tgacccttcc tctctgcagc    900

tccctctgcc ttatctctgg cctccagggt ggacctgcaa atgcgggtat caaggtcagt    960

taagagatga tgtttcactt agactcaaga caatttagct aagaggtggt atttaaatcc   1020

aaactgtccc gtctacctta aaattataag cccttgcttc ccgttaaaga atgagtactt   1080

tcaaagcttg gtacgcagca ggtagtcaat aaacgaggac agtgtgttgt tattgg       1136


<210> SEQ ID NO 19
<211> LENGTH: 59
<212> TYPE: PRT
<213> ORGANISM: Artificial Sequence
<220> FEATURE:
<223> OTHER INFORMATION: Extracellular Myomerger - Mouse

<400> SEQUENCE: 19

Arg Gln His Leu Leu Pro Leu Leu Arg Arg Leu Ala Arg Arg Leu Ser
1               5                   10                  15

Ser Gln Asp Met Arg Glu Ala Leu Leu Ser Cys Leu Leu Phe Val Leu
            20                  25                  30

Ser Gln Gln Gln Pro Pro Asp Ser Gly Glu Ala Ser Arg Val Asp His
        35                  40                  45

Ser Gln Arg Lys Glu Arg Leu Gly Pro Gln Lys
    50                  55


<210> SEQ ID NO 20
<211> LENGTH: 59
<212> TYPE: PRT
<213> ORGANISM: Artificial Sequence
<220> FEATURE:
<223> OTHER INFORMATION: Extracellular Myomerger - Human

<400> SEQUENCE: 20

Arg Gln Tyr Leu Leu Pro Leu Leu Arg Arg Leu Ala Arg Arg Leu Gly
1               5                   10                  15

Ser Gln Asp Met Arg Glu Ala Leu Leu Gly Cys Leu Leu Phe Ile Leu
            20                  25                  30

Ser Gln Arg His Ser Pro Asp Ala Gly Glu Ala Ser Arg Val Asp Arg
        35                  40                  45

Leu Glu Arg Arg Glu Arg Leu Gly Pro Gln Lys
    50                  55


<210> SEQ ID NO 21
<211> LENGTH: 59
<212> TYPE: PRT
<213> ORGANISM: Artificial Sequence
<220> FEATURE:
<223> OTHER INFORMATION: Extracellular Myomerger - Cat

<400> SEQUENCE: 21

Arg Arg His Leu Leu Pro Leu Leu Arg Arg Leu Ala Arg Arg Leu Gly
1               5                   10                  15

Ser Gln Asp Val Arg Glu Ala Leu Leu Gly Cys Leu Leu Phe Ile Leu
            20                  25                  30
```

```
Ser Gln Ser Arg Pro Pro Asp Ala Glu Glu Val Ser Arg Val Ala Gly
        35                  40                  45

Gln Glu Arg Arg Glu Arg Leu Ala Pro Pro Lys
    50                  55


<210> SEQ ID NO 22
<211> LENGTH: 60
<212> TYPE: PRT
<213> ORGANISM: Artificial Sequence
<220> FEATURE:
<223> OTHER INFORMATION: Extracellular Myomerger - Rabbit

<400> SEQUENCE: 22

Arg Arg His Leu Leu Pro Leu Leu Arg Arg Leu Ala Gln Arg Leu Gly
1               5                   10                  15

Ser Gln Gly Thr Arg Glu Ala Leu Leu Gly Cys Leu Leu Phe Val Leu
            20                  25                  30

Ser Gln Arg Gln Pro Pro Asp Ala Ser Gly Glu Ala Ser Arg Val Asp
        35                  40                  45

Pro Pro Glu Arg Lys Glu Arg Leu Gly Arg Gln Lys
    50                  55                  60


<210> SEQ ID NO 23
<211> LENGTH: 59
<212> TYPE: PRT
<213> ORGANISM: Artificial Sequence
<220> FEATURE:
<223> OTHER INFORMATION: Extracellular Myomerger - Dog

<400> SEQUENCE: 23

Arg Arg His Leu Leu Pro Leu Leu Arg Gly Leu Ala Arg Arg Leu Gly
1               5                   10                  15

Ser Gln Glu Val Arg Glu Ala Leu Leu Gly Cys Leu Leu Phe Ile Leu
            20                  25                  30

Ser Gln Arg His Pro Pro Asp Ala Glu Glu Ala Ser Arg Val Ala Gly
        35                  40                  45

Gln Glu Arg Lys Glu Arg Leu Ala Pro Pro Lys
    50                  55


<210> SEQ ID NO 24
<211> LENGTH: 59
<212> TYPE: PRT
<213> ORGANISM: Artificial Sequence
<220> FEATURE:
<223> OTHER INFORMATION: Extracellular Myomerger - Elephant

<400> SEQUENCE: 24

Arg Gln His Leu Leu Pro Leu Leu Arg Arg Leu Ala Arg Arg Leu Gly
1               5                   10                  15

Ser Gln Asp Met Arg Gln Ala Leu Leu Gly Cys Leu Leu Phe Val Leu
            20                  25                  30

Ser Gln Gln His Pro Pro Asp Ala Gly Glu Ala Ser Arg Glu Ala Leu
        35                  40                  45

Ser Glu Arg Arg Gly Arg Leu Ala Pro Gln Lys
    50                  55


<210> SEQ ID NO 25
<211> LENGTH: 12
<212> TYPE: PRT
<213> ORGANISM: Artificial Sequence
<220> FEATURE:
```

-continued

```
<223> OTHER INFORMATION: alpha helix 1

<400> SEQUENCE: 25

Leu Leu Pro Leu Leu Arg Arg Leu Ala Arg Arg Leu
1               5                   10


<210> SEQ ID NO 26
<211> LENGTH: 15
<212> TYPE: PRT
<213> ORGANISM: Artificial Sequence
<220> FEATURE:
<223> OTHER INFORMATION: alpha helix 2

<400> SEQUENCE: 26

Gln Asp Met Arg Glu Ala Leu Leu Ser Cys Leu Leu Phe Val Leu
1               5                   10                  15


<210> SEQ ID NO 27
<211> LENGTH: 15
<212> TYPE: PRT
<213> ORGANISM: Artificial Sequence
<220> FEATURE:
<223> OTHER INFORMATION: alpha helix 2

<400> SEQUENCE: 27

Gln Asp Met Arg Glu Ala Leu Leu Gly Cys Leu Leu Phe Ile Leu
1               5                   10                  15
```